(12) United States Patent
Sato et al.

(10) Patent No.: US 8,445,669 B2
(45) Date of Patent: May 21, 2013

(54) PRODUCTION PROCESS OF ETHYNYLTHYMIDINE COMPOUNDS FROM 5-METHYLURIDINE AS A STARTING MATERIAL

(75) Inventors: Tatsunori Sato, Hyogo (JP); Tetsuya Kawashima, Hyogo (JP); Toshio Miwa, Osaka (JP); Kazutoyo Dokei, Osaka (JP); Chikoto Fujimoto, Saitama (JP)

(73) Assignee: Hamari Chemicals, Ltd., Osaka (JP)

( * ) Notice: Subject to any disclaimer, the term of this patent is extended or adjusted under 35 U.S.C. 154(b) by 361 days.

(21) Appl. No.: 12/936,789

(22) PCT Filed: Apr. 10, 2009

(86) PCT No.: PCT/JP2009/057362
§ 371 (c)(1),
(2), (4) Date: Nov. 17, 2010

(87) PCT Pub. No.: WO2009/125841
PCT Pub. Date: Oct. 15, 2009

(65) Prior Publication Data
US 2011/0054164 A1 Mar. 3, 2011

(30) Foreign Application Priority Data
Apr. 10, 2008 (JP) ................................. 2008-102895

(51) Int. Cl.
*C07H 19/167* (2006.01)

(52) U.S. Cl.
USPC ....................... 536/28.2; 536/28.54

(58) Field of Classification Search
None
See application file for complete search history.

(56) References Cited

U.S. PATENT DOCUMENTS

| | | | |
|---|---|---|---|
| 5,625,057 A | 4/1997 | Shiragami et al. | |
| 7,589,078 B2 * | 9/2009 | Cheng et al. | 514/49 |
| 8,193,165 B2 * | 6/2012 | Cheng et al. | 514/49 |
| 8,334,295 B2 * | 12/2012 | Guo et al. | 514/274 |
| 2004/0006002 A1 | 1/2004 | Sommadossi et al. | |
| 2004/0167096 A1 | 8/2004 | Cheng et al. | |
| 2007/0042988 A1 | 2/2007 | Klumpp et al. | |

FOREIGN PATENT DOCUMENTS

| | | |
|---|---|---|
| EP | 0 398 230 | 11/1990 |
| EP | 0 507 188 | 10/1992 |

OTHER PUBLICATIONS

International Search Report issued Jun. 2, 2009 in International (PCT) Application No. PCT/JP2009/057362. M. Nomura et al., "Nucleosides and Nucleotides. 185. Synthesis and Biological Activities of 4'α-C-Branched-Chain Sugar Pyrimidine Nucleotides", J. Med. Chem., vol. 42, No. 15, pp. 2901-2908, 1999.

G. H. Jones et al., "4'-Substituted Nucleosides. 5.[1] Hydroxymethylation of Nucleotide 5'-Aldehydes", J. Org. Chem., vol. 44, No. 8, pp. 1309-1317, 1979.
English translation of the International Preliminary Report on Patentability and Written Opinion dated Nov. 30, 2010, PCT/JP2009/057362.
Supplementary European Search Report dated Feb. 27, 2013 in EP Application No. 09731131.0.
M. Mansuri et al., "Preparation of 1-(2,3-Dideoxy-β-D-glycero-pent-2-enofuranosyl)th3rrnine (d4T) and 2', 3'-Dideoxyadenosine (ddA): General Methods for the Synthesis of 2',3'-Olefinic and 2',3'-Dideoxy Nucleoside Analogues Active against HIV", Journal of Organic Chemistry, vol. 54, No. 20, pp. 4780-4785, Sep. 29, 1989.
H. Shiragami et al., "Synthesis of 1-(2,3-Dideoxy-β-D-glycero-pent-2-enofuranosyl)thymine (d4T; Stavudine) from 5- Methyluridine", Nucleosides & Nucleotides, vol. 15, Nos. 1-3, pp. 47-58, Jan. 1, 1996.

* cited by examiner

*Primary Examiner* — Lawrence E Crane
(74) *Attorney, Agent, or Firm* — Wenderoth, Lind & Ponack, L.L.P.

(57) ABSTRACT

The present invention provides a process for producing 2',3'-didehydro-3'-deoxy-4'-ethynylthymidine, which is useful as a medicine, in an efficient and industrially advantageous manner, and more specifically, provides a process for producing 2',3'-didehydro-3'-deoxy-4'-ethynylthymidine as shown below.

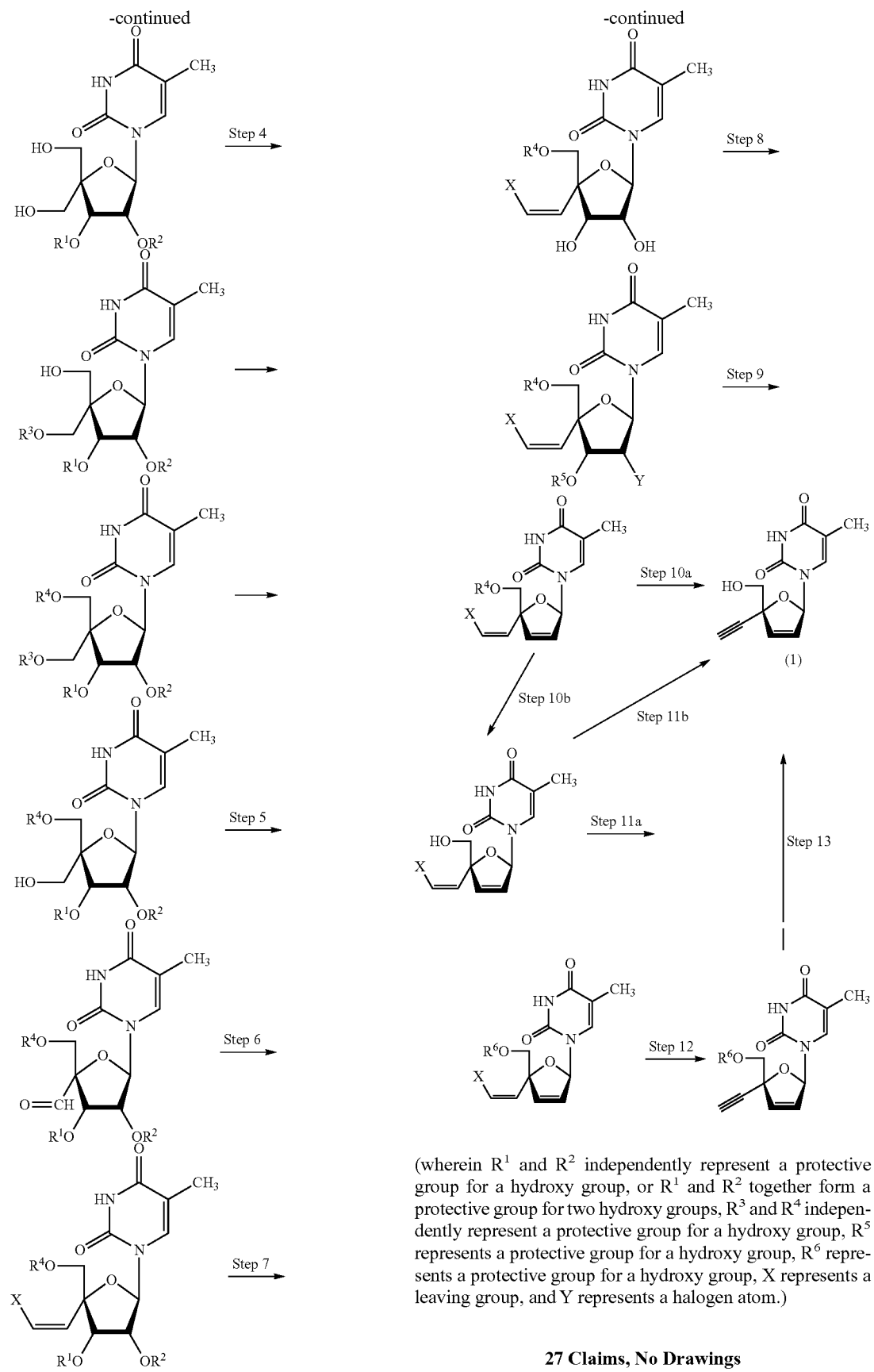

(wherein $R^1$ and $R^2$ independently represent a protective group for a hydroxy group, or $R^1$ and $R^2$ together form a protective group for two hydroxy groups, $R^3$ and $R^4$ independently represent a protective group for a hydroxy group, $R^5$ represents a protective group for a hydroxy group, $R^6$ represents a protective group for a hydroxy group, X represents a leaving group, and Y represents a halogen atom.)

27 Claims, No Drawings

PRODUCTION PROCESS OF ETHYNYLTHYMIDINE COMPOUNDS FROM 5-METHYLURIDINE AS A STARTING MATERIAL

This application is a U.S. national stage of International Application No. PCT/JP2009/057362 filed Apr. 10, 2009.

TECHNICAL FIELD

The present invention relates to a production process of an ethynylthymidine compound useful as a medicine, and more specifically, relates to a production process of 2',3'-didehydro-3'-deoxy-4'-ethynylthymidine.

BACKGROUND ART

2',3'-didehydro-3'-deoxy-4'-ethynylthymidine is the compound represented by the following Formula (1):

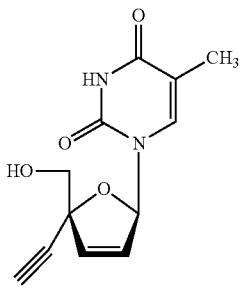

(1)

(hereinafter referred to as Compound (1) or TKD), which is one of nucleoside analogue reverse transcriptase inhibitors (NRTIs). Compound (1) is a medicinal compound useful as a drug for preventing the development of the acquired immunodeficiency syndrome, and is known to have an activity superior to that of the commercially available similar drug Stavudine (2',3'-didehydro-3'-deoxythymidine, d4T).

As the process for synthesizing Compound (1), the following three main types have been reported so far. However, while the 1st and the 2nd synthetic processes produce optically pure Compound (1), the 3rd process produces a racemate. Therefore, only two kinds of processes substantially exist.

The scheme of the 1st synthetic process, which was the first reported route, is as shown below. Thymidine as a starting material is converted into a 4',5'-unsaturated derivative. Next, a 4',5'-epoxy compound or a 4',5'-bisacyloxy compound is synthesized. Then, an organoaluminum compound having an ethynyl group is reacted with the synthesized compound to give an adduct, and further a 2',3'-unsaturated bond is introduced to give Compound (1) (non patent literatures 1, 2, and 3, and patent literatures 1 and 2).

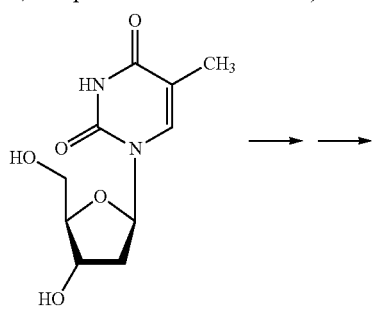

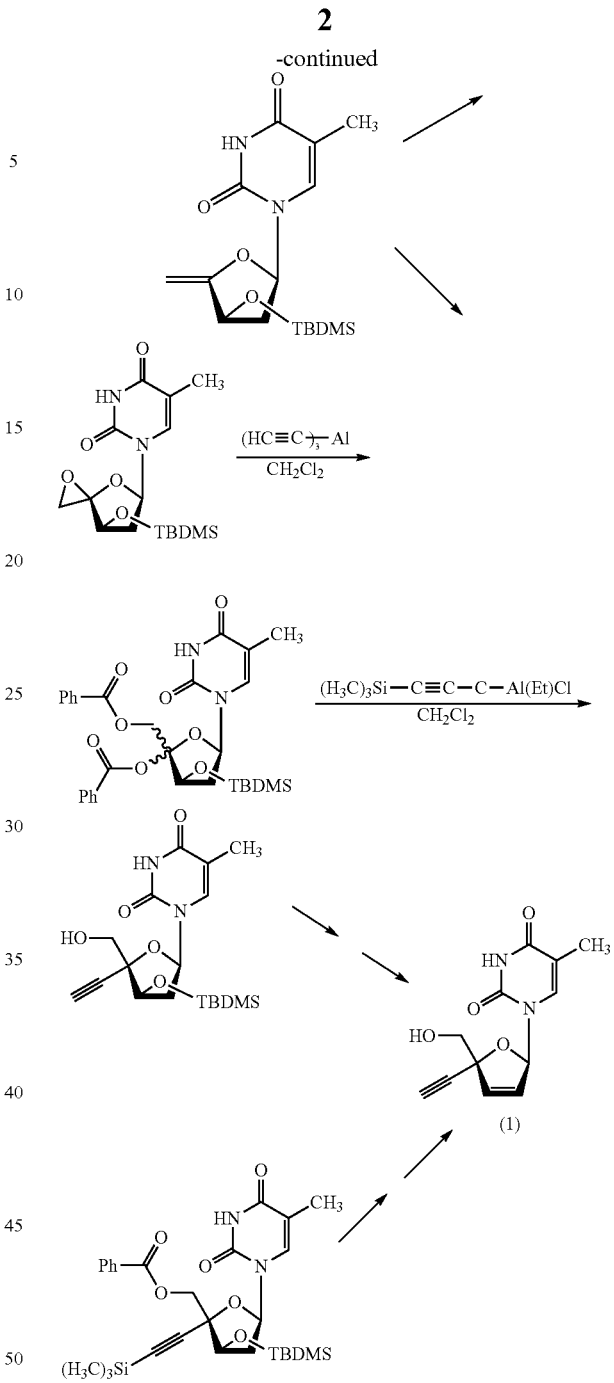

(In the scheme, Ph represents a phenyl group, Et represents an ethyl group, and TBDMS represents a tert-butyldimethylsilyl group.)

The 2nd route is as shown below. Similarly, thymidine is used as a starting material. By replacement of a bulky protecting group, such as a dimethoxytrityl group (DMT group), a tert-butyldimethylsilyl group (TBS or TBDMS group), tert-butyldiphenylsilyl group (TBDPS group), or the like, a hydroxymethyl group is introduced into position 4' and selective protection of the hydroxy group at position 5' is performed. Then, the hydroxymethyl group at position 4' is oxidized into a formyl group and subsequently converted into a chloro ethenyl group by the Wittig reaction. Then, butyl lithium (BuLi) is used to convert the chloro ethenyl group into an ethynyl group. Thus, an ethynyl group is stereoselectively introduced into position 4'. Finally a 2',3'-unsaturated bond is introduced to give Compound (1) (patent literatures 1 and 2).

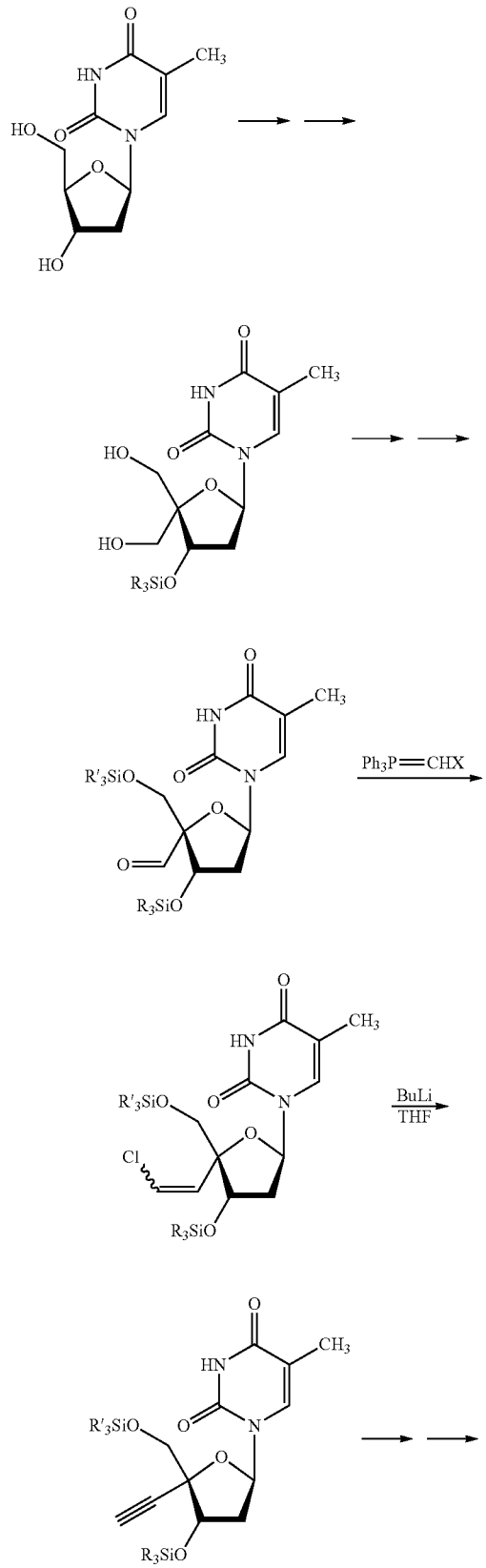

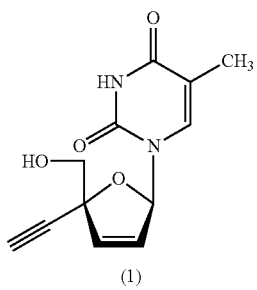 [SMILES: C#C[C@@]1(CO)C=C[C@H](n2cc(C)c(=O)[nH]c2=O)O1]

(1)

(In the scheme, each symbol has the same meaning as defined in the patent literatures 1 and 2.)

The 3rd route is as shown below. Isopropyl acetate as a starting material is converted into a ketoester through several steps. The ketoester is reacted with ethynylmagnesium bromide and thereby converted into propargyl alcohol. The reduction of the ester group to an aldehyde and subsequent lactol ring formation give a furanose derivative. The furanose derivative is condensed with silylated thymine to give a nucleoside (a 1:1 mixture of α- and (β-anomers). After the objective β-anomer is separated, finally a 2',3'-unsaturated bond is introduced to give a racemate [I] (non patent literature 4).

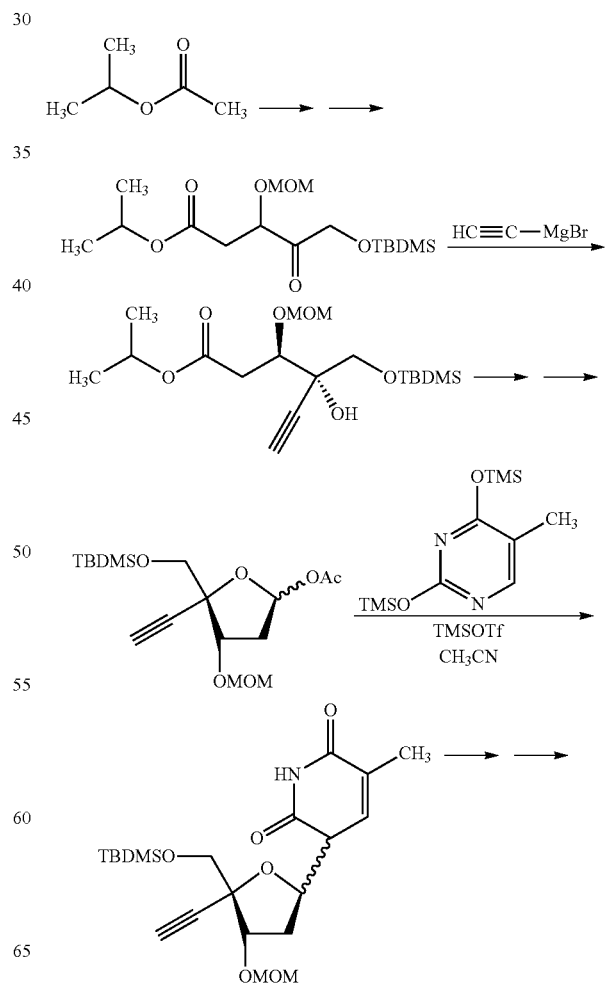

-continued

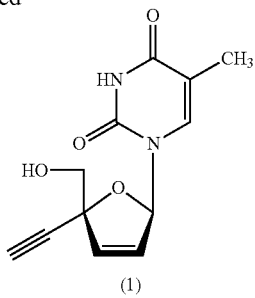

(In the scheme, TBDMS represents a tert-butyldimethylsilyl group, TMS represents a trimethylsilyl group, OTf represents a trifluoromethane sulfonyloxy group, MOM represents a methoxymethyl group, and Ac represents an acetyl group.)

However, the above processes have various problems: since the raw material is expensive, industrial production is difficult due to the high cost; a significant amount of a hazardous or toxic compound or the like is used; and separation or purification of an intermediate having a silyl group as a protective group is difficult because such an intermediate is hard to crystallize.

CITATION LIST

Patent Literature

PTL 1: U.S. Patent Publication No. 2004/0167096
PTL 2: JP-2006-528972 A

Non Patent Literature

NPL 1: K. Haraguchi et al., Bioorg. Med. Chem. Lett., Vol. 13, 3775-3777 (2003)
NPL 2: K. Haraguchi et al., Nucleosides, Nucleotides & Nucleic Acids, Vol. 24, 343-347 (2005)
NPL 3: K. Haraguchi et al., J. Org. Chem., Vol. 71, 4433-4438 (2006)
NPL 4: A. Maddaford et al., Synthesis, 1378-1384 (2007)

SUMMARY OF INVENTION

Technical Problem

An object of the present invention is to provide a production process for chemically synthesizing 2',3'-didehydro-3'-deoxy-4'-ethynylthymidine in an efficient and industrially advantageous manner.

Solution to Problem

The present inventors conducted extensive research to achieve the above-mentioned object and as a result found that the process of the present invention has the following advantages: inexpensive 5-methyluridine is used as the starting material; there is no need for compounds or reagents that may be hazardous or toxic when used in significant quantities, for example, epoxides; each step constituting the production process also proceeds in good yields; and the objective stereoisomer can be obtained in a stereochemically highly selective manner because the process of distinguish a hydroxy group at position 5' from that at position 6' in an intermediate is simple and easy. Based on this finding, the present inventors conducted further research and completed the present invention.

That is, the present invention relates to:
[1] a process for producing 2',3'-didehydro-3'-deoxy-4'-ethynylthymidine represented by the following Formula (1):

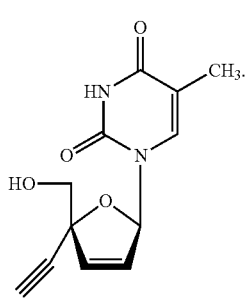

the process comprising the following Steps 1 to 10a,

[Step 1] selectively protecting the hydroxy groups at positions 2' and 3' in the compound represented by the following Formula (2):

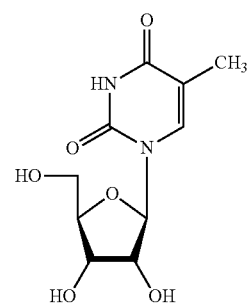

to obtain a compound represented by the following Formula (3):

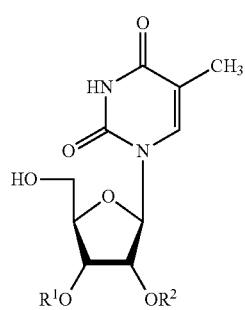

(wherein $R^1$ and $R^2$ independently represent a protective group for a hydroxy group, or $R^1$ and $R^2$ together form a protective group for two hydroxy groups);

[Step 2] oxidizing the hydroxy group at position 5' in the compound represented by the above Formula (3) to obtain a compound represented by the following Formula (4):

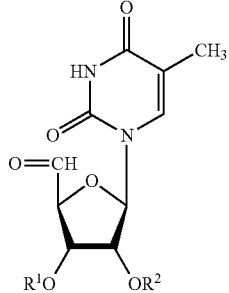

(4)

(wherein $R^1$ and $R^2$ have the same meanings as defined above);

[Step 3] introducing a hydroxymethyl group to position 4' in the compound represented by the above Formula (4) and then performing reduction to obtain a compound represented by the following Formula (5):

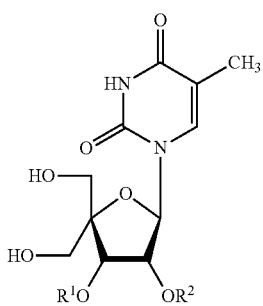

(5)

(wherein $R^1$ and $R^2$ have the same meanings as defined above);

[Step 4] selectively protecting the hydroxy group at position 6' in the compound represented by the above Formula (5) to obtain a compound represented by the following Formula (6):

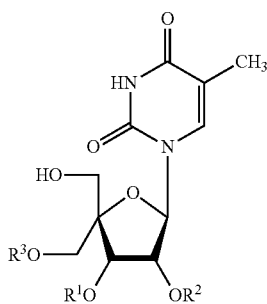

(6)

(wherein $R^1$ and $R^2$ have the same meanings as defined above, and $R^3$ represents a protective group for a hydroxy group), then selectively protecting the hydroxy group at position 5' in the compound represented by the above Formula (6) to obtain a compound represented by the following Formula (7):

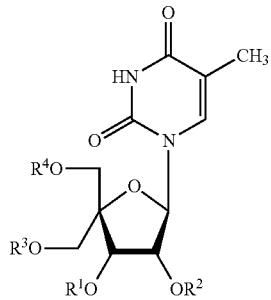

(7)

(wherein $R^1$, $R^2$ and $R^3$ have the same meanings as defined above, and $R^4$ represents a protective group for a hydroxy group), and then selectively removing the protective group of the hydroxy group at position 6' in the compound represented by the above Formula (7) to obtain a compound represented by the following Formula (8):

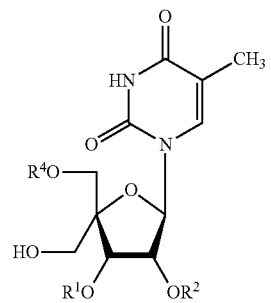

(8)

(wherein $R^1$, $R^2$ and $R^4$ have the same meanings as defined above);

[Step 5] oxidizing the hydroxy group at position 6' in the compound represented by the above Formula (8) to obtain a compound represented by the following Formula (9):

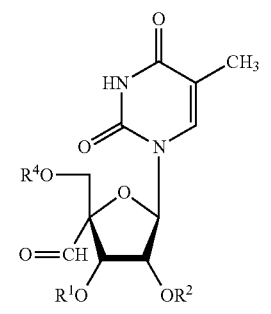

(9)

(wherein $R^1$, $R^2$ and $R^4$ have the same meanings as defined above);

[Step 6] subjecting the compound represented by the above Formula (9) to the Wittig reaction to obtain a compound represented by the following Formula (10):

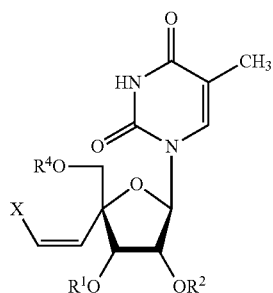

(wherein $R^1$, $R^2$, and $R^4$ have the same meanings as defined above, and X represents a leaving group);

[Step 7] selectively removing the protective groups of the hydroxy groups at positions 2' and 3' in the compound represented by the above Formula (10) to obtain a compound represented by the following Formula (11):

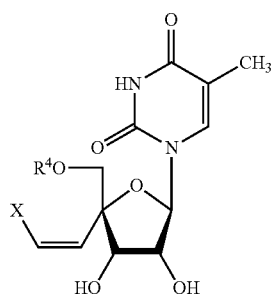

(wherein $R^4$ and X have the same meanings as defined above);

[Step 8] subjecting the compound represented by the above Formula (11) and ortho carboxylic acid ester to an ester exchange reaction and subsequent treatment with an acid halide, to obtain a compound represented by the following Formula (12):

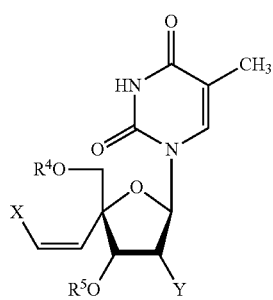

(wherein $R^4$ has the same meaning as defined above, $R^5$ represents a protective group for a hydroxy group, and Y represents a halogen atom);

[Step 9] subjecting the compound represented by the above Formula (12) to a reductive elimination reaction to obtain a compound represented by the following Formula (13):

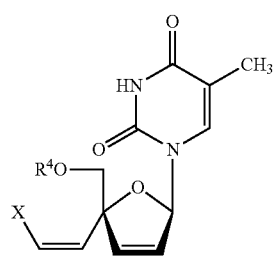

(wherein $R^4$ and X have the same meanings as defined above); and

[Step 10a] treating the compound represented by the above Formula (13) with a base in the presence of a halogenated silane or a compound capable of being a ligand for Lewis acid metals, to obtain 2',3'-didehydro-3-deoxy-4'-ethynylthymidine represented by the above Formula (1);

[2] a process for producing 2',3'-didehydro-3'-deoxy-4'-ethynylthymidine represented by the Formula (1):

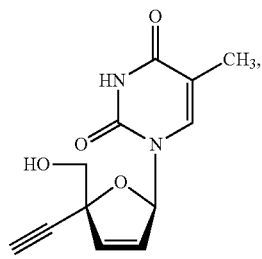

the process comprising the following Steps 1 to 13,

[Step 1] selectively protecting the hydroxy groups at positions 2' and 3' in the compound represented by the following Formula (2):

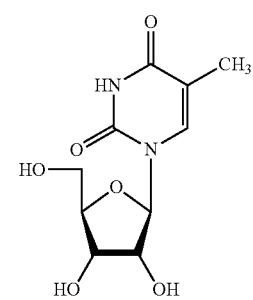

to obtain a compound represented by the following Formula (3):

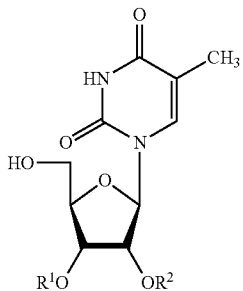

(3)

(wherein R¹ and R² independently represent a protective group for a hydroxy group, or R¹ and R² together form a protective group for two hydroxy groups);

[Step 2] oxidizing the hydroxy group at position 5' in the compound represented by the above Formula (3) to obtain a compound represented by the following Formula (4):

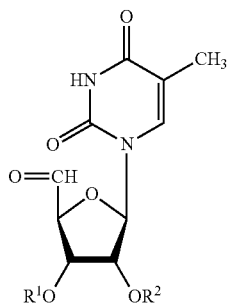

(4)

(wherein R¹ and R² have the same meanings as defined above);

[Step 3] introducing a hydroxymethyl group to position 4' in the compound represented by the above Formula (4) and then performing reduction to obtain a compound represented by the following Formula (5):

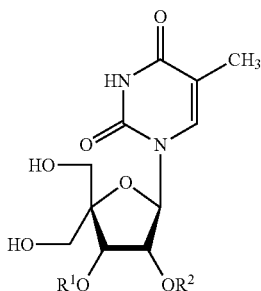

(5)

(wherein R¹ and R² have the same meanings as defined above);

[Step 4] selectively protecting the hydroxy group at position 6' in the compound represented by the above Formula (5) to obtain a compound represented by the following Formula (6):

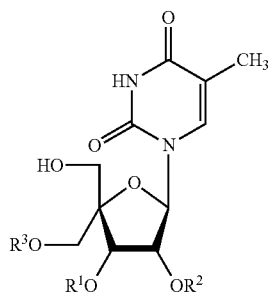

(6)

(wherein R¹ and R² have the same meanings as defined above, and R³ represents a protective group for a hydroxy group), then selectively protecting the hydroxy group at position 5' in the compound represented by the above Formula (6) to obtain a compound represented by the following Formula (7):

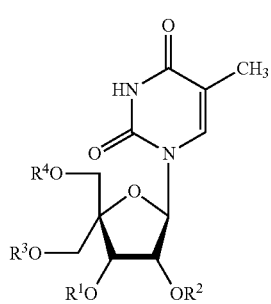

(7)

(wherein R¹, R² and R³ have the same meanings as defined above, and R⁴ represents a protective group for a hydroxy group), and then selectively removing the protective group of the hydroxy group at position 6' in the compound represented by the above Formula (7) to obtain a compound represented by the following Formula (8):

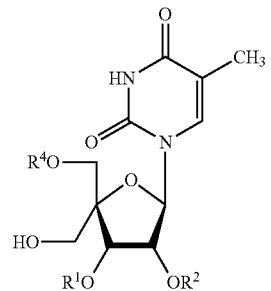

(8)

(wherein R¹, R² and R⁴ have the same meanings as defined above);

[Step 5] oxidizing the hydroxy group at position 6' in the compound represented by the above Formula (8) to obtain a compound represented by the following Formula (9):

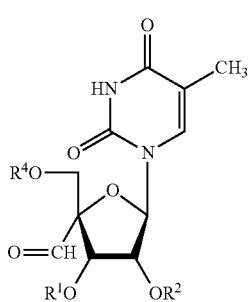

(9)

(wherein $R^1$, $R^2$ and $R^4$ have the same meanings as defined above);

[Step 6] subjecting the compound represented by the above Formula (9) to the Wittig reaction to obtain a compound represented by the following Formula (10):

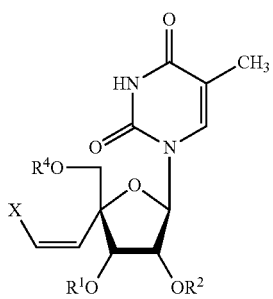

(10)

(wherein $R^1$, $R^2$, and $R^4$ have the same meanings as defined above, and X represents a leaving group);

[Step 7] selectively removing the protective groups of the hydroxy groups at positions 2' and 3' in the compound represented by the above Formula (10) to obtain a compound represented by the following Formula (11):

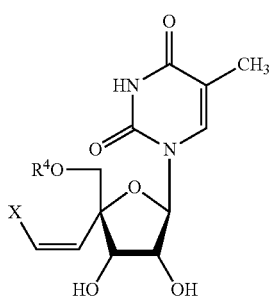

(11)

(wherein $R^4$ and X have the same meanings as defined above);

[Step 8] subjecting the compound represented by the above Formula (11) and ortho carboxylic acid ester to an ester exchange reaction and subsequent treatment with an acid halide, to obtain a compound represented by the following Formula (12):

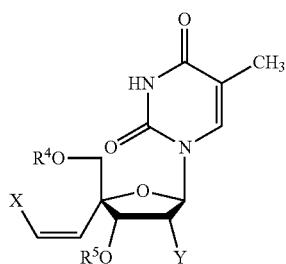

(12)

(wherein $R^4$ has the same meaning as defined above, $R^5$ represents a protective group for a hydroxy group, and Y represents a halogen atom);

[Step 9] subjecting the compound represented by the above Formula (12) to a reductive elimination reaction to obtain a compound represented by the following Formula (13):

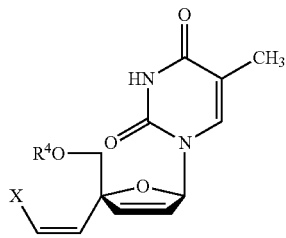

(13)

(wherein $R^4$ and X have the same meanings as defined above);

[Step 10b] selectively removing the protective group of the hydroxy group at position 5' in the compound represented by the above Formula (13) to obtain a compound represented by the following Formula (14):

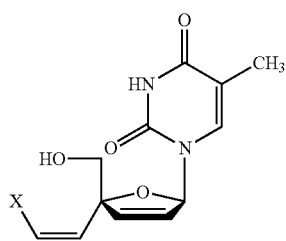

(14)

(wherein X has the same meaning as defined above);

[Step 11a] selectively protecting the hydroxy group at position 5' in the compound represented by the above Formula (14) to obtain a compound represented by the following Formula (15):

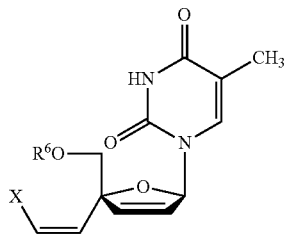

(wherein X has the same meaning as defined above, and $R^6$ represents a protective group for a hydroxy group);

[Step 12] treating the compound represented by the above Formula (15) with a base to obtain a compound represented by the following Formula (16):

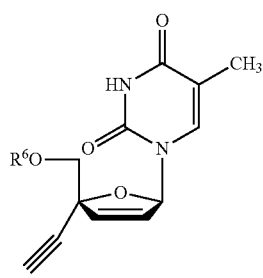

(wherein $R^6$ has the same meaning as defined above); and

[Step 13] selectively removing the protective group of the hydroxy group at position 5' in the compound represented by the above Formula (16) to obtain 2',3'-didehydro-3'-deoxy-4'-ethynylthymidine represented by the above Formula (1);

[3] a process for producing 2',3'-didehydro-3'-deoxy-4'-ethynylthymidine represented by the Formula (1):

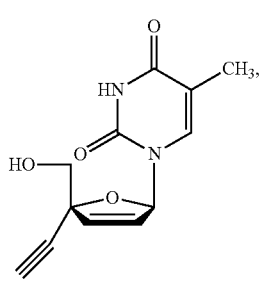

the process comprising the following Steps 1 to 11b,

[Step 1] selectively protecting the hydroxy groups at positions 2' and 3' in the compound represented by the following Formula (2):

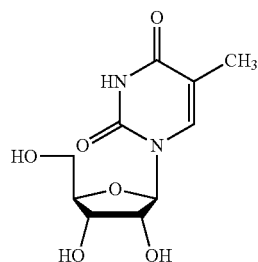

to obtain a compound represented by the following Formula (3):

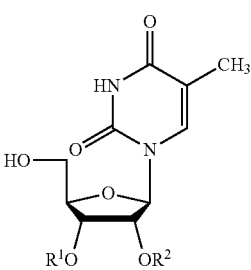

(wherein $R^1$ and $R^2$ independently represent a protective group for a hydroxy group, or $R^1$ and $R^2$ together form a protective group for two hydroxy groups);

[Step 2] oxidizing the hydroxy group at position 5' in the compound represented by the above Formula (3) to obtain a compound represented by the following Formula (4):

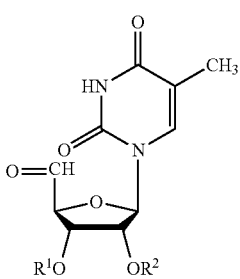

(wherein $R^1$ and $R^2$ have the same meanings as defined above);

[Step 3] introducing a hydroxymethyl group to position 4' in the compound represented by the above Formula (4) and then performing reduction to obtain a compound represented by the following Formula (5):

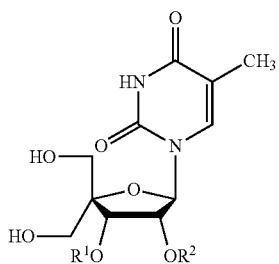

(wherein $R^1$ and $R^2$ have the same meanings as defined above);

[Step 4] selectively protecting the hydroxy group at position 6' in the compound represented by the above Formula (5) to obtain a compound represented by the following Formula (6):

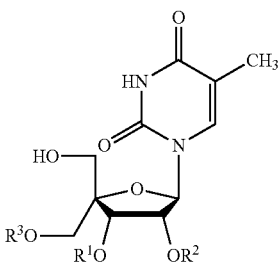

(wherein $R^1$ and $R^2$ have the same meanings as defined above, and $R^3$ represents a protective group for a hydroxy group), then selectively protecting the hydroxy group at position 5' in the compound represented by the above Formula (6) to obtain a compound represented by the following Formula (7):

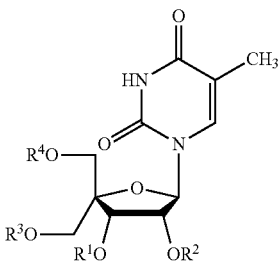

(wherein $R^1$, $R^2$ and $R^3$ have the same meanings as defined above, and $R^4$ represents a protective group for a hydroxy group), and then selectively removing the protective group of the hydroxy group at position 6' in the compound represented by the above Formula (7) to obtain a compound represented by the following Formula (8):

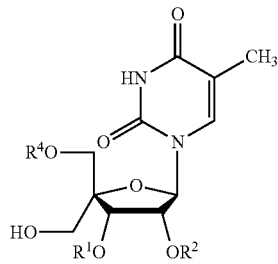

(wherein $R^1$, $R^2$ and $R^4$ have the same meanings as defined above);

[Step 5] oxidizing the hydroxy group at position 6' in the compound represented by the above Formula (8) to obtain a compound represented by the following Formula (9):

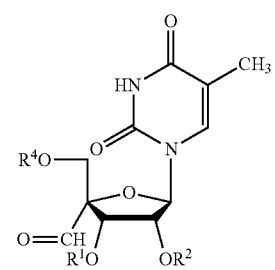

(wherein $R^1$, $R^2$ and $R^4$ have the same meanings as defined above);

[Step 6] subjecting the compound represented by the above Formula (9) to the Wittig reaction to obtain a compound represented by the following Formula (10):

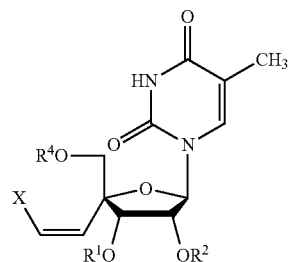

(wherein $R^1$, $R^2$, and $R^4$ have the same meanings as defined above, and X represents a leaving group);

[Step 7] selectively removing the protective groups of the hydroxy groups at positions 2' and 3' in the compound represented by the above Formula (10) to obtain a compound represented by the following Formula (11):

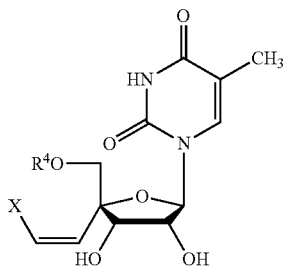

(wherein $R^4$ and X have the same meanings as defined above);

[Step 8] subjecting the compound represented by the above Formula (11) and ortho carboxylic acid ester to an ester exchange reaction and subsequent treatment with an acid halide, to obtain a compound represented by the following Formula (12):

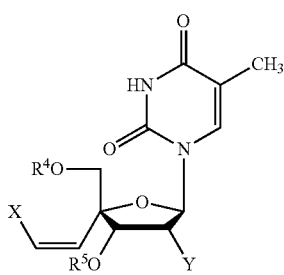

(wherein $R^4$ has the same meaning as defined above, $R^5$ represents a protective group for a hydroxy group, and Y represents a halogen atom);

[Step 9] subjecting the compound represented by the above Formula (12) to a reductive elimination reaction to obtain a compound represented by the following Formula (13):

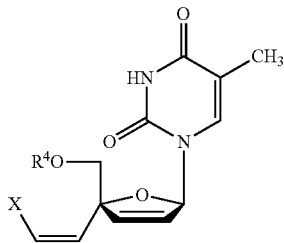

(wherein $R^4$ and X have the same meanings as defined above);

[Step 10b] selectively removing the protective group of the hydroxy group at position 5' in the compound represented by the above Formula (13) to obtain a compound represented by the following Formula (14):

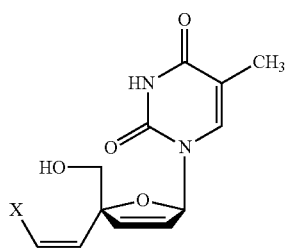

(wherein X has the same meaning as defined above);

[Step 11b] treating the compound represented by the above Formula (14) with a base to obtain 2',3'-didehydro-3'-deoxy-4'-ethynylthymidine represented by the above Formula (1);

[4] the process according to the above [3], wherein $R^6$ is a trityl group or a tetrahydropyranyl group;

[5] the process according to any of the above [1] to [4], wherein $R^1$ and $R^2$ together form an acetal type protective group;

[6] the process according to the above [5], wherein the acetal type protective group is cyclohexylidene;

[7] the process according to any of the above [1] to [6], wherein $R^3$ is a trityl group;

[8] the process according to any of the above [1] to [7], wherein $R^4$ is a pivaloyl group;

[9] the process according to any of the above [1] to [8], wherein X is a chlorine atom;

[10] the process according to any of the above [1] to [9], wherein $R^5$ is an acetyl group;

[11] the process according to any of the above [1] to [10], wherein Y is a bromine atom;

[12] a compound represented by the following Formula (10):

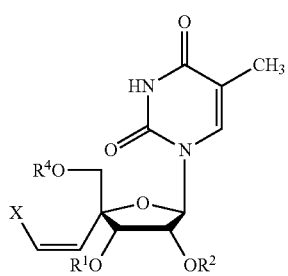

(wherein $R^1$ and $R^2$ independently represent a protective group for a hydroxy group, or $R^1$ and $R^2$ together form a protective group for two hydroxy groups, $R^4$ represents a protective group for a hydroxy group, and X represents a leaving group);

[13] a compound represented by the following Formula (11):

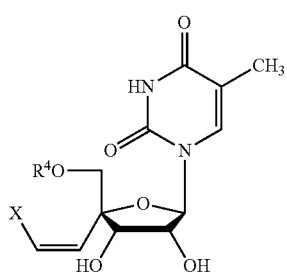

(wherein R⁴ represents a protective group for a hydroxy group, and X represents a leaving group);
[14] the compound according to the above [12] or [13], wherein R⁴ is an optionally substituted straight or branched alkyl group having 1 to 6 carbon atoms, an acyl type protective group, an optionally substituted aralkyloxy carbonyl group, an acyl group, a trityl type protective group, an acetal type protective group, a silyl type protective group, an optionally substituted alkoxycarbonyl group having 2 to 13 carbon atoms, or an optionally substituted aralkyl group having 7 to 20 carbon atoms;
[15] the compound according to the above [12] or [13], wherein R⁴ is a pivaloyl group;
[16] the compound according to any of the above [12] to [15], wherein X is a halogen atom or an optionally substituted alkylsulfonyloxy group having 1 to 4 carbon atoms;
[17] the compound according to any of the above [12] to [15], wherein X is a chlorine atom, a bromine atom, an iodine atom, or a trifluoromethane sulfonyloxy group;
[18] a compound represented by the following Formula (13):

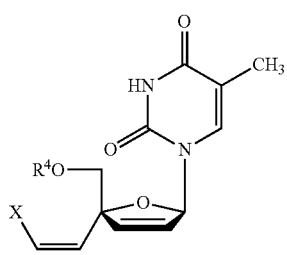

(wherein R⁴ represents a protective group for a hydroxy group, and X represents a leaving group);
[19] the compound according to the above [18], wherein R⁴ is an optionally substituted straight or branched alkyl group having 1 to 6 carbon atoms, an acyl type protective group, an optionally substituted aralkyloxy carbonyl group, an acyl group, a trityl type protective group, an acetal type protective group, a silyl type protective group, an optionally substituted alkoxycarbonyl group having 2 to 13 carbon atoms, or an optionally substituted aralkyl group having 7 to 20 carbon atoms;
[20] the compound according to the above [18], wherein R⁴ is a pivaloyl group, a trityl group, or a tetrahydropyranyl group;
[21] the compound according to any of the above [18] to [20], wherein X is a halogen atom or an optionally substituted alkylsulfonyloxy group having 1 to 4 carbon atoms;
[22] the compound according to any of the above [18] to [20], wherein X is a chlorine atom, a bromine atom, an iodine atom, or a trifluoromethane sulfonyloxy group; and

[23] a compound represented by the following Formula (5):

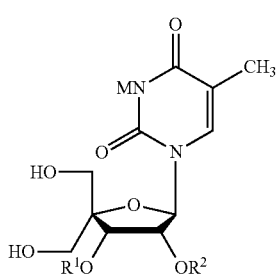

(wherein R¹ and R² independently represent a protective group for a hydroxy group, or R¹ and R² together form a protective group for two hydroxy groups, and M represents a sodium atom or a potassium atom).

Advantageous Effects of Invention

The present invention provides a production process for chemically synthesizing highly pure 2',3'-didehydro-3'-deoxy-4-ethynylthymidine in an efficient and industrially advantageous manner without using purification methods inadequate for large-scale synthesis, such as column chromatography, and an intermediate used in the process.

DESCRIPTION OF EMBODIMENTS

The present invention relates to a process for producing 2',3'-didehydro-3'-deoxy-4'-ethynylthymidine.

Preferred examples of the "protective group for a hydroxy group" represented by R¹ and R² include acetal type protective groups, such as methoxy methyleneacetal, ethoxy methyleneacetal, isopropylidene, cyclohexylidene, cyclopentylidene, methyleneacetal, ethylideneacetal and benzylideneacetal; optionally substituted straight or branched alkyl groups having 1 to 6 carbon atoms, such as methyl, ethyl, n-propyl, iso-propyl, n-butyl, iso-butyl, tert-butyl, n-hexyl, methylthiomethyl, 2,2-trichloroethyl, 1-(2-chloroethoxy)ethyl and methoxymethyl; optionally substituted aralkyloxy carbonyl groups, such as benzyloxycarbonyl; acyl groups, such as acetyl, trichloroacetyl, trifluoroacetyl, benzoyl, naphthoyl and toluoyl; trityl type protective groups, such as dimethoxytrityl (hereafter abbreviated as DMT) and trityl (hereafter abbreviated as Tr); acyl type protective groups, such as pivaloyl and triphenylacetyl; silyl type protective groups, such as trimethylsilyl, triethylsilyl (hereafter abbreviated as TES), tert-butyldimethylsilyl (hereafter abbreviated as TBS or TBDMS), tert-butyldiphenylsilyl (hereafter abbreviated as TBDPS) and triisopropyl silyl (hereafter abbreviated as TIPS); silylene type protective groups, such as dimethylsilylene and di(tert-butyl) silylene; optionally substituted alkoxycarbonyl groups having 2 to 13, preferably 2 to 7 carbon atoms, such as methoxycarbonyl, ethoxycarbonyl, n-propoxycarbonyl, isopropoxycarbonyl and tert-butoxycarbonyl; and optionally substituted aralkyl groups having 7 to 20, preferably 7 to 15 carbon atoms, such as benzyl, p-methoxybenzyl, p-nitrobenzyl, 2-phenylethyl, 1-phenylpropyl, and 3-naphthyl propyl, and these well-established known groups are conveniently used.

From the viewpoint of the stereoselectivity of a reaction, preferred are cyclic acetal type protective groups which $R^1$ and $R^2$ together form, such as methoxy methyleneacetal, ethoxy methyleneacetal, isopropylidene, cyclohexylidene, cyclopentylidene, methyleneacetal, ethylideneacetal, and benzylideneacetal, and isopropylidene and cyclohexylidene are particularly preferred.

Preferred examples of the "protective group for a hydroxy group" represented by $R^3$ include optionally substituted straight or branched alkyl groups having 1 to 6 carbon atoms, such as methyl, ethyl, n-propyl, iso-propyl, n-butyl, iso-butyl, tert-butyl, n-hexyl, methylthiomethyl, 2,2-trichloroethyl, 1-(2-chloroethoxy)ethyl and methoxymethyl; optionally substituted aralkyloxy carbonyl groups, such as benzyloxycarbonyl; acyl groups, such as acetyl, trichloroacetyl, trifluoroacetyl, benzoyl, naphthoyl and toluoyl; trityl type protective groups, such as DMT and Tr; acyl type protective groups, such as pivaloyl and triphenylacetyl; silyl type protective groups, such as trimethylsilyl, TES, TBDMS, TBDPS and TIPS; alkoxycarbonyl groups having 2 to 13, preferably 2 to 7 carbon atoms, such as methoxycarbonyl, ethoxycarbonyl, n-propoxycarbonyl, isopropoxycarbonyl and tert-butoxycarbonyl; and optionally substituted aralkyl groups having 7 to 20, preferably 7 to 15 carbon atoms, such as benzyl, p-methoxybenzyl, p-nitrobenzyl, 2-phenylethyl, 1-phenylpropyl, and 3-naphthyl propyl, and these well-established known groups are conveniently used.

Preferred examples of the "protective group for a hydroxy group" represented by $R^4$ include optionally substituted straight or branched alkyl groups having 1 to 6 carbon atoms, such as methyl, ethyl, n-propyl, iso-propyl, n-butyl, iso-butyl, tert-butyl, n-hexyl, methylthiomethyl, 2,2-trichloroethyl, 1-(2-chloroethoxy)ethyl and methoxymethyl; optionally substituted aralkyloxy carbonyl groups, such as benzyloxycarbonyl; acyl groups, such as acetyl, trichloroacetyl, trifluoroacetyl, benzoyl, naphthoyl and toluoyl; trityl type protective groups, such as DMT and Tr; acetal type protective groups having a cyclic structure, such as tetrahydropyranyl (hereafter abbreviated as THP) and tetrahydrofuranyl; acyl type protective groups, such as pivaloyl and triphenylacetyl; silyl type protective groups, such as trimethylsilyl, TES, TBDMS, TBDPS and TIPS; alkoxycarbonyl groups having 2 to 13, preferably 2 to 7 carbon atoms, such as methoxycarbonyl, ethoxycarbonyl, n-propoxycarbonyl, isopropoxycarbonyl and tert-butoxycarbonyl; and optionally substituted aralkyl groups having 7 to 20, preferably 7 to 15 carbon atoms, such as benzyl, p-methoxybenzyl, p-nitrobenzyl, 2-phenylethyl, 1-phenylpropyl, and 3-naphthyl propyl, and these well-established known groups are conveniently used.

Preferred examples of the "leaving group" represented by X include halogen atoms such as chlorine, bromine and iodine; optionally substituted alkylsulfonyloxy groups having 1 to 4 carbon atoms, such as methane sulfonyloxy, ethane sulfonyloxy, butane sulfonyloxy, and trifluoromethane sulfonyloxy; optionally substituted arylsulfonyloxy groups having 6 to 10 carbon atoms, such as benzene sulfonyloxy, p-toluenesulfonyloxy, p-bromobenzene sulfonyloxy, and mesitylene sulfonyloxy; alkylthio groups having 1 to 4 carbon atoms, such as methylthio and ethylthio; alkyl sulfinyl groups having 1 to 4 carbon atoms, such as methylsulfinyl; alkyl sulfonyl groups having 1 to 4 carbon atoms, such as methylsulfonyl; arylthio groups having 6 to 10 carbon atoms and optionally having 1 or 2 nitrogen or other substituents, such as phenylthio and p-nitro phenylthio; optionally substituted aralkyl thio groups having 7 to 12 carbon atoms, such as benzylthio and p-nitrobenzyl thio; optionally substituted aralkyl sulfinyl groups having 7 to 12 carbon atoms, such as benzylsulfinyl and p-nitrobenzyl sulfinyl; optionally substituted aralkyl sulfonyl groups having 7 to 12 carbon atoms, such as benzylsulfonyl and p-nitrobenzyl sulfonyl; heterocyclic thio groups, such as 2-pyridylthio and 2-benzothiazolylthio; heterocyclic sulfinyl groups, such as 2-pyridyl sulfinyl; and heterocyclic sulfonyl groups, such as 2-pyridyl sulfonyl, and these well-established known groups are conveniently used.

Particularly preferred examples of the "protective group for a hydroxy group" represented by $R^5$ include aliphatic acyl groups having 1 to 6 carbon atoms, such as formyl, acetyl, propanoyl, butanoyl, pentanoyl and hexanoyl; and aroyl groups, such as benzoyl and toluoyl.

Preferred examples of the "protective group for a hydroxy group" represented by $R^6$ include optionally substituted straight or branched alkyl groups having 1 to 6 carbon atoms, such as methyl, ethyl, n-propyl, iso-propyl, n-butyl, iso-butyl, tert-butyl, n-hexyl, methylthiomethyl, 2,2,2-trichloroethyl, 1-(2-chloroethoxy)ethyl, methoxymethyl, 1-ethoxyethyl, 1-methyl-1-methoxyethyl and 1-methyl-1-benzyloxymethyl; trityl type protective groups, such as DMT and Tr; acetal type protective groups having a cyclic structure, such as tetrahydropyranyl (THP) and tetrahydrofuranyl; silyl type protective groups, such as trimethylsilyl, TES, TBDMS, TBDPS and TIPS; and optionally substituted aralkyl groups having 7 to 20, preferably 7 to 15 carbon atoms, such as benzyl, p-methoxybenzyl, p-nitrobenzyl, 2-phenylethyl, 1-phenylpropyl, and 3-naphthyl propyl, and these well-established known groups are conveniently used.

Examples of the halogen atom represented by Y include chlorine, bromine and iodine, and chlorine and bromine are preferred.

The above-mentioned substituent is not particularly limited as long as the substituent does not disturb the reaction in each step, and examples of the substituent include halogen atoms, such as chloro, bromo, iodo and fluoro; alkyl halide groups having 1 to 6 carbon atoms, such as chloromethyl, 2-chloroethyl, 3-chloroethyl, and trifluoromethyl; nitro; alkyl groups having 1 to 6 carbon atoms, such as methyl, ethyl, n-propyl, isopropyl, isobutyl, sec-butyl, tert-butyl, n-butyl, isopentyl, neopentyl, tert-pentyl, n-pentyl, isohexyl, and n-hexyl; alkoxy groups having 1 to 6 carbon atoms, such as methoxy, ethoxy, n-propyloxy, n-butoxy and n-hexyloxy; cyano; phenoxy; amino; alkanoyl amino groups having 2 to 6 carbon atoms, such as acetylamino, propionylamino, butanoylamino and pentanoyl amino; benzoylamino; hydroxyl; alkoxy carboxyl groups having 2 to 6 carbon atoms, such as methoxycarbonyl, ethoxycarbonyl, n-propyloxy carbonyl, n-butoxycarbonyl and n-hexyloxy carbonyl; phenoxy carbonyl; alkylamino carbonyl groups having 2 to 6 carbon atoms, such as methylamino carbonyl, ethylamino carbonyl, n-propylamino carbonyl, n-butylamino carbonyl and n-hexylamino carbonyl; phenylamino carbonyl; alkylamino sulfonyl groups having 1 to 6 carbon atoms, such as methylamino sulfonyl, ethylamino sulfonyl, n-propylamino sulfonyl, n-butylamino sulfonyl, n-propylamino sulfonyl, and n-hexylamino sulfonyl; and alkenyl groups having 2 to 6 carbon atoms, such as vinyl and allyl.

The production process of the present invention follows the reaction scheme below.

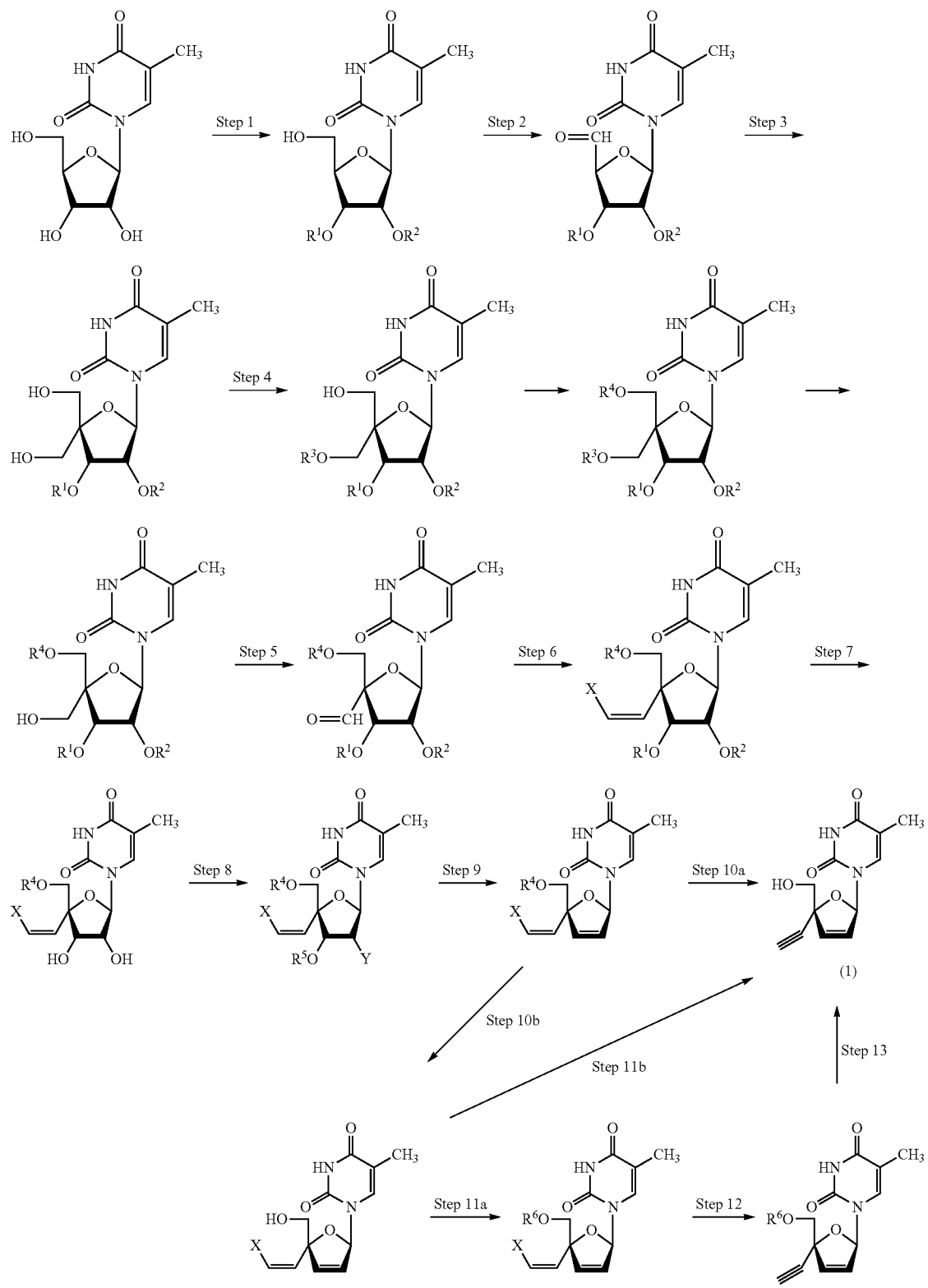

(wherein $R^1$ and $R^2$ independently represent a protective group for a hydroxy group, or $R^1$ and $R^2$ together form a protective group for two hydroxy groups, $R^3$ and $R^4$ independently represent a protective group for a hydroxy group, $R^5$ represents a protective group for a hydroxy group, $R^6$ represents a protective group for a hydroxy group, X represents a leaving group, and Y represents a halogen atom.)

A first embodiment of the production process of the present invention is represented by the reaction scheme below.

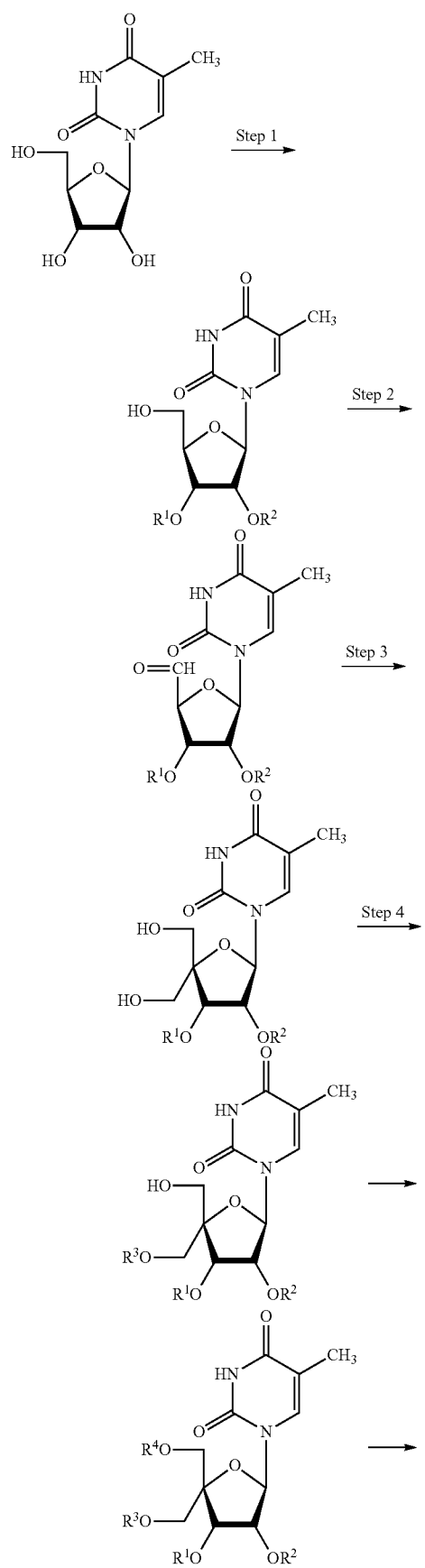
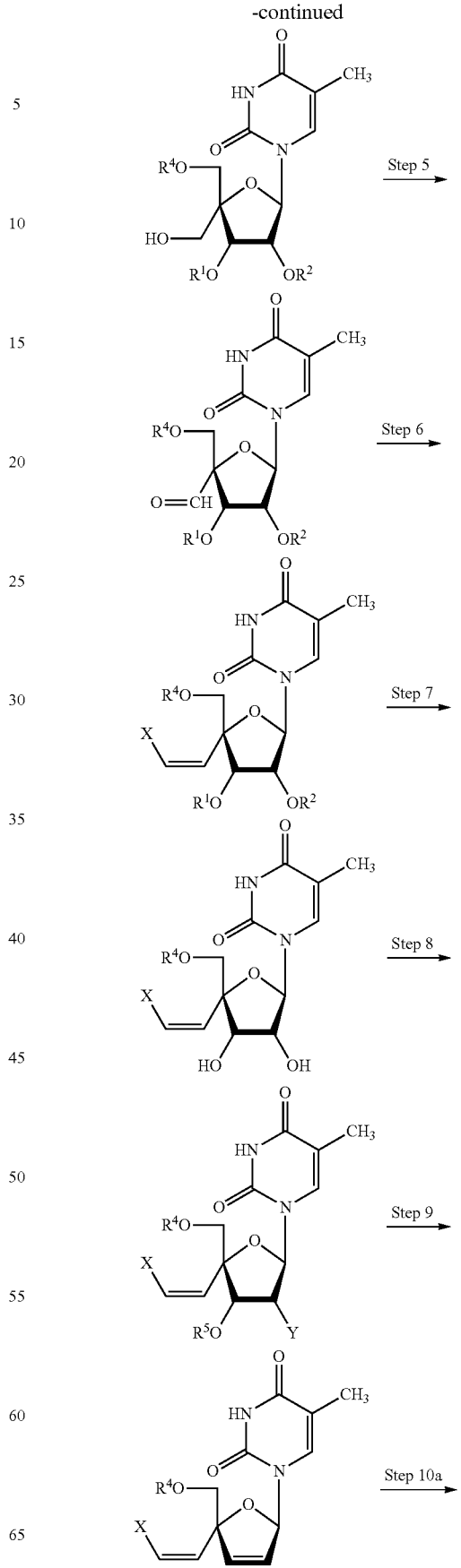

-continued

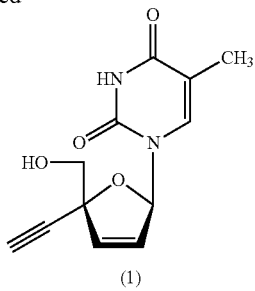

(wherein each symbol has the same meaning as defined above.)

Hereinafter, each step in the first embodiment of the present invention will be described. Position numbering in compounds of the present invention is based on that in an ordinary nucleoside. For clearer understanding, numbers are specified in the following formula.

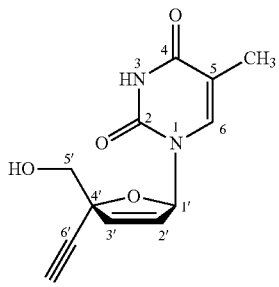 [SMILES: C#C[C@@]1(CO)C=C[C@H](n2cc(C)c(=O)[nH]c2=O)O1]

[Step 1]
5-methyluridine represented by the following Formula (2):

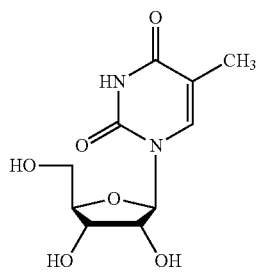

(hereinafter referred to as Compound (2)), which is a starting material of the present invention, can be synthesized according to the process described in JP-A 2002-345497 or JP-A 2002-95494, for example, or is commercially available from Aldrich.

In Step 1, the compound represented by Formula (3) (hereinafter referred to as Compound (3)) can be obtained by selective protection of the hydroxy groups at positions 2' and 3' of Compound (2) with a protective group. Specifically, Compound (3) can be obtained by a condensation reaction of Compound (2) with a protecting agent, preferably in the presence of an acid catalyst.

Examples of the acid catalyst include hydrochloric acid, sulfuric acid, methanesulfonic acid, p-toluenesulfonic acid, camphorsulfonic acid, trifluoromethanesulfonic acid, a boron trifluoride-diethyl ether complex and pyridinium p-toluenesulfonate (hereinafter abbreviated as PPTS). The amount of the acid catalyst is usually about 0.01 to 1 mol, and preferably about 0.01 to 0.5 mol per mole of Compound (2).

Preferable examples of the protecting agent include acid halides such as acetyl chloride, trimethylacetyl chloride (pivaloyl chloride), benzoyl chloride, p-nitrobenzoyl chloride, benzyloxycarbonyl chloride and allyloxycarbonyl chloride, and bromides and iodides corresponding to these chlorides; alkyl halide compounds such as methoxymethyl chloride, benzyl chloride, benzyl bromide and p-methoxybenzyl chloride; aldehyde compounds such as benzaldehyde, and ketone compounds such as acetone, cyclopentanone and cyclohexanone; silyl compounds such as trimethylsilyl chloride, tert-butyldimethylsilyl chloride and di-tert-butylsilyl dichloride; ortho carboxylic acid esters such as trimethyl orthoacetate and triethyl orthoacetate; and acetal compounds such as acetone dimethyl acetal, acetone diethyl acetal, aminoacetaldehyde dimethyl acetal, cyclohexanone dimethyl acetal, cyclopentanone dimethyl acetal and benzaldehyde dimethyl acetal.

Any reaction solvent that does not disturb the reaction concerned can be preferably used, and examples thereof include ketone solvents (for example, methyl ethyl ketone etc.), ether solvents (for example, 1,2-dimethoxyethane (DME), tetrahydrofuran (THF), etc.), nitrile compounds (for example, acetonitrile, propionitrile, benzonitrile, etc.), aromatic organic solvents (for example, benzene, toluene, xylene, etc.), halogenated solvents (for example, dichloromethane, chloroform, etc.), hydrocarbon solvents (hexane, heptane, octane), dimethyl sulfoxide (DMSO), N,N-dimethylformamide (DMF), N,N-dimethylacetamide (DMA) and ethyl acetate. These solvents may be used alone or as a mixture of two or more kinds thereof. The amount of the solvent is usually about 1 to 100 fold, and preferably about 1.5 to 12 fold relative to that of Compound (2) in terms of weight.

The reaction temperature is usually about −20 to 120° C., and preferably about 40 to 80° C. The reaction duration is not particularly limited, and in such a temperature range, usually about 10 minutes to about 24 hours, and preferably about 30 minutes to about 2 hours. An example of Compound (3) obtainable in Step 1 is 2',3'-O-cyclohexylidene-5-methyluridine represented by Formula (3-1):

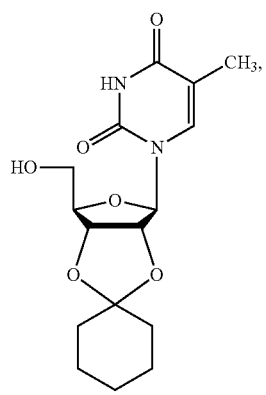

or the like.

[Step 2]
In Step 2, the compound represented by Formula (4) (hereinafter referred to as Compound (4)) can be obtained by oxidation of the hydroxy group at position 5' of Compound (3). Specifically, Compound (4) can be obtained by mixing of Compound (3) with an oxidizing agent in a solvent, for example. These materials may be added in any order without particular limitation.

Examples of the oxidizing agent include organic oxidizers such as 2,3-dichloro-5,6-dicyano-p-benzoquinone, chloranil, bromanil, 1,4-diphenoquinone, tetramethyldiphenoquinone, tetracyanoquinodimethane, tetracyanoethylene and thionyl chloride; organic peroxides such as perbenzoic acid, m-chloroperbenzoic acid and benzoyl peroxide; lead tetraacetate; thallium triacetate; cerium(IV); vanadium pentoxide; magnesium monoperoxyphthalate; potassium peroxymonosulfate; and dimethyl sulfoxide (DMSO). Dimethyl sulfoxide is preferred. In the case where the oxidizing agent is used, an activating agent is preferably used together with the oxidizing agent.

Examples of the activating agent include carbodiimide compounds such as N-ethyl-N'-(3-dimethylaminopropyl)carbodiimide hydrochloride (hereinafter abbreviated as WSC.HCl), N,N'-dicyclohexylcarbodiimide and N,N'-diisopropylcarbodiimide; carboxylic acid halides such as acetyl chloride, acetyl bromide, acetyl iodide, propionyl chloride, butyryl chloride and butyryl bromide; sulfur trioxide derivatives such as a sulfur trioxide-amine complex (for example, pyridine-sulfur trioxide etc.) and a sulfur trioxide-N,N-dimethylformamide (DMF) complex; oxalyl chloride; trifluoroacetic anhydride; acetic anhydride; methanesulfonic acid; p-toluenesulfonic acid; camphorsulfonic acid; trifluoromethanesulfonic acid; a boron trifluoride-diethyl ether complex; acetic acid; dichloroacetic acid; trifluoroacetic acid; and PPTS. WSC.HCl or PPTS is preferred. These activating agents may be used alone or as a mixture of two or more kinds thereof. The amount of the oxidizing agent is usually about 1 to 10 mol, and preferably about 1 to 5 mol per mole of Compound (3). The amount of the activating agent is usually about 1 to 10 mol, and preferably about 1 to 5 mol per mole of Compound (3).

Any reaction solvent that does not disturb the reaction concerned can be preferably used, and examples thereof include ketone solvents (for example, methyl ethyl ketone etc.), ether solvents (for example, DME, THF, etc.), nitrile compounds (for example, acetonitrile, propionitrile, benzonitrile, etc.), aromatic organic solvents (for example, benzene, toluene, xylene, etc.), halogenated solvents (for example, dichloromethane, chloroform, etc.), hydrocarbon solvents (hexane, heptane, octane), dimethyl sulfoxide, DMF, DMA and ethyl acetate. These solvents may be used alone or as a mixture of two or more kinds thereof. In the case where dimethyl sulfoxide (DMSO) is used as the oxidizing agent, DMSO can serve as the solvent as well, and one or more kinds of solvents set forth above may be used in addition to DMSO as long as the solvents do not disturb the oxidation reaction. The amount of the solvent is usually about 1 to 100 fold, and preferably about 1.5 to 12 fold relative to that of Compound (3) in terms of weight.

The reaction temperature is usually about −70 to 80° C., and preferably about 20 to 60° C. The reaction duration is not particularly limited, and in such a temperature range, usually about 10 minutes to about 24 hours, and preferably about 30 minutes to about 2 hours. An example of Compound (4) obtainable in Step 2 is 2',3'-O-cyclohexylidene-5-methyluridine 5'-aldehyde represented by Formula (4-1):

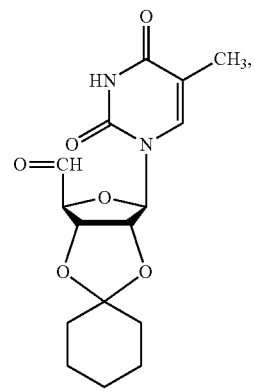

(4-1)

or the like.

[Step 3]

In Step 3, the compound represented by Formula (5) (hereinafter referred to as Compound (5)) can be obtained by introduction of a hydroxymethyl group to position 4' of Compound (4) and subsequent reduction of the formyl group at position 4', preferably using a reducing agent. Specifically, Compound (5) can be obtained by treatment of Compound (4) with a base in the presence of formalin, preferably in a solvent, for introduction of a hydroxymethyl group to position 4' of Compound (4), and then reduction of the formyl group at position 4', preferably with a hydride reducing agent.

Examples of the base include tertiary amines such as triethylamine, tributylamine, ethyldiisopropylamine, tetramethylenediamine and pyridine; and alkali metal hydroxides such as lithium hydroxide, sodium hydroxide and potassium hydroxide. Triethylamine is preferred. The amount of the base is usually about 1 to 15 mol, and preferably about 1 to 8 mol per mole of Compound (4).

The amount of formalin is usually about 1 to 100 fold, and preferably about 1.5 to 12 fold relative to that of Compound (4) in terms of weight.

Any reaction solvent that does not disturb the reaction concerned can be preferably used, and examples thereof include ketone solvents (for example, methyl ethyl ketone etc.), ether solvents (for example, DME, THF, etc.), nitrile compounds (for example, acetonitrile, propionitrile, benzonitrile, etc.), aromatic organic solvents (for example, benzene, toluene, xylene, etc.), halogenated solvents (for example, dichloromethane, chloroform, etc.), hydrocarbon solvents (hexane, heptane, octane), DMSO, DMF, DMA and ethyl acetate. These solvents may be used alone or as a mixture of two or more kinds thereof. The amount of the solvent is usually about 1 to 100 fold, and preferably about 1.5 to 12 fold relative to that of Compound (4) in terms of weight.

The temperature for the base treatment is usually about −20 to 80° C., and preferably about 10 to 50° C. The duration of the base treatment is not particularly limited, and in such a temperature range, usually about 10 minutes to about 24 hours, and preferably about 30 minutes to about 2 hours.

Examples of the hydride reducing agent include sodium borohydride, sodium cyanoborohydride, lithium triethylborohydride, lithium tri-sec-butylborohydride, potassium tri-sec-butylborohydride, lithium borohydride, zinc borohydride, sodium acetoxyborohydride and lithium aluminium hydride.

The temperature for the reducing reaction is usually about −70 to 80° C., and preferably about −10 to 30° C. The reaction duration is not particularly limited, and in such a temperature range, usually about 10 minutes to about 24 hours, and preferably about 30 minutes to about 2 hours. An example of Compound (5) obtainable in Step 3 is 2',3'-O-cyclohexylidene-4'-C-hydroxymethyl-5-methyluridine represented by Formula (5-1):

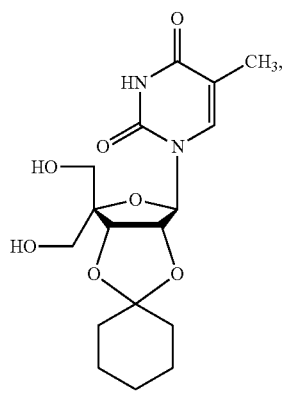

or the like.

Optionally, Compound (5) obtained in Step 3 may be subjected to the following treatment for purification.

In the treatment for purification, Compound (5) obtained in Step 3 is converted into a sodium or potassium salt thereof. Thereby, impurities can be removed from Compound (5) and Compound (5) with high purity can be obtained.

Specifically, a sodium or potassium salt of Compound (5) can be obtained by contact of Compound (5) with an alkali metal base, such as sodium methoxide, potassium methoxide, sodium ethoxide, potassium ethoxide, sodium tert-butoxide, potassium tert-butoxide, potassium hydroxide and sodium hydroxide, in a solvent.

The amount of the alkali metal base is usually about 0.3 to 5 mol, and preferably about 0.8 to 1.5 mol per mole of Compound (5).

Any reaction solvent that does not disturb the reaction concerned can be preferably used, and examples thereof include ketone solvents (for example, acetone, methyl ethyl ketone, etc.), nitrile compounds (for example, acetonitrile, propionitrile, benzonitrile, etc.), ester solvents (for example, ethyl acetate, isopropyl acetate, etc.) and ether solvents (for example, DME, THF, etc.). Inter alia, ketone solvents, nitrile compounds or ester solvents are preferred, and acetonitrile, acetone or isopropyl acetate is more preferred. These solvents may be used alone or as a mixture of two or more kinds thereof.

The amount of the solvent is usually about 1 to 30 fold, and preferably about 5 to 15 fold relative to that of Compound (5) in terms of weight.

The reaction temperature is usually about 10 to 60° C., and preferably about 20 to 30° C. The reaction duration is not particularly limited, and in such a temperature range, usually about 10 seconds to about 12 hours, and preferably about 1 minute to about 2 hours.

After the treatment for purification, methods known per se (for example, salting out, filtration, washing, desiccation, etc.) give a highly pure crystal of Compound (5). All these procedures can be performed under normal, reduced or increased pressure, in an atmosphere of air or inert gas.

Such a purification step via the production of a sodium or potassium salt allows impurities to be efficiently removed from Compound (5) and thereby a highly pure Compound (5) to be obtained.

An example of the impurities removable at Step 3-1 is CMTE (2',3'-O-cyclohexylidene-5-methyl-5'-O-(methylthiomethyl)-uridine) represented by the following Formula (3-2):

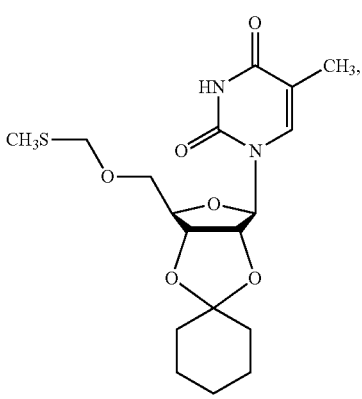

or the like.

[Step 4]

In Step 4, first, selective protection of the hydroxy group at position 6' of Compound (5) gives the compound represented by Formula (6) (hereinafter referred to as Compound (6)). Then, selective protection of the hydroxy group at position 5' of Compound (6) gives the compound represented by Formula (7) (hereinafter referred to as Compound (7)). Finally, the protective group of the hydroxy group at position 6' of Compound (7) is selectively removed, and thereby the compound represented by Formula (8) (hereinafter referred to as Compound (8)) can be obtained. Hereinafter, each of these three stages of Step 4 will be illustrated in more detail.

[Step 4-1]

The compound represented by Formula (6) (hereinafter referred to as Compound (6)) is obtained by selective protection of the hydroxy group at position 6' of Compound (5). Specifically, Compound (6) can be obtained by a condensation reaction of Compound (5) with a protecting agent, preferably in the presence of a base catalyst.

Examples of the base catalyst include 4-(dimethylamino) pyridine (hereinafter abbreviated as DMAP), 1,8-diazabicyclo[5.4.0]undec-7-ene (DBU), 1,5-diazabicyclo[4.3.0]non-5-ene (DBN), 2,6-lutidine, 2,4,6-collidine, 2,3,5-collidine, 2-picoline, 3-picoline and 4-picoline. The amount of the base catalyst is usually about 0.01 to 1 mol, and preferably about 0.01 to 0.5 mol per mole of Compound (5). An auxiliary base may be present in this reaction. Examples of the auxiliary base include tertiary amines such as triethylamine, tributylamine, ethyldiisopropylamine, tetramethylenediamine and pyridine. Triethylamine is preferred. The amount of the auxiliary base is usually about 1 to 10 mol, and preferably about 1 to 5 mol per mole of Compound (5).

Preferable examples of the protecting agent include halogenated triphenylmethanes, such as chlorotriphenylmethane (trityl chloride) and bromotriphenylmethane.

Any reaction solvent that does not disturb the reaction concerned can be preferably used, and examples thereof include ketone solvents (for example, methyl ethyl ketone etc.), ether solvents (for example, DME, THF, etc.), nitrile compounds (for example, acetonitrile, propionitrile, benzonitrile, etc.), aromatic organic solvents (for example, benzene, toluene, xylene, etc.), halogenated solvents (for example, dichloromethane, chloroform, etc.), hydrocarbon solvents (hexane, heptane, octane), DMSO, DMF, DMA and ethyl acetate. These solvents may be used alone or as a mixture of two or more kinds thereof. The amount of the solvent is usually about 1 to 100 fold, and preferably about 3 to 30 fold relative to that of Compound (5) in terms of weight.

The reaction temperature is usually about 0 to 100° C., and preferably about 10 to 50° C. The reaction duration is not particularly limited, and in such a temperature range, usually about 10 minutes to about 24 hours, and preferably about 5 to 20 hours. An example of Compound (6) obtainable in Step 4-1 is 2',3'-O-cyclohexylidene-5-methyl-4'-C-[(trityl)oxymethyl]-uridine represented by Formula (6-1):

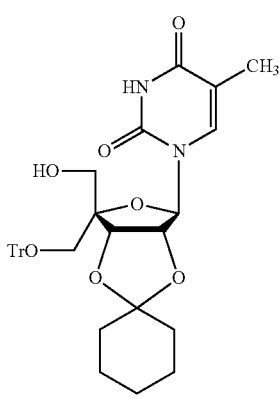

(6-1)

(wherein Tr represents a trityl group), or the like.

[Step 4-2]

The compound represented by Formula (7) (hereinafter referred to as Compound (7)) is obtained by selective protection of the hydroxy group at position 5' of Compound (6). Specifically, Compound (7) can be obtained by a condensation reaction of Compound (6) with a protecting agent, preferably in the presence of a base catalyst.

Preferable examples of the protecting agent include acylating agents, such as trimethylacetyl chloride (pivaloyl chloride) and trimethylacetic anhydride.

Any reaction solvent that does not disturb the reaction concerned can be preferably used, and examples thereof include ketone solvents (for example, methyl ethyl ketone etc.), ether solvents (for example, DME, THF, etc.), nitrile compounds (for example, acetonitrile, propionitrile, benzonitrile, etc.) aromatic organic solvents (for example, benzene, toluene, xylene, etc.), halogenated solvents (for example, dichloromethane, chloroform, etc.), hydrocarbon solvents (hexane, heptane, octane), DMSO, DMF, DMA and ethyl acetate. These solvents may be used alone or as a mixture of two or more kinds thereof. The amount of the solvent is usually about 1 to 100 fold, and preferably about 2 to 15 fold relative to that of Compound (5) in terms of weight.

The reaction temperature is usually about −20 to 100° C., and preferably about 10 to 50° C. The reaction duration is not particularly limited, and in such a temperature range, usually about 10 minutes to about 24 hours, and preferably about 2 to 8 hours. An example of Compound (7) obtainable in Step 4-2 is 2',3'-O-cyclohexylidene-5-methyl-5'-O-pivaloyl-4'-C-[(trityl)oxymethyl]uridine represented by Formula (7-1):

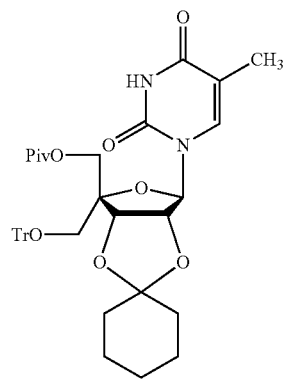

(7-1)

(wherein Tr has the same meaning as defined above and Piv represents a pivaloyl group), or the like.

[Step 4-3]

The compound represented by Formula (8) (hereinafter referred to as Compound (8)) can be obtained by selective deprotection of (selective removal of the protective group from) the hydroxy group at position 6' of Compound (7).

For the deprotection of the hydroxy group at position 6' of Compound (7), depending on the kind of the protective group, an appropriate method may be selected from a method using an acid and a method using catalytic reduction. In the case of the method using an acid, the acid to be used varies with the kind of the protective group and other conditions, and examples thereof include inorganic acids such as hydrochloric acid, hydrogen bromide, hydrogen fluoride, hydrogen iodide, methanesulfonic acid, p-toluenesulfonic acid (tosyl acid), camphorsulfonic acid, trifluoromethanesulfonic acid, sulfuric acid and phosphoric acid; organic acids such as formic acid, acetic acid and trifluoroacetic acid; and acidic ion exchange resins. In the case where a solvent is used in the method using an acid, for example, water, methanol, ethanol, ethyl acetate, chloroform, tetrahydrofuran, dioxane, pyridine, acetic acid, DMSO, DMF, DMA, acetonitrile, acetone, methylene chloride, etc. can be used alone or as a mixture of some of them. The amount of the solvent is usually about 1 to 100 fold, and preferably about 3 to 30 fold relative to that of Compound (7) in terms of weight. In the method using a metal and an acid, water, acetone or the like is often used as the solvent, but the acid can be used as the solvent as well when the acid is a liquid. For the deprotection of the hydroxy group at position 6' of Compound (7), a method using p-toluenesulfonic acid is particularly preferable.

The reaction temperature for the deprotection is usually about 0 to 100° C., and preferably about 10 to 50° C. The reaction duration for the deprotection is not particularly limited, and in such a temperature range, usually about 10 minutes to about 24 hours, and preferably about 3 to 20 hours. An example of Compound (8) obtainable in Step 4-3 is 2',3'-O-cyclohexylidene-4'-C-(hydroxymethyl)-5-methyl-5'-O-pivaloyluridine represented by Formula (8-1):

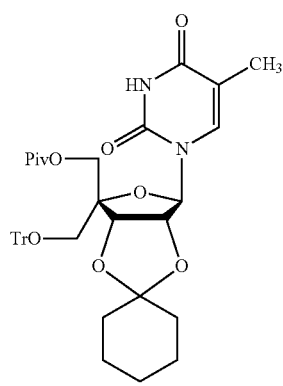

(8-1)

(wherein Ply has the same meaning as defined above), or the like.

[Step 5]

In Step 5, the compound represented by Formula (9) (hereinafter referred to as Compound (9)) can be obtained by oxidation of the hydroxy group at position 6' of Compound (8). Specifically, Compound (9) can be obtained by mixing of Compound (8) with an oxidizing agent in a solvent, for example. These materials may be added in any order without particular limitation.

Examples of the oxidizing agent include organic oxidizers such as 2,3-dichloro-5,6-dicyano-p-benzoquinone, chloranil, bromanil, 1,4-diphenoquinone, tetramethyldiphenoquinone, tetracyanoquinodimethane, tetracyanoethylene and thionyl chloride; organic peroxides such as perbenzoic acid, m-chloroperbenzoic acid and benzoyl peroxide; lead tetraacetate; thallium triacetate; cerium(IV); vanadium pentoxide; magnesium monoperoxyphthalate; potassium peroxymonosulfate; and dimethyl sulfoxide (DMSO). Dimethyl sulfoxide is preferred. In the case where the oxidizing agent is used, an activating agent is preferably used together with the oxidizing agent.

Examples of the activating agent include carbodiimide compounds such as 1-ethyl-3-(3-dimethylaminopropyl)carbodiimide hydrochloride (hereinafter abbreviated as WSC.HCl), N,N'-dicyclohexylcarbodiimide and N,N'-diisopropylcarbodiimide; carboxylic acid halides such as acetyl chloride, acetyl bromide, acetyl iodide, propionyl chloride, butyryl chloride and butyryl bromide; sulfur trioxide derivatives such as a sulfur trioxide-amine complex (for example, pyridine-sulfur trioxide etc.) and a sulfur trioxide-N,N-dimethylformamide (DMF) complex; oxalyl chloride; trifluoroacetic anhydride; acetic anhydride; methanesulfonic acid; p-toluenesulfonic acid; camphorsulfonic acid; trifluoromethanesulfonic acid; a boron trifluoride-diethyl ether complex; PPTS; acetic acid; dichloroacetic acid; and trifluoroacetic acid (TFA). WSC.HCl or PPTS is preferred. These activating agents may be used alone or as a mixture of two or more kinds thereof. The amount of the oxidizing agent is usually about 1 to 10 mol, and preferably about 1 to 5 mol per mole of Compound (8). The amount of the activating agent is usually about 1 to 10 mol, and preferably about 1 to 5 mol per mole of Compound (8).

Any reaction solvent that does not disturb the reaction concerned can be preferably used, and examples thereof include ketone solvents (for example, methyl ethyl ketone etc.), ether solvents (for example, DME, THF, etc.), nitrile compounds (for example, acetonitrile, propionitrile, benzonitrile, etc.), aromatic organic solvents (for example, benzene, toluene, xylene, etc.), halogenated solvents (for example, dichloromethane, chloroform, etc.), hydrocarbon solvents (hexane, heptane, octane), dimethyl sulfoxide, DMF, DMA and ethyl acetate. These solvents may be used alone or as a mixture of two or more kinds thereof. In the case where dimethyl sulfoxide (DMSO) is used as the oxidizing agent, DMSO can serve as the solvent as well, and one or more kinds of solvents set forth above may be used in addition to DMSO as long as the solvents do not disturb the oxidation reaction. The amount of the solvent is usually about 1 to 100 fold, and preferably about 2 to 30 fold relative to that of Compound (8) in terms of weight.

The reaction temperature is usually about −70 to 100° C., and preferably about 20 to 60° C. The reaction duration is not particularly limited, and in such a temperature range, usually about 10 minutes to about 24 hours, and preferably about 30 minutes to about 2 hours. An example of Compound (9) obtainable in Step 5 is 2',3'-O-cyclohexylidene-4'-C-formyl-5-methyl-5'-O-pivaloyl-uridine represented by Formula (9-1):

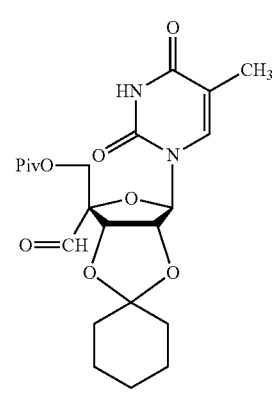

(9-1)

(wherein Ply has the same meaning as defined above), or the like.

Optionally, Compound (9) obtained in Step 5 may be subjected to the following treatment for purification.

In the treatment for purification, Compound (9) obtained in Step 5 is converted into a hydrogen sulfite adduct thereof. Thereby, impurities can be removed from Compound (9) and Compound (9) with high purity can be obtained.

Specifically, a hydrogen sulfite adduct of Compound (9) can be produced by contact of Compound (9) with, for example, sodium hydrogen sulfite in a solvent, resulting in production of a highly pure Compound (9).

The amount of sodium hydrogen sulfite is usually about 1 to 20 mol, and preferably about 2 to 5 mol per mole of Compound (9).

Any reaction solvent that does not disturb the reaction concerned can be preferably used, and examples thereof include N,N-dimethylformamide (DMF), N,N-dimethylacetamide (DMA), dimethyl sulfoxide (DMSO), water, alcoholic solvents (for example, methanol, ethanol, isopropanol, etc.) and DME. Inter alis, DMF is preferred. These solvents may be used alone or as a mixture of two or more kinds thereof.

The amount of the solvent is usually about 1 to 100 fold, and preferably about 10 to 50 fold relative to that of Compound (9) in terms of weight.

The reaction temperature is usually about 10 to 50° C., and preferably about 20 to 40° C. The reaction duration is not particularly limited, and in such a temperature range, usually about 10 minutes to about 24 hours, and preferably about 30 minutes to about 4 hours.

After the treatment for purification, methods known per se (for example, filtration, washing, desiccation, etc.) give a highly pure crystal of Compound (9). All these procedures can be performed under normal, reduced or increased pressure, in an atmosphere of air or inert gas.

Such a purification step via the production of a hydrogen sulfite adduct allows impurities to be efficiently removed from Compound (9) and thereby a highly pure Compound (9) to be obtained.

Examples of the impurities removable in Step 5-1 include epi-CPA (2',3'-O-cyclohexylidene-5-methyl-4'-C-[(pivaloyloxy)-methyl]uridine 5'-aldehyde) represented by the following Formula (9-2):

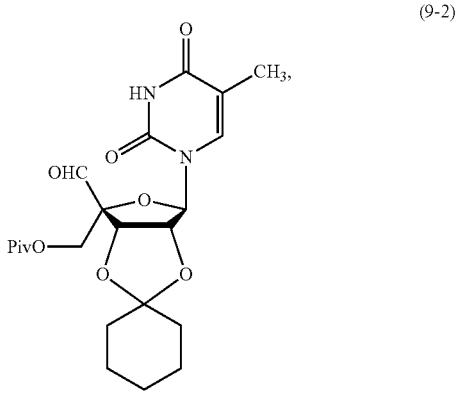

(9-2)

and
CPTE (2',3'-O-cyclohexylidene-5-methyl-4'-C-[(methylthiomethyl)-oxymethyl]-5'-O-pivaloyluridine) represented by the following Formula (8-2):

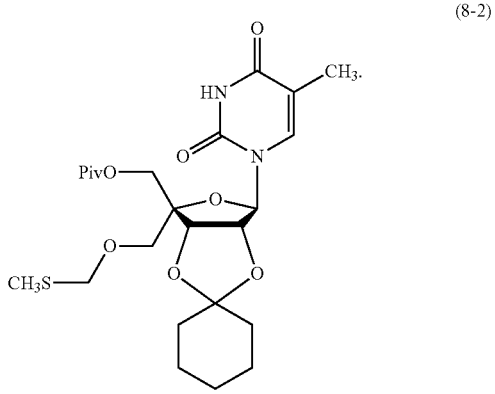

(8-2)

[Step 6]
In Step 6, the compound represented by Formula (10) (hereinafter referred to as Compound (10)) can be obtained by the Wittig reaction of Compound (9). Specifically, Compound (10) can be obtained by treatment of a phosphonium salt with a base in a solvent, followed by the Wittig reaction of the resulting alkylidene phosphorane with Compound (9), for example.

Preferable examples of the phosphonium salt in Step 6 include chloromethyl tributyl phosphonium chloride, chloromethyl triethyl phosphonium chloride, chloromethyl triphenyl phosphonium chloride and chloromethyl triphenoxy phosphonium chloride, and bromides and iodides corresponding to these chlorides. Chloromethyl triphenyl phosphonium chloride is particularly preferred. The amount of the phosphonium salt is usually about 1 to 10 mol, and preferably about 1 to 5 mol per mole of Compound (9).

Preferable examples of the base in Step 6 include lithium diisopropylamide (LDA) and n-butyllithium. The amount of the base is preferably an approximately equimolar amount of the phosphonium salt.

Any reaction solvent that does not disturb the reaction concerned can be preferably used, and examples thereof include ether solvents (for example, DME, THF, etc.), nitrile compounds (for example, acetonitrile, propionitrile, benzonitrile, etc.), aromatic organic solvents (for example, benzene, toluene, xylene, etc.), halogenated solvents (for example, dichloromethane, chloroform, etc.), hydrocarbon solvents (hexane, heptane, octane), DMSO and DMF. These solvents may be used alone or as a mixture of two or more kinds thereof. The amount of the solvent is usually about 1 to 100 fold, and preferably about 5 to 50 fold relative to that of Compound (9) in terms of weight.

The reaction temperature is usually about −70 to 100° C., and preferably about −50 to −10° C. The reaction duration is not particularly limited, and in such a temperature range, usually about 10 minutes to about 24 hours, and preferably about 30 minutes to about 4 hours. An example of Compound (10) obtainable in Step 6 is (Z)-4'-C-(2-chloroethenyl)-2',3'-O-cyclohexylidene-5-methyl-5'-O-pivaloyluridine represented by Formula (10-1):

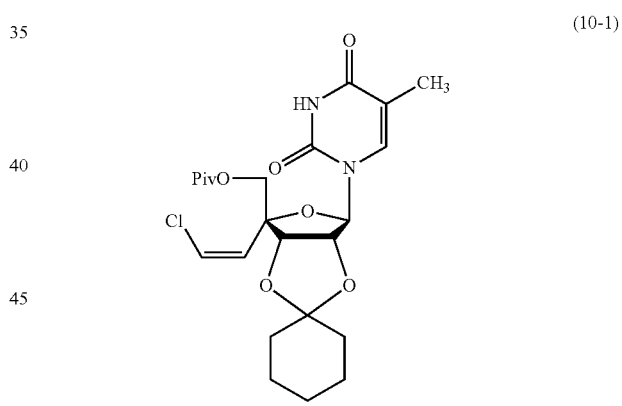

(10-1)

(wherein Piv has the same meaning as defined above), or the like.

[Step 7]
In Step 7, the compound represented by Formula (11) (hereinafter referred to as Compound (11)) can be obtained by selective deprotection of the hydroxy groups at positions 2' and 3' of Compound (10).

For the deprotection of the hydroxy groups at positions 2' and 3' of Compound (10), depending on the kind of the protective group, an appropriate method may be selected from a method using an acid or a base and a method using catalytic reduction. In the case of the method using an acid, the acid to be used varies with the kind of the protective group and other conditions, and examples thereof include inorganic acids such as hydrochloric acid, hydrogen bromide, hydrogen fluoride, hydrogen iodide, methanesulfonic acid, p-toluenesulfonic acid, camphorsulfonic acid, trifluoromethanesulfonic acid, sulfuric acid and phosphoric acid; organic acids such as formic acid, acetic acid and trifluoroacetic acid; and acidic ion exchange resins. In the case of the method using a base, the base to be used varies with the kind of the protective group and other conditions, and examples thereof include inorganic bases such as hydroxides and carbonates of alkali metals such as sodium and potassium or of alkaline earth metals such as calcium and magnesium; organic bases such as metal alkoxides, organic amines and quaternary ammonium salts; and basic ion exchange resins. In the case where a solvent is used in the method using an acid or a base, for example, water, methanol, ethanol, ethyl acetate, chloroform, tetrahydrofuran, dioxane, pyridine, acetic acid, DMSO, DMF, acetonitrile, acetone, methylene chloride, etc. can be used alone or as a mixture of some of them. The amount of the solvent is usually about 1 to 100 fold, and preferably about 25 to 90 fold relative to that of Compound (10) in terms of weight. In the method using a metal and an acid, water, acetone or the like is often used as the solvent, but the acid can be used as the solvent as well when the acid is a liquid. For the deprotection of the hydroxy groups at positions 2' and 3' of Compound (10), a method using an acid, especially hydrochloric acid, is particularly preferable.

The reaction temperature for the deprotection is usually about 0 to 100° C., and preferably about 0 to 40° C. The reaction duration for the deprotection is not particularly limited, and in such a temperature range, usually about 10 minutes to about 24 hours, and preferably about 30 minutes to about 2 hours. An example of Compound (11) obtainable in Step 7 is (Z)-4'-C-(2-chloroethenyl)-5-methyl-5'-O-pivaloyluridine represented by Formula (11-1):

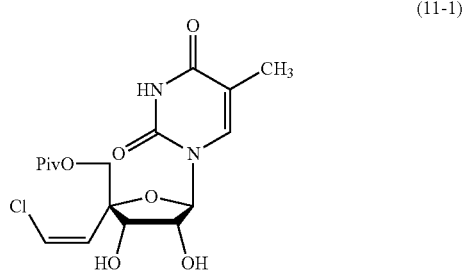

(wherein Piv has the same meaning as defined above), or the like.

[Step 8]

In Step 8, the compound represented by Formula (12) (hereinafter referred to as Compound (12)) can be obtained by an ester exchange reaction of Compound (11) with an ortho carboxylic acid ester, followed by treatment of the reactant with an acid halide. Specifically, Compound (12) can be obtained by an ester exchange reaction of Compound (11) with an ortho carboxylic acid ester, preferably in the presence of an acid, followed by treatment of the reactant with a solution of hydrogen halide in carboxylic acid, in the presence of an acid halide or an acid anhydride.

Preferable examples of the ortho carboxylic acid ester in Step 8 include trimethyl orthoformate, triethyl orthoformate, trimethyl orthoacetate and triethyl orthoacetate. The amount of the ortho carboxylic acid ester is usually about 1 to 10 mol, and preferably about 1 to 5 mol per mole of Compound (11).

The acid in Step 8 may be any of organic acids such as formic acid, acetic acid and propionic acid, and inorganic acids such as hydrochloric acid, sulfuric acid, nitric acid and phosphoric acid, but acetic acid is preferred. The amount of the acid is usually about 1 to 100 fold, and preferably about 1 to 6 fold relative to that of Compound (11) in terms of weight.

As the solvent in the ester exchange reaction, the acid set forth above can be used. Also, an additional solvent may be used preferably as long as it does not disturb the reaction concerned. Examples of the additional solvent include ketone solvents (for example, methyl ethyl ketone etc.), ether solvents (for example, DME, THF, etc.), nitrile compounds (for example, acetonitrile, propionitrile, benzonitrile, etc.), aromatic organic solvents (for example, benzene, toluene, xylene, etc.), halogenated solvents (for example, dichloromethane, chloroform, 1,2-dichloroethane, etc.), DMSO, DMF, DMA and ethyl acetate. These solvents may be used alone or as a mixture of two or more kinds thereof. The amount of the solvent is usually about 1 to 100 fold, preferably about 1 to 6 fold, and more preferably about 1 to 4 fold relative to that of Compound (11) in terms of weight.

The duration of the ester exchange reaction is usually about 10 minutes to about 24 hours, and preferably about 30 minutes to about 2 hours. The temperature for the ester exchange reaction is usually about 0 to 100° C., and preferably about 40 to 80° C.

Preferable examples of the acid anhydride in Step 8 include carboxylic anhydrides such as acetic anhydride, propionic anhydride, succinic anhydride, maleic anhydride and phthalic anhydride; and phosphoric anhydrides such as pyrophosphoric acid and diphosphorus pentoxide.

Preferable examples of the acid halide in Step 8 include acetyl bromide, acetyl chloride, benzoyl bromide, benzoyl chloride, acryloyl bromide, acryloyl chloride, methacryloyl bromide, methacryloyl chloride, propioloyl bromide, propioloyl chloride, pyridinecarbonyl bromide and pyridinecarbonyl chloride. The amount of the acid halide is usually about 1 to 10 mol, and preferably about 1 to 5 mol per mole of Compound (11).

Examples of the solution of hydrogen halide in carboxylic acid in Step 8 include a solution of hydrogen bromide in acetic acid, a solution of hydrogen bromide in propionic acid and a solution of hydrogen chloride in acetic acid. Preferred is a solution of hydrogen bromide in acetic acid. The amount of hydrogen bromide in acetic acid is usually about 1 to 10 mol, and preferably about 1 to 5 mol per mole of Compound (11).

As the solvent used in the treatment with a solution of hydrogen halide in carboxylic acid, in the presence of an acid halide or an acid anhydride, any solvent that does not disturb the reaction concerned can be preferably used, and examples thereof include ketone solvents (for example, methyl ethyl ketone etc.), ether solvents (for example, DME, THF, etc.), nitrile compounds (for example, acetonitrile, propionitrile, benzonitrile, etc.), aromatic organic solvents (for example, benzene, toluene, xylene, etc.), halogenated solvents (for example, dichloromethane, chloroform, etc.), hydrocarbon solvents (hexane, heptane, octane), DMSO, DMF and ethyl acetate. These solvents may be used alone or as a mixture of two or more kinds thereof. The amount of the solvent is usually about 1 to 100 fold, preferably about 3 to 24 fold, and more preferably about 4 to 16 fold relative to that of Compound (11) in terms of weight.

The duration of the acid halide treatment is usually about 1 to 100 hours, and preferably about 23 to 92 hours. The temperature for the acid halide treatment is usually about 0 to 100° C., and preferably about 30 to 70° C. An example of Compound (12) obtainable in Step 8 is (Z)-3'-O-acetyl-2'-α-bromo-4'-C-(2-chloroethenyl)-5'-O-pivaloyluridine represented by Formula (12-1):

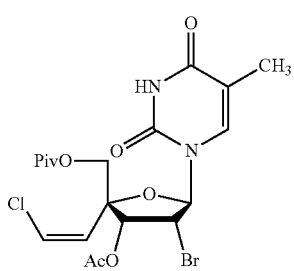

(12-1)

(wherein Piv has the same meaning as defined above), or the like.

[Step 9]

In Step 9, the compound represented by Formula (13) (hereinafter referred to as Compound (13)) can be obtained by a reductive elimination reaction of Compound (12). Specifically, Compound (13) can be obtained by reaction of metal with a metal activating agent, preferably in a solvent, followed by mixing of the reactant with Compound (12).

Preferable examples of the metal in Step 9 include potassium, calcium, sodium, magnesium, aluminum, zinc, iron, nickel and alloys such as tin-copper and zinc-copper. More preferred is zinc or a zinc-copper alloy. The amount of the metal is usually about 1 to 10 mol, and preferably about 1 to 5 mol per mole of Compound (12).

Examples of the metal activating agent include 1,2-dibromoethane, chlorotrimethylsilane, dilute hydrochloric acid, copper sulfate pentahydrate and iodine. The amount of the metal activating agent is usually about 0.01 to 1 mol, and preferably about 0.01 to 0.5 mol per mole of the metal.

Any reaction solvent that does not disturb the reaction concerned can be preferably used, and examples thereof include ketone solvents (for example, methyl ethyl ketone etc.), ether solvents (for example, DME, THF, etc.), nitrile compounds (for example, acetonitrile, propionitrile, benzonitrile, etc.) aromatic organic solvents (for example, benzene, toluene, xylene, etc.), halogenated solvents (for example, dichloromethane, chloroform, etc.), hydrocarbon solvents (hexane, heptane, octane), DMSO, DMF, DMA and ethyl acetate. These solvents may be used alone or as a mixture of two or more kinds thereof. The amount of the solvent is usually about 1 to 100 fold, and preferably about 3 to 30 fold relative to that of Compound (12) in terms of weight.

The reaction temperature is usually about 0 to 100° C., and preferably about 20 to 60° C. The reaction duration is not particularly limited, and in such a temperature range, usually about 10 minutes to about 24 hours, and preferably about 1 to 4 hours. An example of Compound (13) obtainable in Step 8 is (Z)-4'-C-(2-chloroethenyl)-2',3'-didehydro-3'-deoxy-5'-O-pivaloylthymidine represented by Formula (13-1):

[Formula 69]

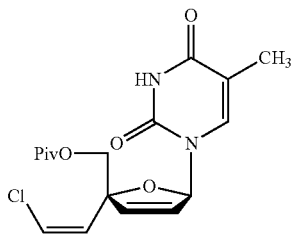

(13-1)

(wherein Piv has the same meaning as defined above), or the like.

[Step 10a]

In Step 10, Compound (1) can be obtained by treatment of Compound (13) with a base, and preferably, successively with an alkaline solution, in the presence of a halogenated silane or a compound capable of being a ligand for Lewis acid metals (which means metals capable of serving as a Lewis acid, for example, lithium, magnesium, titanium and zinc).

Preferable examples of the halogenated silane in Step 10 are halogenated trihydrocarbon silanes etc. Examples of the halogenated trihydrocarbon silane include halogenated trialkylsilanes such as chlorotrimethylsilane and chlorotriethylsilane; halogenated aryl dialkyl silanes such as chlorophenyl dimethylsilane and chlorodiphenylmethylsilane; halogenated alkyl diaryl silanes; and halogenated triarylsilanes. Examples of the halogen in the halogenated silane include chlorine, bromine and iodine, and chlorine is preferred. The amount of the halogenated silane is usually about 1 to 10 mol, and preferably about 1 to 5 mol per mole of Compound (13). In Step 10, a preferable example of the compound capable of being a ligand for Lewis acid metals is N,N,N',N'-tetramethylethylenediamine (TMEDA).

Preferable examples of the base in Step 10 include lithium diisopropylamide (LDA), n-butyllithium, sodium tert-butoxide and potassium tert-butoxide. The amount of the base is usually about 1 to 10 mol, and preferably about 1 to 5 mol per mole of Compound (13).

Any reaction solvent that does not disturb the reaction concerned can be preferably used, and examples thereof include ether solvents (for example, DME, THF, etc.), nitrile compounds (for example, acetonitrile, propionitrile, benzonitrile, etc.), aromatic organic solvents (for example, benzene, toluene, xylene, etc.), halogenated solvents (for example, dichloromethane, chloroform, etc.), hydrocarbon solvents (hexane, heptane, octane) and DMSO. These solvents may be used alone or as a mixture of two or more kinds thereof. The amount of the solvent is usually about 1 to 100 fold, and preferably about 10 to 90 fold relative to that of Compound (13) in terms of weight.

The reaction temperature is usually about −70 to 100° C., and preferably about −50 to −10° C. The reaction duration is not particularly limited, and in such a temperature range, usually about 10 minutes to about 24 hours, and preferably about 2 to 10 hours.

After completion of treatment with the base, treatment with an alkaline solution is optionally performed.

Preferable examples of the alkaline solution in Step 10 include aqueous solutions of an alkali metal hydroxide (for example, lithium hydroxide, sodium hydroxide, potassium hydroxide, cesium hydroxide, rubidium hydroxide, etc.), an alkaline earth metal hydroxide (for example, calcium hydroxide, magnesium hydroxide, strontium hydroxide, barium hydroxide, etc.) or the like.

The amount of the alkaline solution is usually about 10 to 50 mol, and preferably about 10 to 30 mol per mole of Compound (13).

Any reaction solvent that does not disturb the reaction concerned can be preferably used, and examples thereof include alcoholic solvents (for example, methanol, ethanol, etc.), ketone solvents (for example, methyl ethyl ketone etc.), ether solvents (for example, DME, THF, etc.), nitrile compounds (for example, acetonitrile, propionitrile, benzonitrile, etc.), aromatic organic solvents (for example, benzene, toluene, xylene, etc.), halogenated solvents (for example, dichloromethane, chloroform, 1,2-dichloroethane, etc.), DMSO and ethyl acetate. These solvents may be used alone or as a mixture of two or more kinds thereof. The amount of the solvent is usually about 1 to 100 fold, and preferably about 15 to 65 fold relative to that of Compound (13) in terms of weight.

The temperature for the treatment with the alkaline solution is usually about 0 to 100° C., and preferably about 0 to 40° C. The treatment duration is not particularly limited, and in such a temperature range, usually about 10 minutes to about 24 hours, and preferably about 1 to 4 hours.

After the treatment with an alkaline solution, column purification, recrystallization, etc. may be performed by a known method. Then, a crystal of 2',3'-didehydro-3'-deoxy-4'-ethynylthymidine can be obtained by methods known per se (for example, filtration, washing, desiccation, etc.). In the crystallization step, an acid or a base may be appropriately added, and thereby a crystal of a pharmacologically acceptable salt of 2',3'-didehydro-3'-deoxy-4'-ethynylthymidine can obtained. All these procedures can be performed under normal, reduced or increased pressure, in an atmosphere of air or inert gas.

A second embodiment of the production process of the present invention is represented by the reaction scheme below.

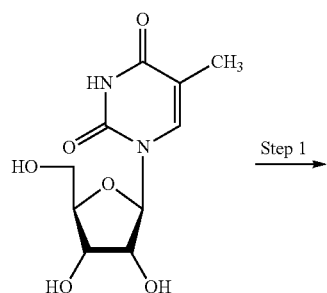

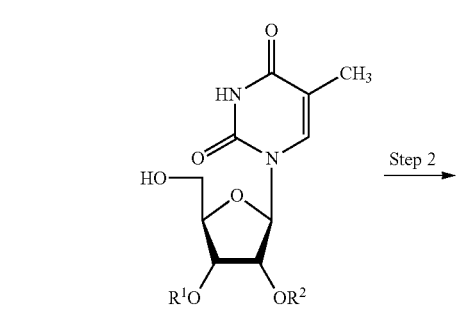

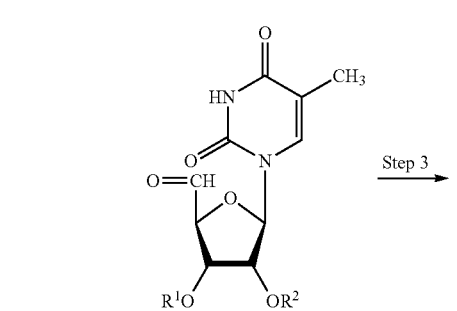

-continued

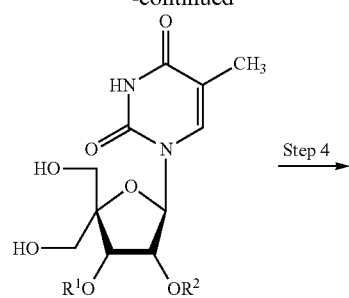

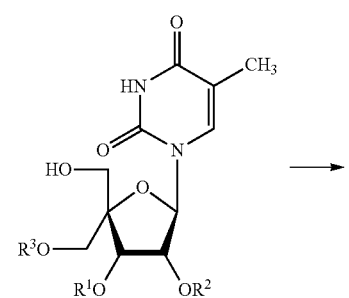

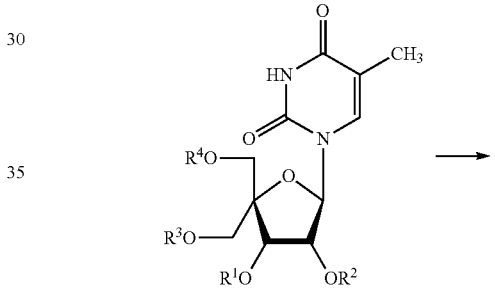

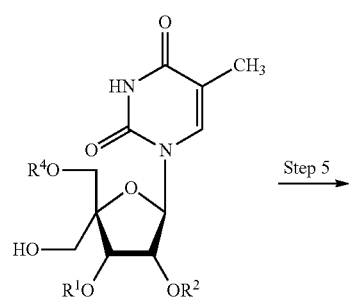

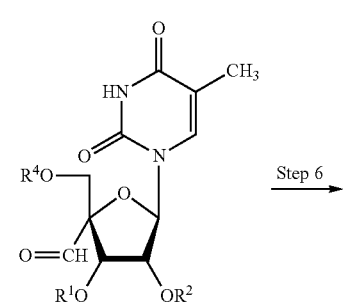

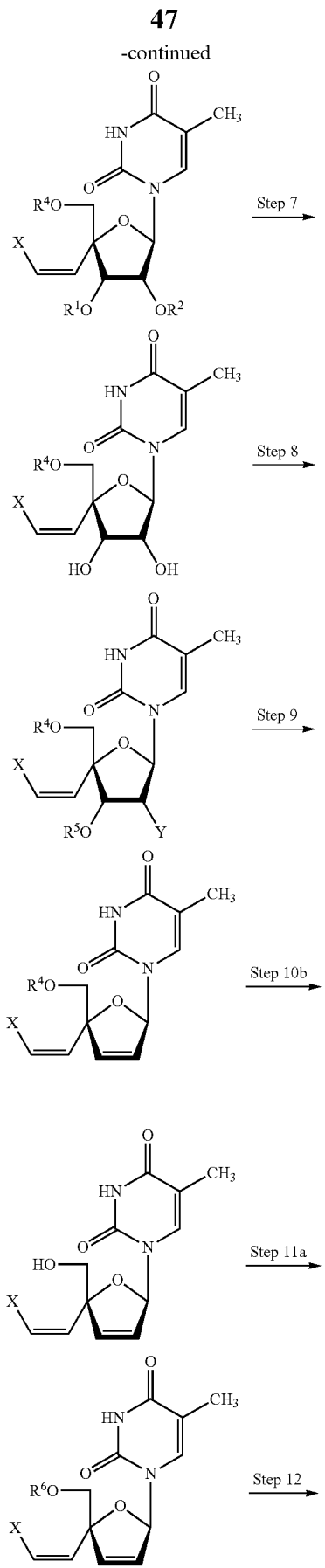

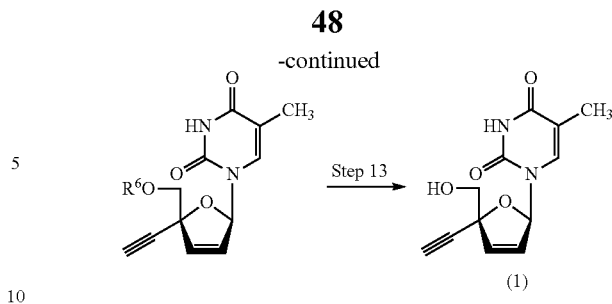

(wherein each symbol has the same meaning as defined above.)

Hereinafter, each step in the second embodiment of the present invention will be described.

[Step 10b]

Steps 1 to 9 can be performed in the same manner as above. In Step 10b, the compound represented by Formula (14) (hereinafter referred to as Compound (14)) can be obtained by selective deprotection of the hydroxy group at position 5' of Compound (13) obtained in Step 9.

For the deprotection of the hydroxy group at position 5' of Compound (13), depending on the kind of the protective group, an appropriate method may be selected from a method using an acid or a base and a method using catalytic reduction. In the case of the method using an acid, the acid to be used varies with the kind of the protective group and other conditions, and examples thereof include inorganic acids such as hydrochloric acid, hydrogen bromide, hydrogen fluoride, hydrogen iodide, methanesulfonic acid, p-toluenesulfonic acid, camphorsulfonic acid, trifluoromethanesulfonic acid, sulfuric acid and phosphoric acid; organic acids such as formic acid, acetic acid and trifluoroacetic acid; and acidic ion exchange resins. In the case of the method using a base, the base to be used varies with the kind of the protective group and other conditions, and examples thereof include inorganic bases such as hydroxides and carbonates of alkali metals such as sodium and potassium or of alkaline earth metals such as calcium and magnesium; organic bases such as metal alkoxides, organic amines and quaternary ammonium salts; and basic ion exchange resins. In the case where a solvent is used in the method using an acid or a base, for example, water, methanol, ethanol, ethyl acetate, chloroform, tetrahydrofuran, dioxane, pyridine, acetic acid, DMSO, DMF, DMA, acetonitrile, acetone, methylene chloride, etc. can be used alone or as a mixture of some of them. The amount of the solvent is usually about 1 to 100 fold, and preferably about 3 to 30 fold relative to that of Compound (13) in terms of weight. In the method using a metal and an acid, water, acetone or the like is often used as the solvent, but the acid can be used as the solvent as well when the acid is a liquid. For the deprotection of the hydroxy group at position 5' of Compound (13), a method using an acid, especially hydrochloric acid, is particularly preferable.

The reaction temperature for the deprotection is usually about 0 to 100° C., and preferably about 10 to 50° C. The reaction duration for the deprotection is not particularly limited, and in such a temperature range, usually about 10 minutes to about 24 hours, and preferably about 1 to 4 hours. An example of Compound (14) obtainable in Step 10b is (Z)-4'-C-(2-chloroethenyl)-2',3'-didehydro-3'-deoxy-thymidine represented by Formula (14-1):

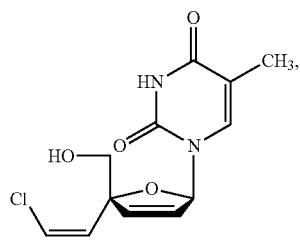

(14-1)

or the like.

[Step 11a]

In Step 11a, the compound represented by Formula (15) (hereinafter referred to as Compound (15)) can be obtained by selective protection of the hydroxy group at position 5' of Compound (14). Specifically, Compound (15) can be obtained by a condensation reaction of Compound (14) with a protecting agent, preferably in the presence of an acid or base catalyst.

Examples of the acid catalyst include p-toluenesulfonic acid and PPTS. Examples of the base catalyst include DMAP, 1,8-diazabicyclo[5.4.0]undec-7-ene (DBU), 1,5-diazabicyclo[4.3.0]non-5-ene (DBN), 2,6-lutidine, 2,4,6-collidine, 2,3,5-collidine, 2-picoline, 3-picoline and 4-picoline. The amount of the acid or base catalyst is usually about 0.01 to 1 mol, and preferably about 0.01 to 0.5 mol per mole of Compound (14). An auxiliary base may be present in this reaction. Examples of the auxiliary base include tertiary amines such as triethylamine, tributylamine, ethyldiisopropylamine, tetramethylenediamine and pyridine. Triethylamine is preferred. The amount of the auxiliary base is usually about 1 to 10 mol, and preferably about 1 to 5 mol per mole of Compound (14).

Preferable examples of the protecting agent include halogenated triphenylmethanes, such as chlorotriphenylmethane (trityl chloride) and bromotriphenylmethane, and dihydropyrane.

Any reaction solvent that does not disturb the reaction concerned can be preferably used, and examples thereof include ketone solvents (for example, methyl ethyl ketone etc.), ether solvents (for example, DME, THF, etc.), nitrile compounds (for example, acetonitrile, propionitrile, benzonitrile, etc.), aromatic organic solvents (for example, benzene, toluene, xylene, etc.), halogenated solvents (for example, dichloromethane, chloroform, etc.), hydrocarbon solvents (hexane, heptane, octane), DMSO, DMF, DMA and ethyl acetate. These solvents may be used alone or as a mixture of two or more kinds thereof. The amount of the solvent is usually about 1 to 100 fold, and preferably about 3 to 30 fold relative to that of Compound (14) in terms of weight.

The reaction temperature is usually about 0 to 100° C., and preferably about 60 to 100° C. The reaction duration is not particularly limited, and in such a temperature range, usually about 10 minutes to about 24 hours, and preferably about 5 to 20 hours. An example of Compound (15) obtainable in Step 11 is (Z)-4'-C-(2-chloroethenyl)-2',3'-didehydro-3'-deoxy-5'-O-tritylthymidine represented by Formula (15-1):

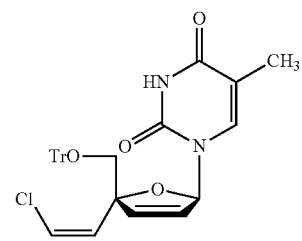

(15-1)

(wherein Tr has the same meaning as defined above), or the like.

[Step 12]

In Step 12, the compound represented by Formula (16) (hereinafter referred to as Compound (16)) can be obtained by treatment of Compound (15) with a base.

Preferable examples of the base in Step 12 include lithium diisopropylamide (LDA), n-butyllithium, sodium tert-butoxide and potassium tert-butoxide. The amount of the base is usually about 1 to 10 mol, and preferably about 1 to 5 mol per mole of Compound (15).

Any reaction solvent that does not disturb the reaction concerned can be preferably used, and examples thereof include ether solvents (for example, DME, THF, etc.), nitrile compounds (for example, acetonitrile, propionitrile, benzonitrile, etc.), aromatic organic solvents (for example, benzene, toluene, xylene, etc.), halogenated solvents (for example, dichloromethane, chloroform, etc.), hydrocarbon solvents (hexane, heptane, octane) and DMSO. These solvents may be used alone or as a mixture of two or more kinds thereof. The amount of the solvent is usually about 1 to 100 fold, and preferably about 5 to 50 fold relative to that of Compound (15) in terms of weight.

The reaction temperature is usually about −70 to 100° C., and preferably about −50 to −10° C. The reaction duration is not particularly limited, and in such a temperature range, usually about 10 minutes to about 24 hours, and preferably about 30 minutes to about 2 hours. An example of Compound (16) obtainable in Step 12 is 2',3'-didehydro-3'-deoxy-4'-C-ethynyl-5'-O-tritylthymidine represented by Formula (16-1):

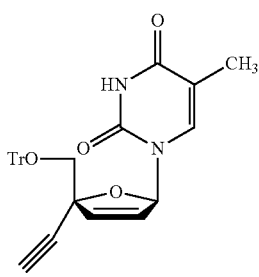

(16-1)

(wherein Tr has the same meaning as defined above), or the like.

[Step 13]

In Step 13, Compound (1) can be obtained by selective deprotection of the hydroxy group at position 5' of Compound (16) obtained above.

For the deprotection of the hydroxy group at position 5' of Compound (16), depending on the kind of the protective group, an appropriate method may be selected from a method using an acid and a method using catalytic reduction. In the case of the method using an acid, the acid to be used varies with the kind of the protective group and other conditions, and examples thereof include inorganic acids such as hydrochloric acid, hydrogen bromide, hydrogen fluoride, hydrogen iodide, methanesulfonic acid, p-toluenesulfonic acid (tosyl acid), camphorsulfonic acid, trifluoromethanesulfonic acid, sulfuric acid and phosphoric acid; organic acids such as formic acid, acetic acid and trifluoroacetic acid; and acidic ion exchange resins. In the case where a solvent is used in the method using an acid, for example, water, methanol, ethanol, ethyl acetate, chloroform, tetrahydrofuran, dioxane, pyridine, acetic acid, DMSO, DMF, DMA, acetonitrile, acetone, methylene chloride, etc. can be used alone or as a mixture of some of them. The amount of the solvent is usually about 1 to 100 fold, and preferably about 3 to 30 fold relative to that of Compound (16) in terms of weight. In the method using a metal and an acid, water, acetone or the like is often used as the solvent, but the acid can be used as the solvent as well when the acid is a liquid. For the deprotection of the hydroxy group at position 5' of Compound (16), a method using p-toluenesulfonic acid is particularly preferable.

The reaction temperature for the deprotection is usually about 0 to 100° C., and preferably about 10 to 50° C. The reaction duration for the deprotection is not particularly limited, and in such a temperature range, usually about 10 minutes to about 24 hours, and preferably about 3 to 12 hours.

After the above deprotection, column purification, recrystallization, etc. may be performed by a known method. Then, a crystal of 2',3'-didehydro-3'-deoxy-4'-ethynylthymidine can be obtained by methods known per se (for example, filtration, washing, desiccation, etc.). In the crystallization step, an acid or a base may be appropriately added, and thereby a crystal of a pharmacologically acceptable salt of 2',3'-didehydro-3'-deoxy-4'-ethynylthymidine can obtained. All these procedures can be performed under normal, reduced or increased pressure, in an atmosphere of air or inert gas.

A third embodiment of the production process of the present invention is represented by the reaction scheme below.

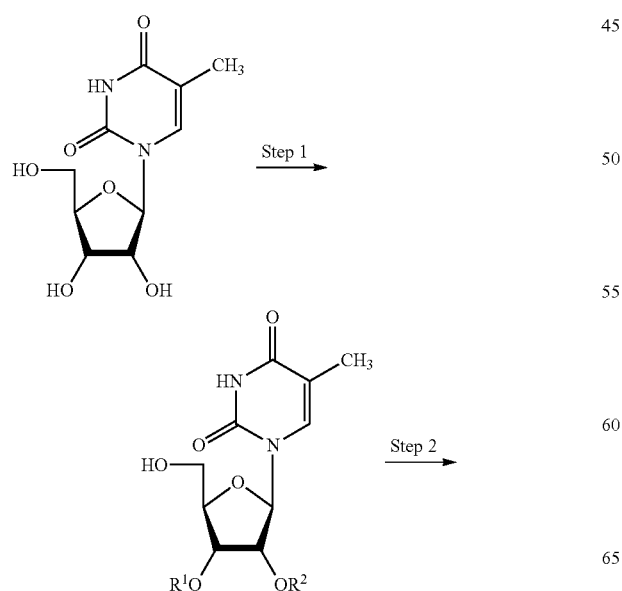

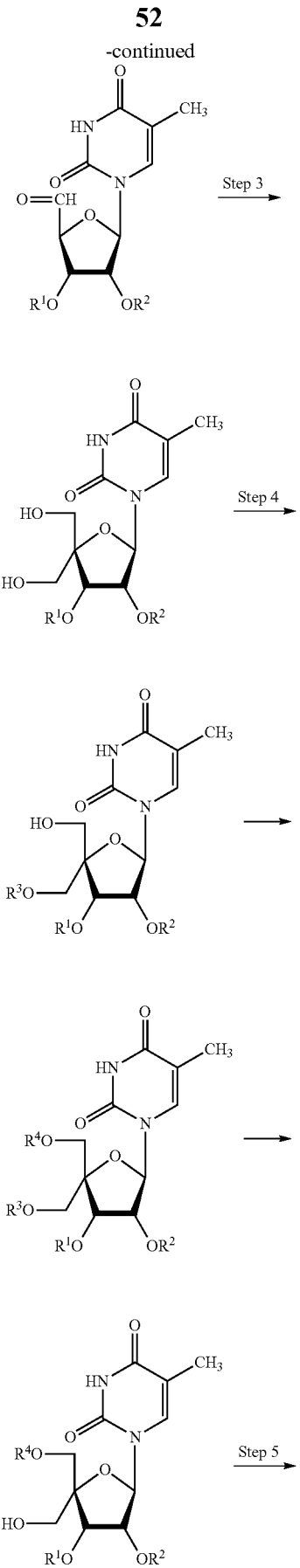

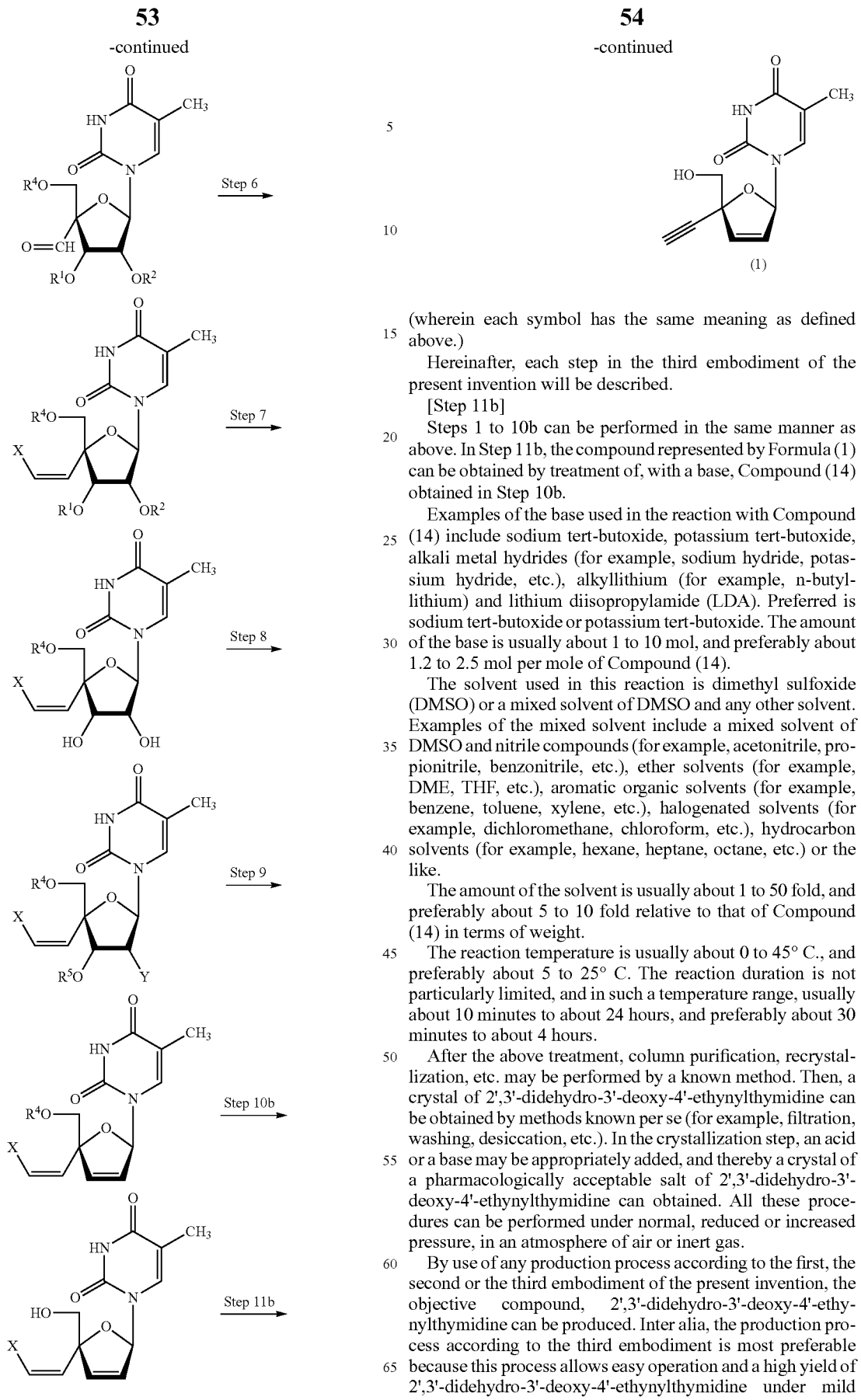

(wherein each symbol has the same meaning as defined above.)

Hereinafter, each step in the third embodiment of the present invention will be described.

[Step 11b]

Steps 1 to 10b can be performed in the same manner as above. In Step 11b, the compound represented by Formula (1) can be obtained by treatment of, with a base, Compound (14) obtained in Step 10b.

Examples of the base used in the reaction with Compound (14) include sodium tert-butoxide, potassium tert-butoxide, alkali metal hydrides (for example, sodium hydride, potassium hydride, etc.), alkyllithium (for example, n-butyllithium) and lithium diisopropylamide (LDA). Preferred is sodium tert-butoxide or potassium tert-butoxide. The amount of the base is usually about 1 to 10 mol, and preferably about 1.2 to 2.5 mol per mole of Compound (14).

The solvent used in this reaction is dimethyl sulfoxide (DMSO) or a mixed solvent of DMSO and any other solvent. Examples of the mixed solvent include a mixed solvent of DMSO and nitrile compounds (for example, acetonitrile, propionitrile, benzonitrile, etc.), ether solvents (for example, DME, THF, etc.), aromatic organic solvents (for example, benzene, toluene, xylene, etc.), halogenated solvents (for example, dichloromethane, chloroform, etc.), hydrocarbon solvents (for example, hexane, heptane, octane, etc.) or the like.

The amount of the solvent is usually about 1 to 50 fold, and preferably about 5 to 10 fold relative to that of Compound (14) in terms of weight.

The reaction temperature is usually about 0 to 45° C., and preferably about 5 to 25° C. The reaction duration is not particularly limited, and in such a temperature range, usually about 10 minutes to about 24 hours, and preferably about 30 minutes to about 4 hours.

After the above treatment, column purification, recrystallization, etc. may be performed by a known method. Then, a crystal of 2',3'-didehydro-3'-deoxy-4'-ethynylthymidine can be obtained by methods known per se (for example, filtration, washing, desiccation, etc.). In the crystallization step, an acid or a base may be appropriately added, and thereby a crystal of a pharmacologically acceptable salt of 2',3'-didehydro-3'-deoxy-4'-ethynylthymidine can obtained. All these procedures can be performed under normal, reduced or increased pressure, in an atmosphere of air or inert gas.

By use of any production process according to the first, the second or the third embodiment of the present invention, the objective compound, 2',3'-didehydro-3'-deoxy-4'-ethynylthymidine can be produced. Inter alia, the production process according to the third embodiment is most preferable because this process allows easy operation and a high yield of 2',3'-didehydro-3'-deoxy-4'-ethynylthymidine under mild conditions.

EXAMPLES

Hereinafter, the present invention will be illustrated by Examples, but is not limited thereto.

Example 1

Production of 2',3'-didehydro-3'-deoxy-4'-ethynylthymidine

Embodiment 1

The title compound was synthesized through the following Steps 1-10a.

[Step 1]

Synthesis of 2',3'-O-cyclohexylidene-5-methyluridine (Compound (3-1))

5-methyluridine (31.0 g, 120 mmol; made by Aldrich) was suspended in THF (300 mL). To this, cyclohexanone dimethyl acetal (36.4 mL, 240 mmol) and p-toluenesulfonic acid monohydrate (p-TsOH) (4.56 g, 24 mmol) were added, and the mixture was refluxed for 30 minutes. After cooling the solution to room temperature, a saturated aqueous solution of sodium hydrogencarbonate (150 mL) was added thereto. Under reduced pressure, THF was distilled off to concentrate the reaction mixture, and potassium carbonate (5.00 g) and methanol (50 mL) were added thereto. The methanol layer was washed with heptane (6×150 mL). The pH was adjusted to 7.5 with 2N hydrochloric acid (25 mL), and extraction was performed with ethyl acetate (2×300 mL). Combined organic layers were dried with magnesium sulfate (15.0 g), filtered, and then concentrated under reduced pressure to give the title compound (3-1) as an oily material (37.2 g, 92%).

(Properties)

$^1$H-NMR (200 MHz, DMSO-$d_6$):

δ 1.28-1.80 (10H, m, 5×$CH_2$), 1.765 (3H, d, J=1.1 Hz, 5-Me), 3.58 [2H, br (ABX-like), 5'-$H_2$], 4.03 (1H, q, J=3.7 Hz, 4'-H), 4.76 (1H, M part of AMNX, $J_{MN}$=6.4 Hz, $J_{AM}$=3.7 Hz, 3'-H), 4.89 (1H, N part of AMNX, $J_{MN}$=6.4 Hz, $J_{NX}$=2.9 Hz, 2'-H), 5.09 (1H, br t-like, 5'-OH), 5.84 [1H, d (X part of ANMX system), J=2.9 Hz, 1'-H], 7.65 (1H, d, J=1.1 Hz, 6-H), and 11.37 (1H, br s, 3-H).

$^{13}$C-NMR (50.3 MHz, DMSO-$d_6$):

δ 11.9 (5-Me), 23.1 ($CH_2$), 23.5 ($CH_2$), 24.4 ($CH_2$), 34.2 ($CH_2$), 36.5 ($CH_2$), 61.2 (5'-C), 80.0 (3'-C), 82.9 (2'-C), 86.2 (4'-C), 90.5 (1'-CH), 109.4 (5-C), 113.6 (quaternary C of CyH), 137.4 (6-C), 150.3 (2-C), and 163.6 (4-C).

[Step 2]

Synthesis of 2',3'-O-cyclohexylidene-5-methyluridine-5'-aldehyde (Compound (4-1))

Compound (3-1) (37.2 g, 110 mmol) was dissolved in dimethyl sulfoxide (DMSO) (370 mL). N-ethyl-N'-(3-dimethylaminopropyl)carbodiimide (WSC) (84.35 g, 440 mmol) and pyridinium p-toluene sulfonate (PPTS) (27.64 g, 110 mmol) were added thereto, and the mixture was stirred at room temperature for 1 hour. Water (700 mL) was added under cooling in an ice bath. After sodium chloride (140 g) was added and dissolved, extraction was performed with ethyl acetate (6×500 mL). Combined organic layers were concentrated under reduced pressure to give a crude product of the title compound (4-1) as an oily material (74.8 g). Since the compound was unstable, it was used in the following step as it was, without purification.

[Step 3]

Synthesis of 2',3'-O-cyclohexylidene-4'-C-hydroxymethyl-5-methyluridine (Compound (5-1))

To the crude product of Compound (4-1) obtained in Step 2 (74.8 g), 37 (w/w) % formalin (160 mL), triethylamine (160 mL) and magnesium bromide hexahydrate (86.43 g, 22 mmol) were added, and the mixture was stirred at room temperature for 45 minutes. After ethyl acetate (180 mL) was added thereto, 2N hydrochloric acid (420 mL) and 6N hydrochloric acid (67 mL) were sequentially added under cooling in an ice bath to adjust the pH to 5. The layers were separated, and the aqueous layer was extracted with ethyl acetate (3×370 mL). Combined organic layers were washed with a saturated aqueous solution of sodium chloride (190 mL), dried with magnesium sulfate (18.6 g), filtered, and then concentrated under reduced pressure to give an oily residual material (48.6 g).

Sodium borohydride (8.32 g, 220 mmol) was suspended in ethanol (190 mL). To this, under cooling in an ice bath, a solution of the above residual material (48.6 g) in ethanol (190 mL) was added dropwise over 30 minutes. Under cooling in an ice bath, stirring was continued for 30 minutes, and then acetic acid (12 mL) was added to adjust the pH to 7. Water (180 mL) was added with stirring, and extraction was performed with ethyl acetate (2×370 mL). The mixture was dried with magnesium sulfate (18.6 g), filtered, and then concentrated under reduced pressure to give an oily residual material (36.3 g). Purifying this residual material by silica gel column chromatography (silica gel: 500 g, heptane:ethyl acetate=4:1 (v/v)→ethyl acetate) gave the title compound (5-1) (24.92 g, yield from 5-methyluridine: 56%) as a colorless amorphous material.

(Properties)

$^1$H-NMR (200 MHz, DMSO-$d_6$): δ 1.30-1.80 (10H, m, 5×$CH_2$), 1.77 (3H, d, J=1.1 Hz, 5-Me), 3.46-3.69 (4H, m, 5'- and 6'-$H_2$), 4.60 (1H, t, J=5.7 Hz, OH), 4.77 (1H, A part of ABX, $J_{AB}$=6.2 Hz, $J_{AX}$=0 Hz, 3'-H), 4.87 (1H, B part of ABX, $J_{AB}$=6.2 Hz, $J_{BX}$=4.2 Hz, 2'-H), 5.17 (1H, t, J=4.9 Hz, OH), 5.91 (1H, d, J=4.2 Hz, 1'-H), 7.77 (1H, d, J=1.1 Hz, 6-H), and 11.33 (1H, br s, 3-H). $^{13}$C-NMR (50.3 MHz, DMSO-$d_6$): δ12.1 (5-Me), 23.1 ($CH_2$), 23.5 ($CH_2$), 24.4 ($CH_2$), 34.0 ($CH_2$), 36.1 ($CH_2$), 60.7 and 62.8 (both $CH_2$, 5''- and 6'-C), 81.1 (3'-C), 83.2 (2'-C), 88.4 (4'-C), 89.1 (1'-C), 109.5 (5-C), 113.5 (quaternary C of CyH), 136.9 (6-C), 150.5 (2-C), and 163.6 (4-C).

[Purification via a Sodium Salt (No. 1)]

Synthesis of a Sodium Salt of 2',3'-O-cyclohexylidene-4'-C-hydroxymethyl-5-methyluridine (Compound (5-1))

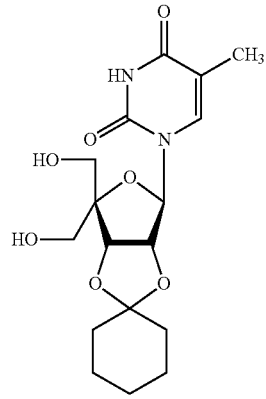

Compound (5-1)

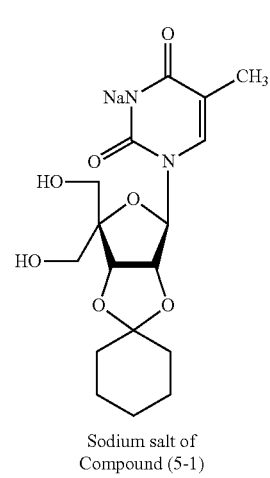

Sodium salt of Compound (5-1)

Compound (5-1) (150 mg, 0.41 mmol) obtained in Step 3 was dissolved in acetonitrile (5 mL). To this, a 28% solution of sodium methoxide in methanol (71 mg, 0.37 mmol) was added with stirring at room temperature. After stirring at room temperature for 1 hour, precipitated crystal was recovered by filtration, washed with acetonitrile (2 mL), and air-dried at room temperature for 12 hours to give a purified sodium salt of Compound (5-1) as a white crystal (114 mg, yield: 71%).

(Properties)

$^1$H-NMR (200 MHz, DMSO-$d_6$): δ 1.28-1.76 (10H, m, 5×CH$_2$), 1.69 (3H, d, J=0.9 Hz, 5-Me), 3.40-3.65 (4H, m, 5'- and 6'-H$_2$), 4.71 (1H, br s, OH), 4.79 (1H, A part of ABX, J$_{AB}$=6.2 Hz, J$_{AX}$=0 Hz, 3'-H), 4.94 (1H, B part of ABX, J$_{AB}$=6.2 Hz, J$_{BX}$=4.5 Hz, 2'-H), 5.47 (1H, br s, OH), 5.79 (1H, d, J=4.5 Hz, 1'-H), and 7.33 (1H, br s, 6-H). IR (KBr) cm$^{-1}$: 3418, 2937, 2860, 1662, 1611, 1519, 1466, 1449, 1368, 1098, 1072.

[Purification via a Potassium Salt]

Synthesis of a potassium salt of 2',3'-O-cyclohexylidene-4'-C-hydroxymethyl-5-methyluridine (Compound (5-1))

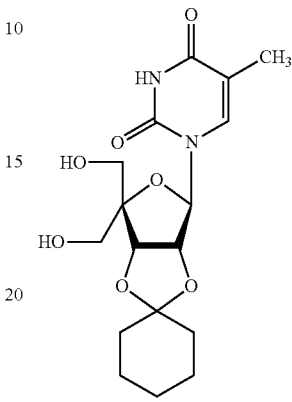

Compound (5-1)

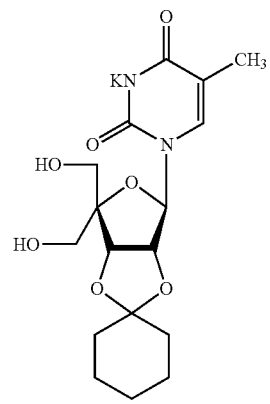

Potassium salt of Compound (5-1)

Compound (5-1) (9.75 g, 25.5 mmol) obtained in Step 3 was dissolved in acetone (195 mL). To this, a KOH-methanol solution (KOH (1.48 g, 26.4 mmol) was dissolved in methanol (10 mL)) was added with stirring at room temperature. After stirring at the same temperature for 1 hour, precipitated crystal was recovered by filtration, washed with acetone (20 mL), and dried under reduced pressure at 40° C. for 16 hours to give a purified potassium salt of Compound (5-1) as a white crystal (9.10 g, yield: 85%).

(Properties)

$^1$H-NMR (200 MHz, DMSO-$d_6$): δ 1.24-1.76 (10H, m, 5×CH$_2$), 1.67 (3H, unresolved d, 5-Me), 3.40-3.65 (4H, m, 5'- and 6'-H$_2$), 4.5-6.0 (2H, br, 2×OH), 4.80 (1H, A part of ABX, J$_{AB}$=6.2 Hz, J$_{AX}$=0 Hz, 3'-H), 4.98 (1H, B part of ABX, J$_{AB}$=6.2 Hz, J$_{BX}$=4.2 Hz, 2'-H), 5.72 (1H, d, J=4.2 Hz, 1'-H), and 7.31 (1H, br s, 6-H). IR (KBr) cm$^{-1}$: 3407, 2936, 2860, 1663, 1611, 1520, 1465, 1449, 1368, 1099, 1072.

[Purification via a Sodium Salt (No. 2)]

Purification of 2',3'-O-cyclohexylidene-4'-C-hydroxymethyl-5-methyluridine (Compound (5-1)) via a sodium salt of 2',3'-O-cyclohexylidene-4'-C-hydroxymethyl-5-methyluridine (Compound (5-1))

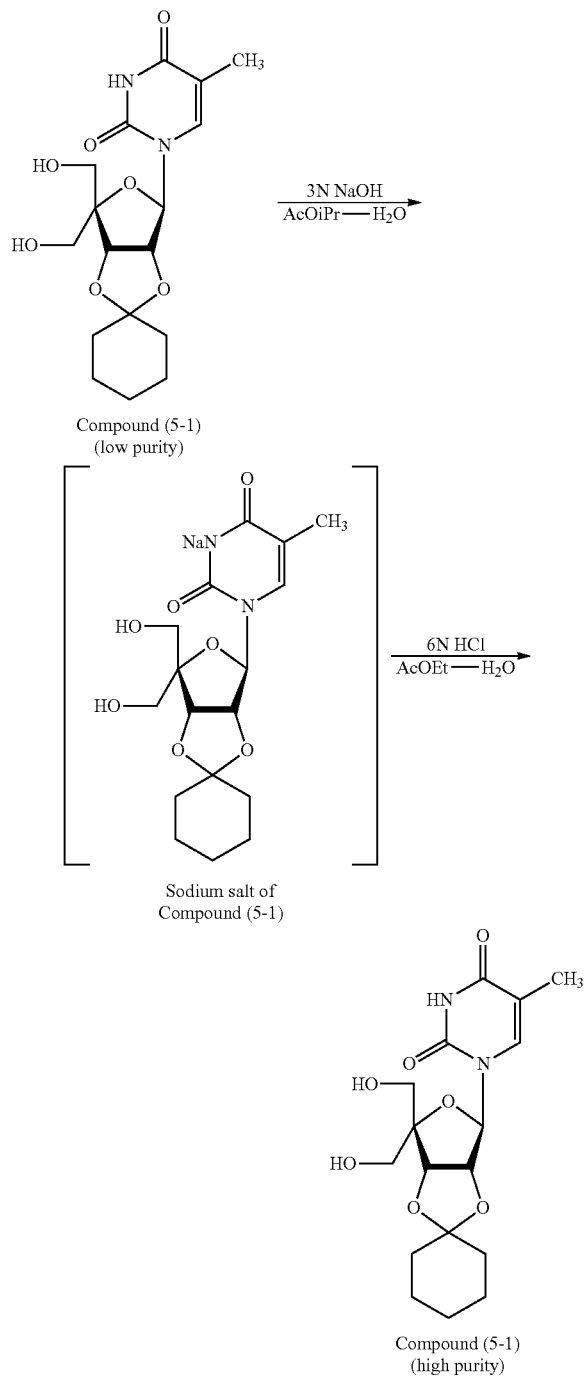

To the concentrated aqueous solution (171 mL, containing 14.5 g (net amount) of Compound (5-1)) obtained after the sodium borohydride reduction reaction in Step 3, isopropyl acetate (80 mL) was added to dissolve solids (two-layer solution system consisting of 95 mL of organic layer and 156 mL of aqueous layer). To this, with stirring at room temperature, 3N NaOH aqueous solution (24.5 mL) was added to adjust the pH to 10.0. After recovering the aqueous layer, water (20 mL) was added to the organic layer, and 3N NaOH aqueous solution (1.0 mL) was added to adjust the pH to 10.5. After recovering the aqueous layer again, water (20 mL) was added to the organic layer, and 3N NaOH aqueous solution (0.5 mL) was added to adjust the pH to 10.5. After recovering the aqueous layer, all the aqueous layers were combined, 6N hydrochloric acid (16 mL) was added to adjust the pH to 7.5, and then sodium chloride (30 g) was dissolved for salting-out. Ethyl acetate (80 mL) was added thereto for extraction, and the organic layer was recovered. After the aqueous layer was further extracted with ethyl acetate (80 mL) twice, combined organic layers were washed with an aqueous sodium chloride solution (prepared by dissolving NaCl (6.0 g) in water (20 mL)), dried with magnesium sulfate, and concentrated to give a highly purified Compound (5-1) (33.6 g, containing 12.2 g (net amount) of Compound (5-1)). The purity of the obtained Compound (5-1) was 77.63%. The HPLC analysis results of the Compound (5-1) before and after purification are shown in Table 1.

TABLE 1

| | uk | uk | Compound (5-1) | uk | uk | CMTE |
|---|---|---|---|---|---|---|
| RRT | 0.35 | 0.81 | 1.00 | 1.06 | 1.17 | 1.33 |
| Before purification | 0.35% | 2.07% | 58.13% | 3.05% | 2.65% | 9.05% |
| After purification | 0.12% | 0.49% | 77.63% | 2.93% | 1.12% | 0.60% |

In the Table 1, RRT (ratio of retention time) means the relative retention time on HPLC and uk means an impure substance whose structure is unknown.

The Table 1 shows that the purification process using the sodium salt of 2',3'-O-cyclohexylidene-4'-C-hydroxymethyl-5-methyluridine (Compound (5-1)) efficiently removed CMTE accounting for a large part of impurities to give a highly purified Compound (5-1).

[Step 4]

Synthesis of 2',3'-O-cyclohexylidene-5-methyl-4'-C-[(trityl)oxymethyl]-uridine (Compound (6-1))

To a solution of Compound (5-1) (368 mg, 1.00 mmol) in DMF (3.7 mL), N,N-dimethyl-4-aminopyridine (DMAP) (12 mg, 0.10 mmol), triethylamine (293 μl, 2.10 mmol), and chloro triphenylmethane (trityl chloride) (558 mg, 2.00 mmol) were added at room temperature, and the mixture was stirred at 20° C. for 25 hours. After ethyl acetate (3.7 mL) and water (3.7 mL) were added and the mixture was stirred, the organic layer was recovered, and the aqueous layer was re-extracted with ethyl acetate (3.7 mL). Combined organic layers were dried with magnesium sulfate. After filtration, concentration under reduced pressure gave a crude product of Compound (6-1) (1.23 g) as an oily residual material (quantitative value of Compound (6-1) by HPLC: 541 mg, yield: 88%).

(Properties)

2',3'-O-cyclohexylidene-5-methyl-4'-C-[(trityl)oxymethyl]-uridine $^1$H-NMR (200 MHz, DMSO-$d_6$): δ 1.15-1.70 (10H, m, 5×$CH_2$), 1.79 (3H, d, J=0.9 Hz, 5-Me), 3.11 (2H, br s, 6'-$H_2$), 3.68 (1H, A part of ABX, $J_{AB}$=11.7 Hz, JAX=4.9 Hz, one of 5'-$H_2$), 3.75 (1H, B part of ABX, $J_{AB}$=11.7 Hz, $J_{BX}$=4.9 Hz, one of 5'-$H_2$), 4.87 (1H, A part of ABX, $J_{AB}$=6.5 Hz, $J_{AX}$=0 Hz, 3'-H), 4.87 (1H, B part of ABX, $J_{AB}$=6.5 Hz, $J_{BX}$=2.9 Hz, 2'-H), 5.29 (1H, br t, J=4.9 Hz, 5'-OH), 5.89 (1H, d, J=2.9 Hz, 1'-H), 7.20-7.46 (15H, m, ArH), 7.72 (1H, d, J=0.9 Hz, 6-H), and 11.37 (1H, br s, 3-H).
$^{13}$C-NMR (50.3 MHz, DMSO-d$_6$): δ 12.1 (5-Me), 23.1 (CH$_2$), 23.3 (CH$_2$), 24.3 (CH$_2$), 33.9 (CH$_2$), 35.6 (CH$_2$), 62.8 and 62.9 (both CH$_2$, 5'- and 6'-C), 80.9 and 83.2 (both CH, 2'-C and 3'-C), 86.0 and 87.7 (both quaternary C, 4'-C and quaternary C of Tr), 88.7 (1'-C), 109.7 (5-C), 113.7 (quaternary C of CyH), 126.9 (ArC), 127.8 (ArC), 128.2 (ArC), 136.9 (6-C), 143.7 (quaternary ArC), 150.4 (2-C), and 163.6 (4-C).

Synthesis of 2',3'-O-cyclohexylidene-5-methyl-5'-O-pivaloyl-4'-C-[(trityl)oxymethyl]uridine compound (Compound (7-1))

To a solution of Compound (6-1) (610.7 mg, 1.00 mmol) in pyridine (6.1 mL), trimethyl acetyl chloride (pivaloyl chloride) (246 μL, 2.00 mmol) was added at room temperature, and the mixture was stirred for 15 hours. Then, methanol (350 μL) was added at the room temperature, and the mixture was stirred for 6 hours. After ethyl acetate (9.2 mL) was added thereto, the mixture was washed twice with 4N hydrochloric acid (8 mL) under cooling in an ice bath. The mixture was dried with magnesium sulfate, filtered, and then concentrated under reduced pressure to give an oily residual material (795 mg). Purifying this residual material by silica gel column chromatography (silica gel: 15 g, heptane:ethyl acetate=3:2 (v/v)→1:1 (v/v)) gave the title compound (7-1) (679 mg, yield: 98%) as an oily material.
(Properties)

2',3'-O-cyclohexylidene-5-methyl-5'-pivaloyl-4'-C-[(trityl)oxymethyl]uridine $^1$H-NMR (200 MHz, DMSO-d$_6$): δ 1.01 (9H, s, 3×Me of Pv), 1.19-1.59 (10H, m, 5×CH$_2$), 1.80 (3H, d, J=1.1 Hz, 5-Me), 2.98 and 3.21 (1H each, ABq, J=10.3 Hz, 6'-H$_2$), 4.29 and 4.43 (1H each, ABq, J=10.6 Hz, 5'-H$_2$), 4.83 (1H, d, J=6.7 Hz, 3'-H), 5.07 (1H, dd, J=6.7, 3.0 Hz, 2'-H), 5.88 (1H, d, J=3.0 Hz, 1'-H), 7.22-7.45 (15H, m, ArH), 7.56 (1H, d, J=1.1 Hz, 6-H), and 11.47 (1H, br s, 3-H). $^{13}$C-NMR (50.3 MHz, DMSO-d$_6$):
δ 11.8 (5-Me), 22.9 (CH$_2$), 23.2 (CH$_2$), 24.2 (CH$_2$), 26.5 (3×Me of Pv), 33.5 (CH$_2$), 34.9 (CH$_2$), 38.1 (quaternary C of Pv), 61.9 and 63.3 (both CH$_2$, 5'- and 6'-C), 81.5 and 82.9 (both CH, 2'- and 3'-C), 85.5 and 85.9 (both quaternary C, 4'-C and quaternary C of Tr), 89.3 (—C), 110.0 (5-C), 114.3 (quaternary C of CyH), 126.9 (ArC), 127.8 (ArC), 128.1 (ArC), 137.4 (6-C), 143.5 (quaternary ArC), 150.3 (2-C), 163.6 (4-C), and 176.7 (C=O of Pv).

Synthesis of 2',3'-O-cyclohexylidene-4'-C-(hydroxymethyl)-5-methyl-5'-O-pivaloyluridine (Compound (8-1))

To a solution of Compound (7-1) (1.18 g, 1.70 mmol) in methanol (12 mL), p-toluenesulfonic acid monohydrate (97 mg, 0.51 mmol) was added, and the mixture was stirred at room temperature for 7 hours. After a saturated aqueous solution of sodium hydrogencarbonate (12 mL) was added thereto, methanol was distilled off under reduced pressure. After extraction with ethyl acetate (2×12 mL), concentration under reduced pressure gave an oily residual material (1.35 g). Purification by silica gel column chromatography (silica gel: 20 g, heptane:ethyl acetate=5:4 (v/v)→4:5 (v/v)) gave the title compound (8-1) (707 mg, yield: 92%) as an oily material.
(Properties)

2',3'-O-cyclohexylidene-4'-C-(hydroxymethyl)-5-methyl-5'-O-pivaloyluridine $^1$H-NMR (200 MHz, DMSO-d$_6$): δ1.15 (9H, s, 3×Me of Pv), 1.26-1.81 (10H, m, 5×CH$_2$), 1.77 (3H, d, J=1.2 Hz, 5-Me), 3.58 (2H, br d, J=5.5 Hz, 6'-H$_2$), 4.14 and 4.23 (1H each, ABq, J=11.2 Hz, 5'-H$_2$), 4.79 (1H, d, J=6.6 Hz, 3'-H), 4.82 (1H, t, J=5.5 Hz, 6'-OH), 5.06 (1H, dd, J=6.6, 3.3 Hz, 2'-H), 5.83 (1H, d, J=3.3 Hz, 1'-H), 7.47 (1H, d, J=1.2 Hz, 6-H), and 11.42 (1H, br s, 3-H). $^{13}$C-NMR (50.3 MHz, DMSO-d$_6$):
δ 11.8 (5-Me), 23.1 (CH$_2$), 23.5 (CH$_2$), 24.3 (CH$_2$), 26.7 (3×Me of Pv), 33.6 (CH$_2$), 35.4 (CH$_2$), 38.2 (quaternary C of Pv), 60.1 and 63.9 (both CH$_2$, 5'- and 6'-C), 81.0 and 83.2 (both CH, 2'- and 3'-C), 86.6 (4'-C), 90.0 (1'-C), 109.5 (5-C), 114.0 (quaternary C of CyH), 137.0 (6-C), 150.3 (2-C), 163.6 (4-C), and 176.9 (C=O of Pv).
[Step 5]

Synthesis of 2',3'-O-cyclohexylidene-4'-C-formyl-5-methyl-5'-O-pivaloyl-uridine (Compound (9-1))

Compound (8-1) (4.11 g, 9.08 mmol) was dissolved in DMSO (25 mL) at room temperature, WSC (6.96 g, 36.33 mmol) and PPTS (2.28 g, 9.08 mmol) were added thereto, and the mixture was stirred at the same temperature for 1.5 hours. After toluene (41 mL) was added, the mixture was stirred and then washed with a saturated sodium hydrogencarbonate aqueous solution (41 mL), 1N hydrochloric acid (9 mL) and a saturated sodium chloride aqueous solution (41 mL). The organic layer was dried with magnesium sulfate, filtered, and then concentrated under reduced pressure to give the title compound (9-1) as a colorless amorphous material (3.69 g, yield: 90%).
(Properties)
$^1$H-NMR (200 MHz, DMSO-d$_6$)
δ 1.05 (9H, s, 3×Me of Pv), 1.25-1.64 (10H, m, 5×CH$_2$), 1.765 (3H, d, J=1.1 Hz, 5-Me), 4.48 and 4.57 (1H each, ABq, J=11.7 Hz, 5'-H$_2$), 5.09 (1H, d, J=6.3 Hz, 3'-H), 5.28 (1H, dd, J=6.3, 1.7 Hz, 2'-H), 6.00 (1H, d, J=1.7 Hz, 1'-H), 7.64 (1H, d, J=1.1 Hz, 6-H), 9.52 (1H, s, CHO), and 11.47 (1H, br s, 3-H).
[Purification via a Hydrogen Sulfite Adduct]

Purification of 2',3'-O-cyclohexylidene-4'-C-formyl-5-methyl-5'-O-pivaloyl-uridine (Compound (9-1)) via a hydrogen sulfite adduct of 2',3'-O-cyclohexylidene-4'-C-formyl-5-methyl-5'-O-pivaloyl-uridine (Compound (9-1))

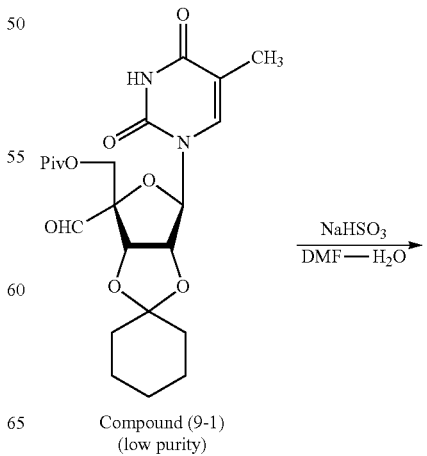

Compound (9-1)
(low purity)

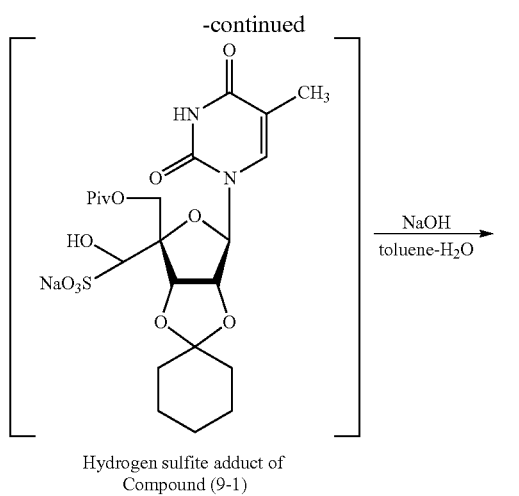

Hydrogen sulfite adduct of Compound (9-1)

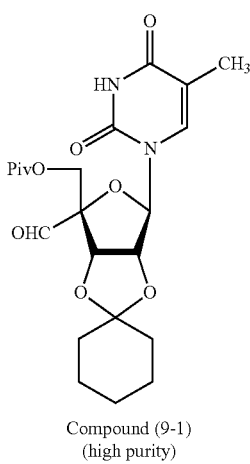

Compound (9-1)
(high purity)

(147 g) was dissolved in the aqueous layer, and toluene (340 mL) was added thereto. With vigorous stirring, a 48% sodium hydroxide aqueous solution (16.5 mL) was added to adjust the pH to 9.4.

Since the pH did not fall even after 30 minutes of stirring, 6N hydrochloric acid was added to adjust the pH to 9.0, and then the organic layer was recovered. After readjusting the pH of the aqueous layer to 9.0 with a 48% sodium hydroxide aqueous solution (0.5 mL), the aqueous layer was further extracted with toluene (340 mL) twice. Combined organic layers were washed with water (340 mL) twice, and then the solvent was distilled off under reduced pressure to give a yellow semisolid (150 g). After ethyl acetate (245 mL) was added thereto, the mixture was heated to a temperature ranging from 70 to 80° C. to give a homogenized solution, and then left to stand for cooling. At 40° C., a seed crystal of CPA was added, and the solution was further cooled to room temperature (30° C. or lower). After 1 hour of stirring at the same temperature, n-heptane (368 mL) was added thereto and stirring was continued for additional 1 hour. Precipitated crystal was recovered by filtration, washed with a mixed solvent (75 mL) of ethyl acetate/n-heptane (2/1), and dried in vacuo (50° C., 12 hours) to give a highly purified Compound (9-1) (33.4 g, 68.1%) as a white crystalline powder. The purity of the obtained Compound (9-1) was 89.07%. The HPLC analysis results of the Compound (9-1) before and after purification are shown in Table 2.

TABLE 2

|  | uk | Compound (9-1) | uk | epi-CPA | CPTE | uk | uk |
|---|---|---|---|---|---|---|---|
| RRT | 0.79 | 1.00 | 1.11 | 1.21 | 1.57 | 1.89 | 2.87 |
| Before Purification | 5.14% | 26.03% | 3.31% | 8.80% | 5.57% | 4.70% | 12.20% |
| After Purification | 0.96% | 89.07% | 0.02% | 1.26% | 0.06% | 0.10% | N.D. |

The recrystallization mother liquid of Compound (9-1) obtained in Step 5 was concentrated under reduced pressure to give a low purity Compound (9-1) (267 g, containing 49.0 g (0.109 mol) (net amount) of Compound (9-1), a little ethyl acetate and n-heptane) comprising an insoluble substance. This low purity compound was dissolved in DMF (590 mL), and ethyl acetate and n-heptane were nearly completely distilled off under reduced pressure. To this, a sodium bisulfite aqueous solution (prepared by dissolving $NaHSO_3$ (34.0 g, 0.327 mol) in water (590 mL)) was added dropwise at room temperature (30° C. or lower) over 12 minutes. After stirring at the same temperature for 3.5 hours, raw material was detected in the reaction mixture by HPLC analysis (pH was 4.9 at this point). Therefore, 6N hydrochloric acid (13.6 mL) was added to adjust the pH to 3.0, and stirring was continued for additional 30 minutes. After the reaction mixture was washed with ethyl acetate (340 mL) twice, sodium chloride In the Table 2, RRT (ratio of retention time) means the relative retention time on HPLC, uk means an impure substance whose structure is unknown, and N.D. means "not detectable".

The Table 2 shows that the purification process of 2',3'-O-cyclohexylidene-4'-C-formyl-5-methyl-5'-O-pivaloyl-uridine (Compound (9-1)) via a hydrogen sulfite adduct thereof efficiently removed impurities, such as epi-CPA and CPTE to give a highly purified Compound (9-1).

[Step 6]

Synthesis of (Z)-4'-C-(2-chloroethenyl)-2',3'-O-cyclohexylidene-5-methyl-5'-O-pivaloyluridine (Compound (10-1))

To a suspension of chloromethyl triphenyl phosphonium chloride (8.53 g, 24.57 mmol) in THF (37 mL) cooled to −30° C., butyl lithium (1.6 M hexane solution, 15.4 mL, 24.57 mmol) was added dropwise. After the mixture was stirred at −30° C. for 90 minutes, a solution of Compound (9-1) (3.69 g, 8.19 mmol) in THF (18 mL) was added dropwise at −30° C. After the mixture was stirred at the same temperature for 2 hours, a saturated ammonium chloride solution (37 mL) was added dropwise. After THF and hexane were distilled off under reduced pressure, the residual solution was extracted with ethyl acetate (2×37 mL). From combined organic layers, the solvent was distilled off under reduced pressure to give a semisolid residual material (8.23 g). Silica gel column chromatography (silica gel: 90 g, heptane:ethyl acetate=2:1 (v/v)→1:1 (v/v)) purified this, and the title compound (10-1) (3.65 g, a yield: 92%) was obtained as white powdery material.

(Properties)

$^1$H-NMR (200 MHz, DMSO-$d_6$):

δ 1.135 (9H, s, 3 in vacuo Me of Pv), 1.26-1.80 (10H, m, 5×CH$_2$), 1.775 (3H, d, J=1.1 Hz, 5-Me), 4.29 and 4.37 (1H each, ABq, J=11.4 Hz, 5'-H$_2$), 4.88 (1H, d, J=6.6 Hz, 3'-H), 5.09 (1H, dd, J=6.6, 3.1 Hz, 2'-H), 5.88 (1H, d, J=3.1 Hz, 1'-H), 5.96 (1H, d, J=8.2 Hz, ClCH=CH—), 6.54 (1H, d, J=8.2 Hz, ClCH=CH—), 7.52 (1H, d, J=1.1 Hz, 6-H), and 11.46 (1H, br s, 3-H).

$^{13}$C-NMR (50.3 MHz, DMSO-$d_6$):

δ 11.9 (5-Me), 23.2 (CH$_2$), 23.6 (CH$_2$), 24.4 (CH$_2$), 26.7 (3×Me of Pv), 34.0 (CH$_2$), 35.4 (CH$_2$), 65.7 (5'-C), 81.5 (3'-C), 82.8 (2'-C), 86.8 (4'-C), 89.9 (1'-C), 109.8 (5-C), 114.8 (quaternary C of CyH), 120.2 (ClHC=CH—), 127.9 (ClHC=CH—), 137.4 (6-C), 150.3 (2-C), 163.7 (4-C), and 177.0 (C=O of Pv).

[Step 7]

Synthesis of (Z)-4'-C-(2-chloroethenyl)-5-methyl-5'-O-pivaloyluridine (Compound (11-1))

To a solution of Compound (10-1) (483.2 mg, 1.00 mmol) in methanol (14.2 mL) and tetrahydrofuran (THF) (7.0 mL), concentrated hydrochloric acid (10.5 mL) was added dropwise at room temperature, and the mixture was stirred at the same temperature for 1 hour. After ice cooling, a 20 (w/w) % sodium hydroxide aqueous solution (21 mL) was added to neutralize the reaction mixture, and methanol and THF were distilled off under reduced pressure. To the residual liquid, water (15 mL) and ethyl acetate (20 mL) were added, and the organic layer was recovered. The aqueous layer was further extracted with ethyl acetate (10 mL). Combined organic layers were concentrated under reduced pressure. Purification of the obtained crude product by silica gel column chromatography (silica gel: 15 g, ethyl acetate) gave the title compound (11-1) (391.4 mg, yield: 97%) as a white amorphous material.

(Properties)

$^1$H-NMR (200 MHz, DMSO-$d_6$): δ 1.16 (9H, s, 3×Me of Pv), 1.795 (3H, d, J=1.1 Hz, 5-Me), 4.14 (1H, t, J=5.7 Hz, 3'-H), 4.22 (1H, q, J=5.7 Hz, 2'-H), 4.26 and 4.33 (1H each, ABq, J=11.7 Hz, 5'-H2), 5.47 (1H, d, J=5.7 Hz, OH), 5.52 (1H, d, J=5.7 Hz, OH), 5.85 (1H, d, J=5.7 Hz, 1'-H), 5.99 (1H, d, J=8.1 Hz, ClCH=CH—), 6.46 (1H, d, J=8.1 Hz, ClCH=CH—), 7.40 (1H, d, J=1.1 Hz, 6-H), and 11.39 (1H, br s, 3-H).

$^{13}$C-NMR (50.3 MHz, DMSO-$d_6$):

δ 11.9 (5-Me), 26.8 (3×Me of Pv), 64.9 (5'-C), 71.3 and 72.0 (both CH, 2'- and 3'-C), 84.8 (quaternary C, 4'-C), 87.9 (1'-C), 110.0 (5-C), 120.0 (ClHC=CH—), 128.3 (ClHC=CH—), 136.4 (6-C), 150.6 (2-C), 163.6 (4-C), and 177.1 (C=O of Pv).

[Step 8]

Synthesis of (Z)-3'-O-acetyl-2'-α-bromo-4'-C-(2-chloroethenyl)-5'-O-pivaloyluridine (Compound (12-1))

Compound (11-1) (319 mg, 0.792 mmol) was dissolved in acetic acid (640 μL), and the solution was heated to 50° C. To this, trimethyl orthoacetate (175 μL, 1.40 mmol) was added dropwise. The mixture was stirred at 50° C. for 1 hour. Acetic acid in the reaction mixture was distilled off under reduced pressure. After addition of 2.6 mL of acetonitrile, the reaction mixture was heated to 50° C. After addition of acetic anhydride (189 μL, 2.00 mmol), acetyl bromide (89 μL, 1.20 mmol) was added dropwise, and the mixture was stirred at 50° C. for 46 hours. The reaction mixture was ice-cooled, 640 μL of water was added, and a 1.8 mL of 20 (w/w) % sodium hydroxide aqueous solution was added to adjust the pH to 6.5. The reaction mixture was extracted with ethyl acetate (3 mL) twice, and the organic layer was concentrated under reduced pressure. The obtained crude product was separated and purified by silica gel chromatography to give the title compound (12-1) (348 mg, yield: 87%).

(Properties)

$^1$H-NMR (200 MHz, DMSO-$d_6$):

δ 1.15 (9H, s, 3×Me of Pv), 1.81 (3H, d, J=1.0 Hz, 5-Me), 2.14 (3H, s, Me of Ac), 4.39 and 4.44 (1H each, ABq, J=11.8 Hz, 5'-H$_2$) 5.21 (1H, dd, J=8.6, 5.7 Hz, 2'-H), 5.56 (1H, d, J=5.7 Hz, 3'-H), 5.91 (1H, d, J=8.1 Hz, ClCH=CH—), 6.31 (1H, d, J=8.6 Hz, 1'-H), 6.61 (1H, d, J=8.1 Hz, ClCH=CH—), 7.54 (1H, d, J=1.0 Hz, 6-H), and 11.57 (1H, br s, 3-H).

$^{13}$C-NMR (50.3 MHz, DMSO-$d_6$):

δ 12.0 (5-Me), 20.4 (Me of Ac), 26.7 (3×Me of Pv), 46.2 (2'-C), 65.1 (5'-C), 72.2 (3'-C), 84.7 (quaternary C, 4'-C), 87.9 (1'-C), 110.8 (5-C), 121.9 (ClHC=CH—), 126.9 (ClHC=CH—), 135.6 (6-C), 150.5 (2-C), 163.4 (4-C), 168.7 (C=O of Ac), and 176.9 (C=O of Pv).

[Step 9]

Synthesis of (Z)-4'-C-(2-chloroethenyl)-2',3'-didehydro-3'-deoxy-5'-O-pivaloyl thymidine (Compound (13-1))

EDTA.2Na.2H$_2$O (13.4 g) was suspended in water (50 mL), and a 20 (w/w) % sodium hydroxide aqueous solution was added thereto for adjusting the pH to 7.9 to give an EDTA aqueous solution.

Zinc powder (773 mg, 11.8 mmol) was suspended in DMSO (6 mL), and 1,2-dibromoethane (102 μL, 0.50 mmol) was added dropwise at room temperature. The reaction mixture was heated to 60° C. and stirred for 3 minutes. After cooling to room temperature, a solution of Compound (12-1) (1.20 g, 2.36 mmol) in DMSO (6 mL) was added dropwise. After 1 hour of stirring at room temperature, the reaction mixture was further stirred at 40° C. for additional 1 hour. After ethyl acetate (12 mL) was added thereto, the mixture was ice-cooled, and then the above-mentioned EDTA aqueous solution (6 mL) was added. After water (12 mL) was added and the mixture was stirred, the organic layer was recovered, and the aqueous layer was re-extracted with ethyl acetate (12 mL). Combined organic layers were washed with a saturated aqueous solution of sodium chloride (6 mL), dried with magnesium sulfate, filtered, and then concentrated under reduced pressure. Separation and purification of the obtained crude product by silica gel column chromatography (silica gel: 8 g, heptane:ethyl acetate=1:1 (v/v)) gave the title compound (13-1) (562 mg, yield: 65%) as a white powder.
(Properties)
$^1$H-NMR (200 MHz, DMSO-$d_6$)
δ 1.14 (9H, s, 3×Me of Pv), 1.785 (3H, d, J=1.2 Hz, 5-Me), 4.29 and 4.34 (1H each, ABq, J=11.7 Hz, 5'-H$_2$), 6.06 (1H, d, J=7.9 Hz, ClCH═CH—), 6.14 (1H, dd, J=5.9, 1.3 Hz, 3'-H), 6.47 (1H, d, J=7.9 Hz, ClCH═CH—), 6.56 (1H, dd, J=5.9, 2.0 Hz, 2'-H), 6.87 (1H, dd, J=2.0, 1.3 Hz, 1'-H), 7.27 (1H, q-like d, J=1.2 Hz, 6-H), and 11.44 (1H, br s, 3-H).
$^{13}$C-NMR (50.3 MHz, DMSO-$d_6$):
δ 11.9 (5-Me), 26.7 (3×Me of Pv), 66.5 (5'-C), 89.4 (1'-C), 90.0 (4'-C), 109.7 (5-C), 119.5 (ClHC═CH—), 126.9 (ClHC═CH—), 130.8 and 133.5 (2'- and 3'-C), 135.6 (6-C), 150.6 (2-C), 163.6 (4-C), 176.9 (C═O of Pv).

[Step 10a]

Synthesis of 2',3'-didehydro-3'-deoxy-4-ethynylthymidine (Compound (1))

To a solution of Compound (13-1) (150 mg, 0.41 mmol) in THF (4.5 mL), chloro trimethylsilane (77 µL, 0.61 mmol) was added dropwise at −30° C. Further, 2.0 M lithium diisopropylamide (LDA) solution (249 µL, 0.45 mmol) was added dropwise, and the mixture was stirred at the same temperature for 1 hour. Then, 2.0 M LDA solution (497 µL, 0.90 mmol) was added dropwise again, and stirring was continued for 3 hours. Further, the LDA solution (2.0 M, 249 µL, 0.45 mmol) was added dropwise at −30° C., and stirring was continued at the same temperature for 1 hour. To the reaction mixture, a saturated ammonium chloride solution (1.5 mL) was added. After stirring, 3N sodium hydroxide aqueous solution (3 mL) and methanol (2 mL) were added. After 2 hours of stirring at room temperature, 4N hydrochloric acid was added to adjust to the pH to 6.0, and then the organic solvent was distilled off under reduced pressure. The aqueous residual liquid was extracted with ethyl acetate, dried with magnesium sulfate, and then concentrated under reduced pressure. Purification of the obtained crude product by silica gel column chromatography (silica gel: 10 g, chloroform:methanol=19:1 (v/v)→ ethyl acetate) gave TKD (21 mg, yield: 21%) as a white crystal.
(Properties)
$^1$H-NMR (200 MHz, DMSO-$d_6$):
δ 1.71 (3H, d, J=1.3 Hz, 5-Me), 3.60 (1H, A part of ABX, $J_{AB}$=12.1 Hz, $J_{AX}$=6.4 Hz, one of 5'-H$_2$), 3.67 (1H, s, acetylenic H), 3.69 (1H, B part of ABX, $J_{AB}$=12.1 Hz, $J_{BX}$=5.7 Hz, one of 5'-H$_2$), 5.48 (1H, br t-like, 5'-OH), 6.06 (1H, dd, J=5.9, 1.3 Hz, 3'-H), 6.36 (1H, dd, J=5.9, 2.0 Hz, 2'-H), 6.89 (1H, dd, J=2.0, 1.3 Hz, 1'-H), 7.58 (1H, q-like, J=1.3 Hz, 6-H), and 11.37 (1H, br s, 3-H).
$^{13}$C-NMR (50.3 MHz, DMSO-$d_6$):
δ 12.1 (5-Me), 65.7 (5'-C), 77.3 (HCC—), 81.4 (HCC—), 86.5 (4'-C), 88.9 (1'-C), 109.0 (5-C), 127.1 (3'-C), 135.5 (2'-C), 136.7 (6-C), 150.8 (2-C, C═O), 163.8 (4-C, C═O).

Example 2

Production of 2',3'-didehydro-3'-deoxy-4'-ethynylthymidine

Embodiment 2

Steps 1 to 9 were performed in the same manner as in the Example 1, and subsequently the following Steps 10b to 13 were performed to synthesize the title compound.

[Step 10b]

Synthesis of (Z)-4'-C-(2-chloroethenyl)-2',3'-didehydro-3'-deoxy-thymidine (Compound (14-1))

To a suspension of Compound (13-1) (562 mg, 1.52 mmol) in methanol (5.6 mL), 10% sodium hydroxide aqueous solution (1.4 mL) was added at room temperature, and the mixture was stirred at the same temperature for 2 hours. After 4N hydrochloric acid (0.9 mL) was added for neutralization, methanol was distilled off under reduced pressure. To the residual liquid, ethyl acetate (5.6 mL) was added, and the organic layer was recovered. The aqueous layer was further extracted with ethyl acetate (5.6 mL). Combined organic layers were dried with magnesium sulfate, and then concentrated under reduced pressure to give the title compound (14-1) as a white powder (431 mg, yield: 99%).
(Properties)
$^1$H-NMR (200 MHz, DMSO-$d_6$):
δ 1.725 (3H, d, J=1.1 Hz, 5-Me), 3.55 and 3.75 (1H each, ABq, J=11.8 Hz, 5'-H$_2$), 5.36 (1H, br, OH), 5.99 (1H, dd, J=5.9, 1.3 Hz, 3'-H), 6.00 (1H, d, J=7.9 Hz, ClCH═CH—), 6.39 (1H, d, J=7.9 Hz, ClCH═CH—), 6.51 (1H, dd, J=5.9, 2.0 Hz, 2'-H), 6.92 (1H, dd, J=2.0, 1.3 Hz, 1'-H), 7.74 (1H, q-like d, J=1.1 Hz, 6-H), and 11.31 (1H, br, 3-H).
$^{13}$C-NMR (50.3 MHz, DMSO-$d_6$):
δ 12.0 (5-Me), 64.3 (5'-C), 88.7 (1'-C), 92.9 (4'-C), 108.7 (5-C), 118.9 (ClHC═CH—), 126.2 (ClHC═CH—), 131.6 and 134.6 (2'- and 3'-C), 136.9 (6-C), 150.8 (2-C), and 163.7 (4-C).

[Step 11a]

Synthesis of (Z)-4'-C-(2-chloroethenyl)-2',3'-didehydro-3'-deoxy-5'-O-trityl thymidine (Compound (15-1))

To a solution of Compound (14-1) (199 mg, 0.70 mmol) in DMF (3.7 mL), 4-(dimethylamino)pyridine (DMAP) (9 mg, 0.07 mmol), triethylamine (254 µL, 1.82 mmol), and chloro triphenylmethane (488 mg, 1.75 mmol) were added at 80° C., and the mixture was stirred at 80° C. for 15 hours. After ethyl acetate (2.0 mL) and water (3.0 mL) were added under cooling in an ice bath and the mixture was stirred, the organic layer was recovered, and then the aqueous layer was re-extracted with ethyl acetate (2.0 mL). Combined organic layers were washed with a saturated aqueous solution of sodium chloride (1.0 mL), dried with magnesium sulfate, filtered, and then concentrated under reduced pressure. Separation and purification of the obtained crude product (910 mg) by silica gel column chromatography (silica gel: 10 g, heptane:ethyl acetate=1:1 (v/v)) gave the title compound (15-1) (369 mg, yield: 100%) as a slightly yellow amorphous material.
(Properties)
$^1$H-NMR (200 MHz, DMSO-$d_6$):
δ 1.20 (3H, d, J=0.9 Hz, 5-Me), 3.22 and 3.39 (1H each, ABq, J=10.1 Hz, 5'-H2), 6.07 (1H, d, J=7.9 Hz, ClCH═CH—), 6.11 (1H, dd, J=5.9, 1.3 Hz, 3'-H), 6.37 (1H, d, J=7.9 Hz, ClCH═CH—), 6.70 (1H, dd, J=5.9, 2.0 Hz, 2'-H), 6.94 (1H, dd, J=2.0, 1.3 Hz, 1'-H), 7.23-7.41 (16H, m, 6-H and ArH), and 11.40 (1H, br s, 3-H).
$^{13}$C-NMR (50.3 MHz, DMSO-$d_6$)
δ 11.1 (5-Me), 66.8 (5'-C), 86.2 (quaternary C of Tr), 88.7 (1'-C), 91.3 (4'-C), 109.5 (5-C), 119.0 (ClHC═CH—), 126.2 (ClHC═CH—), 127.0 (ArC), 127.7 (ArC), 128.2 (ArC), 131.7 and 134.2 (2'- and 3'-C), 135.5 (6-C), 143.0 (ArC), 150.6 (2-C), and 163.5 (4-C).

[Step 12]

Synthesis of 2',3'-didehydro-3'-deoxy-4'-C-ethynyl-5'-O-trityl thymidine (Compound (16-1))

To a solution of Compound (15-1) (150 mg, 0.28 mmol) in THF (4.5 mL), butyl lithium (1.6 M hexane solution, 712 μL, 1.14 mmol) was added dropwise at −40° C. After the mixture was stirred at −40° C. for 2 hours, a saturated ammonium chloride solution (1.5 mL) was added dropwise. After THF and hexane were distilled off under reduced pressure, the residual solution was extracted with ethyl acetate (1.5 mL). The solvent of the organic layer was distilled off under reduced pressure. Purification of the obtained crude product (190 mg) by silica gel column chromatography (silica gel: 6 g, heptane:ethyl acetate=1:1 (v/v)) gave the title compound (16-1) (126 mg, yield: 90%) as a slightly yellow amorphous material.
(Properties)
$^1$H-NMR (200 MHz, DMSO-$d_6$): δ 1.17 (3H, d, J=1.2 Hz, 5-Me), 3.21 and 3.32 (1H each, ABq, J=9.8 Hz, 5'-H2), 3.70 (1H, s, acetylenic H), 6.18 (1H, dd, J=5.9, 1.3 Hz, 3'-H), 6.60 (1H, dd, J=5.9, 2.2 Hz, 2'-H), 6.90 (1H, dd, J=2.2, 1.3 Hz, 1'-H), 7.14 (1H, q-like d, J=1.2 Hz, 6-H), 7.25-7.42 (15H, m, ArH of Tr), and 11.42 (1H, br s, 3-H).
$^{13}$C-NMR (50.3 MHz, DMSO-$d_6$)
δ 11.1 (5-Me), 67.9 (5'-C), 77.1 (HCC—), 79.0 (quaternary C of Tr), 80.9 (HCC—), 86.3 (4'-C), 89.0 (1'-C), 109.7 (5-C), 126.3 (3'-C), 127.1 (ArC), 127.8 (ArC), 128.2 (ArC), 135.1 and 135.3 (2'- and 6-C), 142.8 (ArC), 150.5 (2-C), 163.4 (4-C).
[Step 13]

Synthesis of 2',3'-didehydro-3'-deoxy-4'-ethynylthymidine (Compound (1))

To a solution of Compound (16-1) (50 mg, 0.10 mmol) in methanol (1 mL), p-toluenesulfonic acid monohydrate (10 mg, 0.05 mmol) was added, and the mixture was stirred at room temperature for 6 hours. After a saturated aqueous solution of sodium hydrogencarbonate (1 mL) was added thereto, methanol was distilled off under reduced pressure. After extraction with ethyl acetate (3×3 mL), concentration under reduced pressure gave an oily residual material (51 mg). Purification by silica gel column chromatography (silica gel: 3 g, chloroform:methanol=19:1 (v/v)) gave TKD (24 mg, yield: 96%) as a white crystal.

Example 3

Production of 2',3'-didehydro-3'-deoxy-4'-ethynylthymidine

Embodiment 3

Steps 1 to 10b were performed in the same manner as in the Example 2, and subsequently the following Step 11b was performed to synthesize the title compound.
[Step 11b]

Synthesis of 2',3'-didehydro-3'-deoxy-4'-ethynylthymidine (Compound (1))

To a solution of Compound (14-1) (2.45 g, 8.61 mmol) in DMSO (25 mL), sodium tert-butoxide (993 mg, 10.3 mmol) was added with stirring at room temperature over 5 minutes. After stirring at room temperature for 40 minutes, 6N hydrochloric acid (2.0 mL) was added to neutralize the solution, and subsequently an aqueous sodium chloride solution (prepared by dissolving NaCl (36.9 g) in water (123 mL)) was added. After the reaction mixture was extracted with ethyl acetate (49 mL) 6 times, combined organic layers were washed with an aqueous sodium chloride solution (prepared by dissolving NaCl (3.69 g) in water (12.3 mL)), and dried with magnesium sulfate, and then the solvent was distilled off until a crystal began to precipitate. After stirring at room temperature for 30 minutes, toluene (61 mL) was added, and the mixture was heated to 65° C. or higher. Stirring was continued within the range of 65 to 78.1° C. for 30 minutes, and then the mixture was cooled to room temperature (30° C. or lower) and further stirred for 1 hour. Precipitated crystal was recovered by filtration, washed with a mixed solvent of ethyl acetate (1 mL) and toluene (5 mL), and air-dried at room temperature for 12 hours to give TKD (1.88 g, yield: 88%) as a light brown crystal.

The above results confirmed that the process of the present invention enables efficient production of 2',3'-didehydro-3'-deoxy-4'-ethynylthymidine.

INDUSTRIAL APPLICABILITY

The present invention provides a production process of chemically synthesizing 2',3'-didehydro-3'-deoxy-4'-ethynylthymidine, which is useful as a medicine, in an efficient and industrially advantageous manner.

We claim:

1. A process for producing 2',3'-didehydro-3'-deoxy-4'-ethynylthymidine represented by the Formula (1):

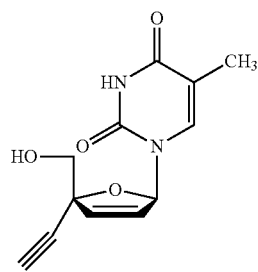

(1)

the process comprising the following Steps 1 to 10a.

[Step 1] selectively protecting the hydroxy groups at positions 2' and 3' in the compound represented by the following Formula (2):

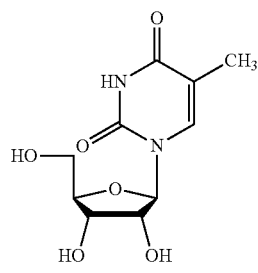

(2)

to obtain a compound represented by the following Formula (3):

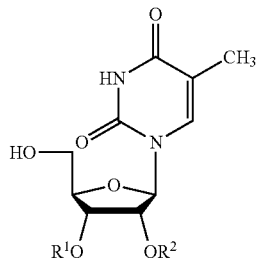

(3)

(wherein $R^1$ and $R^2$ independently represent a protective group for a hydroxy group, or $R^1$ and $R^2$ together form a protective group for two hydroxy groups);

[Step 2] oxidizing the hydroxy group at position 5' in the compound represented by the above Formula (3) to obtain a compound represented by the following Formula (4):

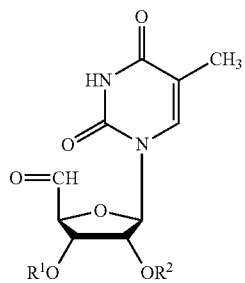

(4)

(wherein $R^1$ and $R^2$ have the same meanings as defined above);

[Step 3] introducing a hydroxymethyl group to position 4' in the compound represented by the above Formula (4) and then performing reduction to obtain a compound represented by the following Formula (5):

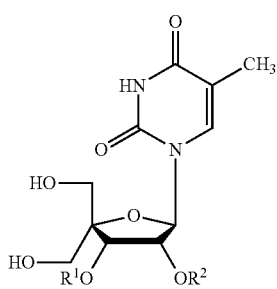

(5)

(wherein $R^1$ and $R^2$ have the same meanings as defined above);

[Step 4] selectively protecting the hydroxy group at position 6' in the compound represented by the above Formula (5) to obtain a compound represented by the following Formula (6):

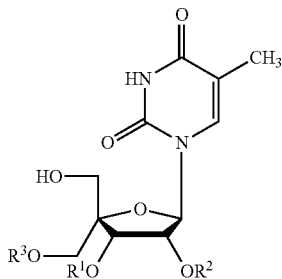

(6)

(wherein $R^1$ and $R^2$ have the same meanings as defined above, and $R^3$ represents a protective group for a hydroxy group), then selectively protecting the hydroxy group at position 5' in the compound represented by the above Formula (6) to obtain a compound represented by the following Formula (7):

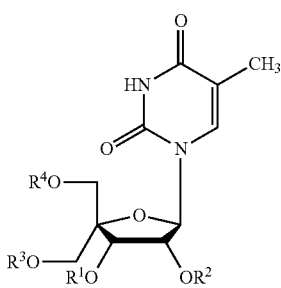

(7)

(wherein $R^1$, $R^2$ and $R^3$ have the same meanings as defined above, and $R^4$ represents a protective group for a hydroxy group), and then selectively removing the protective group of the hydroxy group at position 6' in the compound represented by the above Formula (7) to obtain a compound represented by the following Formula (8):

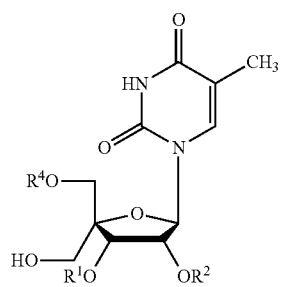

(8)

(wherein $R^1$, $R^2$ and $R^4$ have the same meanings as defined above);

[Step 5] oxidizing the hydroxy group at position 6' in the compound represented by the above Formula (8) to obtain a compound represented by the following Formula (9):

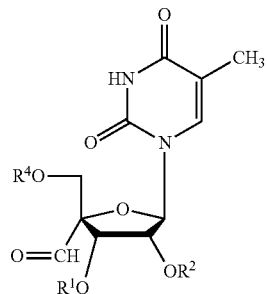

(wherein $R^1$, $R^2$ and $R^4$ have the same meanings as defined above);

[Step 6] subjecting the compound represented by the above Formula (9) to a Wittig reaction to obtain a compound represented by the following Formula (10):

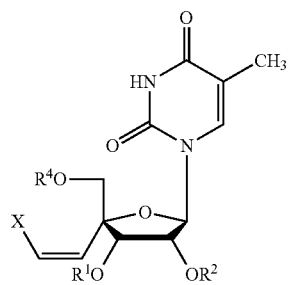

(wherein $R^1$, $R^2$, and $R^4$ have the same meanings as defined above, and X represents a leaving group);

[Step 7] selectively removing the protective groups of the hydroxy groups at positions 2' and 3' in the compound represented by the above Formula (10) to obtain a compound represented by the following Formula (11):

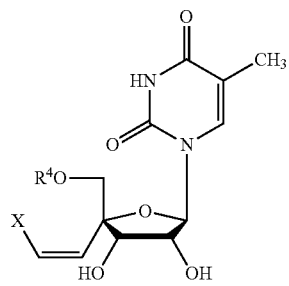

(wherein $R^4$ and X have the same meanings as defined above);

[Step 8] subjecting the compound represented by the above formula (11) and carboxylic ortho ester to an ester exchange reaction and subsequent treatment with a solution of hydrogen halide in carboxylic acid, in the presence of an acid halide or an acid anhydride, to obtain a compound represented by the following Formula (12):

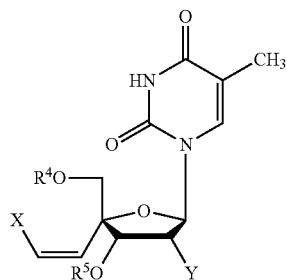

(wherein $R^4$ has the same meaning as defined above, $R^5$ represents a protective group for a hydroxy group, and Y represents a halo group);

[Step 9] subjecting the compound represented by the above Formula (12) to a reductive elimination reaction to obtain a compound represented by the following Formula (13):

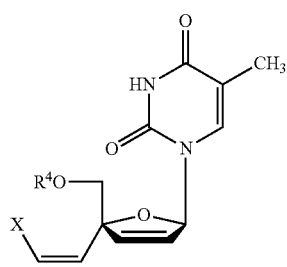

(wherein $R^4$ and X have the same meanings as defined above); and

[Step 10a] treating the compound represented by the above Formula (13) with a base in the presence of a halogenated silane selected from trimethylsilyl chloride, di(t-butyl)methylsilyl chloride, and di(t-butyl)silyl dichloride or a compound capable of being a ligand for Lewis acid-capable metal ions, and then selectively removing the protective group of the hydroxy group at position 5' to obtain 2',3'-didehydro-3'-deoxy-4'-ethynylthymidine represented by the above Formula (1).

2. The process according to claim 1, wherein $R^1$ and $R^2$ together form a ketal type protective group.

3. The process according to claim 2, wherein the ketal type protective group is cyclohexylidene.

4. The process according to claim 1, wherein $R^3$ is a trityl group.

5. The process according to claim 1, wherein $R^4$ is a pivaloyl group.

6. The process according to claim 1, wherein X is a chloro group.

7. The process according to claim 1, wherein $R^5$ is an acetyl group.

8. The process according to claim 1, wherein Y is a bromo group.

9. The process according to claim 1, wherein after the compound represented by the above Formula (5) is obtained in Step 3, the compound is purified via the formation of a sodium salt or a potassium salt thereof and the resulting compound with a low impurity content is subjected to Step 4.

10. The process according to claim 1, wherein after the compound represented by the above Formula (9) is obtained in Step 5, the compound is purified via the formation of a hydrogen sulfite adduct thereof and the resulting compound containing little impurity is subjected to Step 6.

11. The process according to claim 1, wherein, in Step 8, the acid halide is acetyl bromide, the acid anhydride is acetic anhydride, and the solution of hydrogen halide in carboxylic acid is a solution of hydrogen bromide in acetic acid; and in the above Formula (12), $R^5$ represents an acetyl group and Y represents a bromo group.

12. A process for producing 2',3'-didehydro-3'-deoxy-4'-ethynylthymidine represented by the Formula (1):

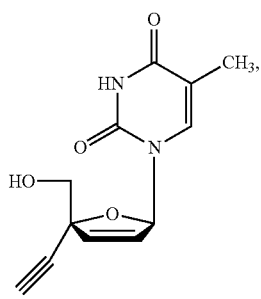
(1)

the process comprising the following Steps 1 to 13,

[Step 1] selectively protecting the hydroxy groups at positions 2' and 3' in the compound represented by the following Formula (2):

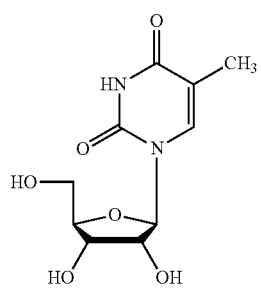
(2)

to obtain a compound represented by the following Formula (3):

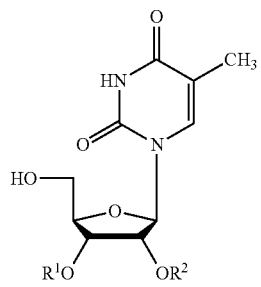
(3)

(wherein $R^1$ and $R^2$ independently represent a protective group for a hydroxy group, or $R^1$ and $R^2$ together form a protective group for two hydroxy groups);

[Step 2] oxidizing the hydroxy group at position 5' in the compound represented by the above Formula (3) to obtain a compound represented by the following Formula (4):

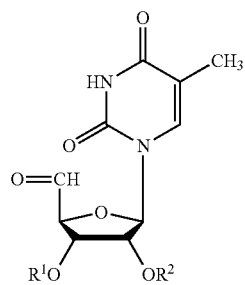
(4)

(wherein $R^1$ and $R^2$ have the same meanings as defined above);

[Step 3] introducing a hydroxymethyl group to position 4' in the compound represented by the above Formula (4) and then performing reduction to obtain a compound represented by the following Formula (5):

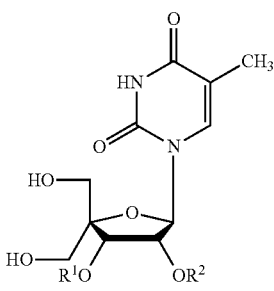
(5)

(wherein $R^1$ and $R^2$ have the same meanings as defined above);

[Step 4] selectively protecting the hydroxy group at position 6' in the compound represented by the above Formula (5) to obtain a compound represented by the following Formula (6):

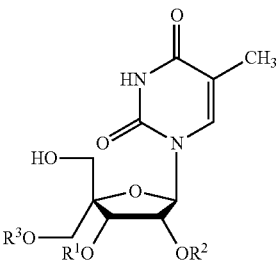
(6)

(wherein $R^1$ and $R^2$ have the same meanings as defined above, and $R^3$ represents a protective group for a hydroxy group), then selectively protecting the hydroxy group at position 5' in the compound represented by the above Formula (6) to obtain a compound represented by the following Formula (7):

(7)

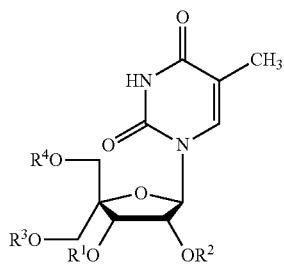

(wherein $R^1$, $R^2$ and $R^3$ have the same meanings as defined above, and $R^4$ represents a protective group for a hydroxy group), and then selectively removing the protective group of the hydroxy group at position 6' in the compound represented by the above Formula (7) to obtain a compound represented by the following Formula (8):

(8)

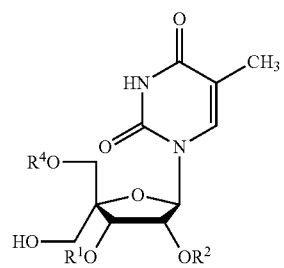

(wherein $R^1$, $R^2$ and $R^4$ have the same meanings as defined above);

[Step 5] oxidizing the hydroxy group at position 6' in the compound represented by the above Formula (8) to obtain a compound represented by the following Formula (9):

(9)

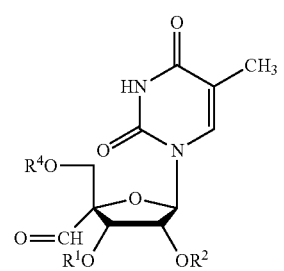

(wherein $R^1$, $R^2$ and $R^4$ have the same meanings as defined above);

[Step 6] subjecting the compound represented by the above Formula (9) to a Wittig reaction to obtain a compound represented by the following Formula (10):

(10)

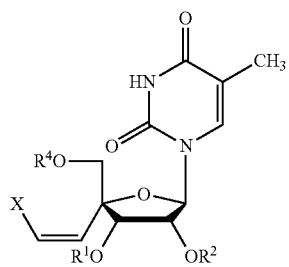

(wherein $R^1$, $R^2$, and $R^4$ have the same meanings as defined above, and X represents a leaving group);

[Step 7] selectively removing the protective groups of the hydroxy groups at positions 2' and 3' in the compound represented by the above Formula (10) to obtain a compound represented by the following Formula (11):

(11)

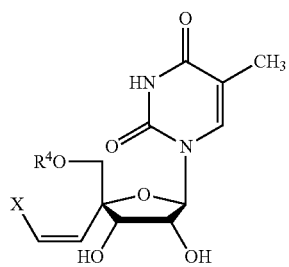

(wherein $R^4$ and X have the same meanings as defined above);

[Step 8] subjecting the compound represented by the above formula (11) and carboxylic ortho ester to an ester exchange reaction and subsequent treatment with a solution of hydrogen halide in carboxylic acid, in the presence of an acid halide or an acid anhydride, to obtain a compound represented by the following Formula (12):

(12)

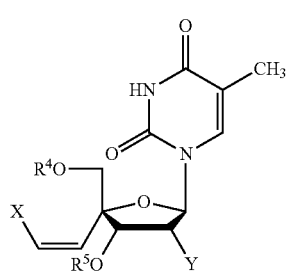

(wherein $R^4$ has the same meaning as defined above, $R^5$ represents a protective group for a hydroxy group, and Y represents a halo group);

79

[Step 9] subjecting the compound represented by the above Formula (12) to a reductive elimination reaction to obtain a compound represented by the following Formula (13):

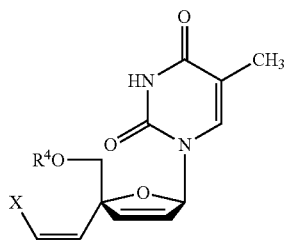
(13)

(wherein R⁴ and X have the same meanings as defined above);

[Step 10b] selectively removing the protective group of the hydroxy group at position 5' in the compound represented by the above Formula (13) to obtain a compound represented by the following Formula (14):

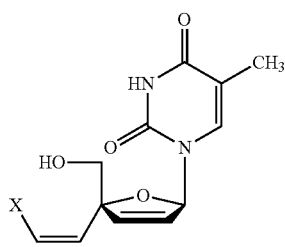
(14)

(wherein X has the same meaning as defined above);

[Step 11a] selectively protecting the hydroxy group at position 5' in the compound represented by the above Formula (14) to obtain a compound represented by the following Formula (15):

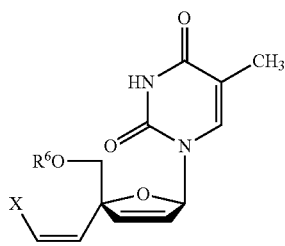
(15)

(wherein X has the same meaning as defined above, and R⁶ represents a protective group for a hydroxy group);

80

[Step 12] treating the compound represented by the above Formula (15) with a base to obtain a compound represented by the following Formula (16):

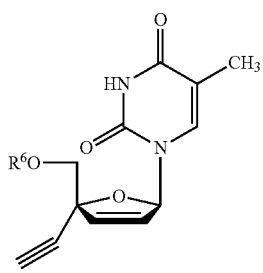
(16)

(wherein R⁶ has the same meaning as defined above); and

[Step 13] selectively removing the protective group of the hydroxy group at position 5' in the compound represented by the above Formula (16) to obtain 2',3'-didehydro-3'-deoxy-4'-ethynylthymidine represented by the above Formula (1).

13. The process according to claim 12, wherein R⁶ is a trityl group or a tetrahydropyranyl group.

14. A process for producing 2',3'-didehydro-3'-deoxy-4'-ethynylthymidine represented by the Formula (1):

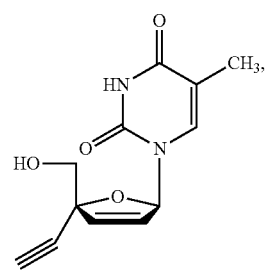
(1)

the process comprising the following Steps 1 to 11b.

[Step 1] selectively protecting the hydroxy groups at positions 2' and 3' in the compound represented by the following Formula (2):

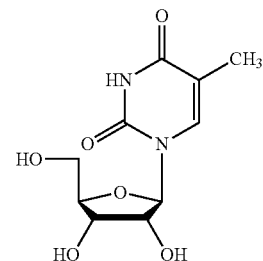
(2)

to obtain a compound represented by the following Formula (3):

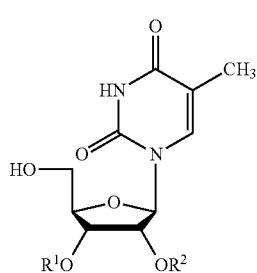

(3)

(wherein $R^1$ and $R^2$ independently represent a protective group for a hydroxy group, or $R^1$ and $R^2$ together form a protective group for two hydroxy groups);

[Step 2] oxidizing the hydroxy group at position 5' in the compound represented by the above Formula (3) to obtain a compound represented by the following Formula (4):

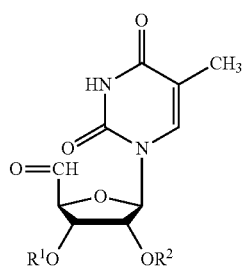

(4)

(wherein $R^1$ and $R^2$ have the same meanings as defined above);

[Step 3] introducing a hydroxymethyl group to position 4' in the compound represented by the above Formula (4) and then performing reduction to obtain a compound represented by the following Formula (5):

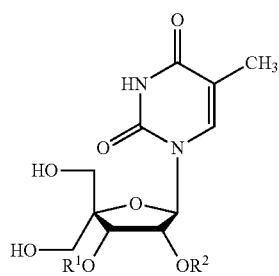

(5)

(wherein $R^1$ and $R^2$ have the same meanings as defined above);

[Step 4] selectively protecting the hydroxy group at position 6' in the compound represented by the above Formula (5) to obtain a compound represented by the following Formula (6):

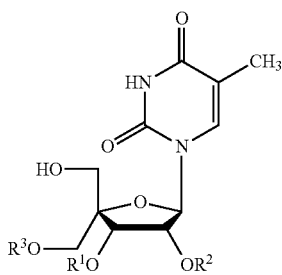

(6)

(wherein $R^1$ and $R^2$ have the same meanings as defined above, and $R^3$ represents a protective group for a hydroxy group), then selectively protecting the hydroxy group at position 5' in the compound represented by the above Formula (6) to obtain a compound represented by the following Formula (7):

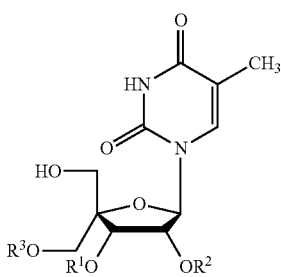

(7)

(wherein $R^1$, $R^2$ and $R^3$ have the same meanings as defined above, and $R^4$ represents a protective group for a hydroxy group), and then selectively removing the protective group of the hydroxy group at position 6' in the compound represented by the above Formula (7) to obtain a compound represented by the following Formula (8):

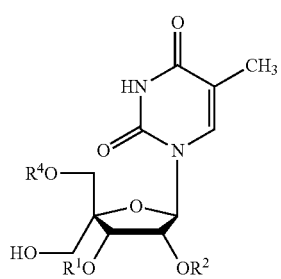

(8)

(wherein $R^1$, $R^2$ and $R^4$ have the same meanings as defined above);

[Step 5] oxidizing the hydroxy group at position 6' in the compound represented by the above Formula (8) to obtain a compound represented by the following Formula (9):

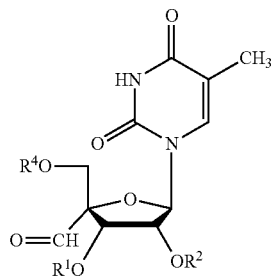

(9)

(wherein $R^1$, $R^2$ and $R^4$ have the same meanings as defined above);

[Step 6] subjecting the compound represented by the above Formula (9) to a Wittig reaction to obtain a compound represented by the following Formula (10):

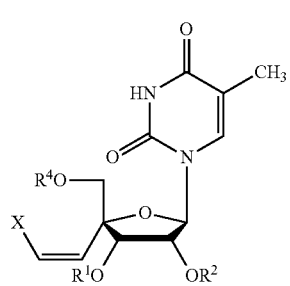

(10)

(wherein $R^1$, $R^2$, and $R^4$ have the same meanings as defined above, and X represents a leaving group);

[Step 7] selectively removing the protective groups of the hydroxy groups at positions 2' and 3' in the compound represented by the above Formula (10) to obtain a compound represented by the following Formula (11):

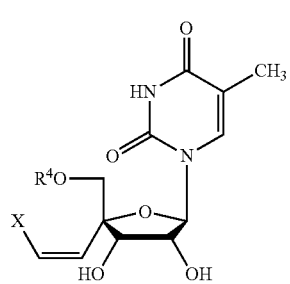

(11)

(wherein $R^4$ and X have the same meanings as defined above);

[Step 8] subjecting the compound represented by the above formula (11) and carboxylic ortho ester to an ester exchange reaction and subsequent treatment with a solution of hydrogen halide in carboxylic acid, in the presence of an acid halide or an acid anhydride, to obtain a compound represented by the following Formula (12):

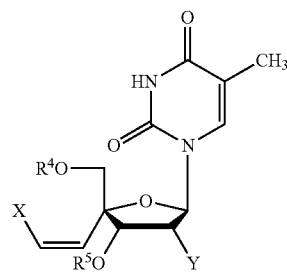

(12)

(wherein $R^4$ has the same meaning as defined above, $R^5$ represents a protective group for a hydroxy group, and Y represents a halo group);

[Step 9] subjecting the compound represented by the above Formula (12) to a reductive elimination reaction to obtain a compound represented by the following Formula (13):

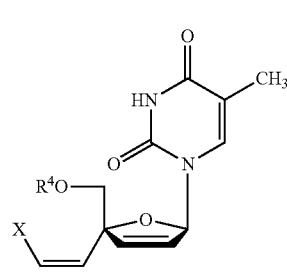

(13)

(wherein $R^4$ and X have the same meanings as defined above);

[Step 10b] selectively removing the protective group of the hydroxy group at position 5' in the compound represented by the above Formula (13) to obtain a compound represented by the following Formula (14):

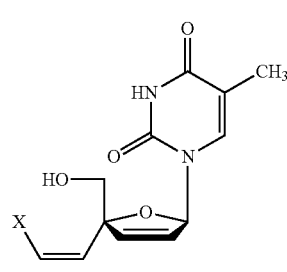

(14)

(wherein X has the same meaning as defined above);

[Step 11b] treating the compound represented by the above Formula (14) with a base to obtain 2',3'-didehydro-3'-deoxy-4'-ethynylthymidine represented by the above Formula (1).

15. A compound represented by the following Formula (10):

(10)

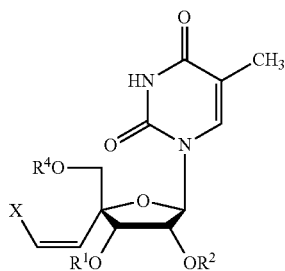

(wherein $R^1$ and $R^2$ together form a protective group for two hydroxy groups, $R^4$ represents a protective group for a hydroxy group, and X represents a leaving group).

16. The compound according to claim 15, wherein $R^4$ is an acyl type protective group, an optionally substituted aralkyloxy carbonyl group, an acyl group, a trityl type protective group, an acetal type protective group, a silyl type protective group, an optionally substituted alkoxycarbonyl group having 2 to 13 carbon atoms, or an optionally substituted aralkyl group having 7 to 20 carbon atoms.

17. The compound according to claim 15, wherein $R^4$ is a pivaloyl group.

18. The compound according to claim 15, wherein X is a halo group or an optionally substituted alkylsulfonyloxy group having 1 to 4 carbon atoms.

19. The compound according to claim 15, wherein X is a chloro group, a bromo group, an iodo group, or a trifluoromethane sulfonyloxy group.

20. A compound represented by the following Formula (11):

(11)

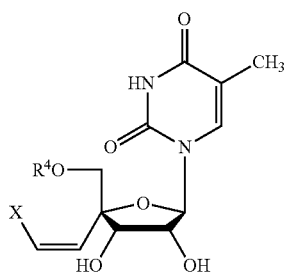

(wherein $R^4$ represents a protective group for a hydroxy group, and X represents a leaving group).

21. A compound represented by the following Formula (13):

(13)

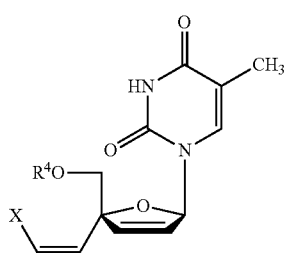

(wherein $R^4$ represents a protective group for a hydroxy group, and X represents a leaving group).

22. The compound according to claim 21, wherein $R^4$ is an acyl type protective group, an optionally substituted aralkyloxy carbonyl group, an acyl group, a trityl type protective group, an acetal type protective group, a silyl type protective group, an optionally substituted alkoxycarbonyl group having 2 to 13 carbon atoms, or an optionally substituted aralkyl group having 7 to 20 carbon atoms.

23. The compound according to claim 21, wherein $R^4$ is a pivaloyl group, a trityl group, or a tetrahydropyranyl group.

24. The compound according to claim 21, wherein X is a halo group or an optionally substituted alkylsulfonyloxy group having 1 to 4 carbon atoms.

25. The compound according to claim 21, wherein X is a, chloro group, a bromo group, an iodo group or a trifluoromethane sulfonyloxy group.

26. A compound represented by the following Formula (5-2):

(5-2)

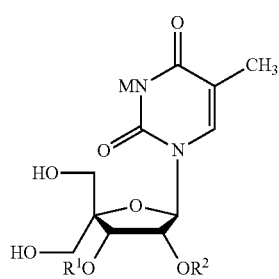

(wherein $R^1$ and $R^2$ independently represent a protective group for a hydroxy group, or $R^1$ and $R^2$ together form a protective group for a hydroxy group, and M represents a sodium ion or a potassium ion).

27. The compound according to claim 26, represented by the following Formula (5-3):

(5-3)

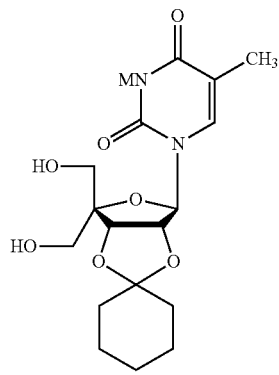

(wherein M represents a sodium ion or a potassium ion).

* * * * *